US009717252B2

(12) United States Patent
Burr et al.

(10) Patent No.: US 9,717,252 B2
(45) Date of Patent: Aug. 1, 2017

(54) BIOLOGICAL CONTROL OF CROWN GALL DISEASE ON GRAPEVINES

(71) Applicant: Cornell University, Ithaca, NY (US)

(72) Inventors: Thomas J. Burr, Geneva, NY (US); Desen Zheng, Geneva, NY (US)

(73) Assignee: Cornell University, Ithaca, NY (US)

( * ) Notice: Subject to any disclaimer, the term of this patent is extended or adjusted under 35 U.S.C. 154(b) by 182 days.

(21) Appl. No.: 14/395,114

(22) PCT Filed: Mar. 15, 2013

(86) PCT No.: PCT/US2013/031950
§ 371 (c)(1),
(2) Date: Oct. 17, 2014

(87) PCT Pub. No.: WO2013/158287
PCT Pub. Date: Oct. 24, 2013

(65) Prior Publication Data
US 2015/0105255 A1 Apr. 16, 2015

Related U.S. Application Data

(60) Provisional application No. 61/635,160, filed on Apr. 18, 2012.

(51) Int. Cl.
| C12N 1/20 | (2006.01) |
| C12N 15/00 | (2006.01) |
| C12N 9/10 | (2006.01) |
| C07H 21/04 | (2006.01) |
| C12Q 1/68 | (2006.01) |
| A61K 38/51 | (2006.01) |
| A01N 63/00 | (2006.01) |
| C12N 15/82 | (2006.01) |
| A01H 3/00 | (2006.01) |
| C07K 14/195 | (2006.01) |
| C12N 1/36 | (2006.01) |
| C12N 9/12 | (2006.01) |
| A23L 2/02 | (2006.01) |
| C12N 15/74 | (2006.01) |
| C12Q 1/02 | (2006.01) |
| A23L 19/00 | (2016.01) |

(52) U.S. Cl.
CPC ............ A01N 63/00 (2013.01); A01H 3/00 (2013.01); A23L 2/02 (2013.01); A23L 19/00 (2016.08); C07K 14/195 (2013.01); C12N 1/36 (2013.01); C12N 9/1288 (2013.01); C12N 15/743 (2013.01); C12N 15/8286 (2013.01); C12Q 1/02 (2013.01); C12Y 207/08007 (2013.01); A23V 2002/00 (2013.01); G01N 2500/04 (2013.01)

(58) Field of Classification Search
CPC ............ C12N 9/1288; C12N 15/743; C12N 15/8286
See application file for complete search history.

(56) References Cited

U.S. PATENT DOCUMENTS

2006/0035377 A1 2/2006 Subramanian et al.

FOREIGN PATENT DOCUMENTS

WO WO-2005/023005 A1 3/2005

OTHER PUBLICATIONS

Supplementary European Search Report for European Patent Application No. 13779028.3, dated Dec. 15, 2015 (6 pages).
Burr et al., "Grapevine cuttings as potential sites of survival and means of dissemination of Agrobacterium tumefaciens," Plant Dis. 68(11):976-978 (1984).
Burr et al., "Isolation of Agrobacterium tumefaciens Biovar 3 from grapevine galls and sap, and from vineyard soil," Phytopathology 73(2):163-165 (1983).
Burr et al., "Characterization of Agrobacterium vitis strains isolated from feral Vitis riparia," Plant Dis. 83(2):102-107 (1999).
Burr et al., "Induction of grape tissue necrosis and tobacco leaf HR by Agrobacterium vitis requires a polyketide synthase and a nonribosomal peptide synthase," Phytopathology 101(6):S23 (2011).
Carle et al., "A gene cluster in Agrobacterium vitis homologous to polyketide synthase operons associated with grape necrosis and hypersensitive response induction on tobacco," FEMS Microbiol Lett. 289(1):90-96 (2008).
Chen et al., "Biological Control of Grape Crown Gall by Rahnella aquatilis HX2," Plant Dis. 91:957-963 (2007).
Chilton et al., "Stable incorporation of plasmid DNA into higher plant cells: the molecular basis of crown gall tumorigenesis," Cell 11:263-271 (1977).
Dandurishvili et al., "Broad-range antagonistic rhizobacteria Pseudomonas fluorescens and Serratia plymuthica suppress Agrobacterium crown gall tumours on tomato plants," J Appl Microbiol. 110:341-352 (2010).
Eastwell et al., "Characterizing potential bacterial biocontrol agents for suppression of Rhizobium vitis, causal agent of crown gall disease in grapevines," Crop Protection 25:1191-1200 (2006).
Farrand, Agrobacterium Radiobacter strain K84: a model biocontrol system. *New Directions in Biological Control: Alternatives for Suppressing Agricultural Pests and Diseases.* R.R. Baker, and P.E. Dunns, 679-691 (1990).
Goodman et al., "The occurrence of Agrobacterium tumefaciens in grapevine-propogated material and a simplified indexing system," Am J Enol Vitic 38(3):189-193 (1987).

(Continued)

Primary Examiner — Yong Pak
(74) Attorney, Agent, or Firm — Clark & Elbing LLP

(57) ABSTRACT

Derivatives of *Agrobacterium vitis* strain F2/5 are disclosed. These derivatives were generated following homologous recombination with an internal fragment of targeted genes resulting in gene disruption by insertion of a copy of suicide vector pVIK165. The genes disrupted were F-avi5813 encoding a phosphopantetheinyltransferase, F-avi4329 encoding an aminotransferase and F-avi0838 (rirA) encoding an iron responsive transcriptional regulator. Such derivatives control crown gall on grapevines. In addition, these derivatives did not induce roots necrosis but enhanced root development and callus formation. On young stem explants, it was shown as well that the F2/5 derivatives are necrosis-negative.

18 Claims, 21 Drawing Sheets

(56) References Cited

OTHER PUBLICATIONS

Kawaguchi et al., "Biological control of crown gall of grapevine, rose, and tomato by nonpathogenic Agrobacterium vitis strain VAR03-1," Phytopathology 98(11):1218-1225 (2008).

Liang et al., "A biotype 3 strain of Agrobacterium radiobacter inhibits crown gall formation on grapevine," Acta Microbiol Sin 30(3):165-171 (1990) (English language translation provided).

Otten et al., "Phylogenetic Relationships Between Agrobacterium vitis Isolates and Their Ti Plasmids," MPMI 9(9):782-786 (1996).

Smith et al., "Identification of common molecular subsequences," J Mol Biol. 147:195-7 (1981).

Smith et al., "Comparison of biosequences," Advances in Applied Mathematics 2:482-489 (1981).

Zheng et al., "Inhibition of grape crown gall by agrobacterium vitis F2/5 requires two nonribosomal peptide synthetases and one polyketide synthase," Mol Plant Microbe Interact 29(2):109-18 (2016).

Bazzi et al., "Biological control of Agrobacterium vitis using non-tumorigenic agrobacteria," Vitis 38(1): 31-35 (1999).

Donadio et al., "Polyketide synthases and nonribosomal peptide synthetases: the emerging view from bacterial genomics," Nat Prod Rep 24(5):1073-109 (2007).

Herlache et al., "Expression of a crown gall biological control phenotype in an avirulent strain of Agrobacterium vitis by addition of the trifolitoxin production and resistance genes," BMC Biotechnol 2:2 (2002) (7 pages).

Herlache et al., "Mutations that affect *Agrobacterium vitis*-induced grape necrosis also alter its ability to cause a hypersensitive response on tobacco," Phytopathology 91:966-972 (2011).

Kalogeraki et al., "Suicide plasmids containing promoterless reporter genes can simultaneously disrupt and create fusions to target genes of diverse bacteria," Gene 188(1):69-75 (1997).

Liu et al., "Agrobacterium Ti plasmid indoleacetic acid gene is required for crown gall oncogenesis," Proc Natl Acad Sci USA 79(9):2812-6 (1982).

Lorio et al., "Y4xP, an open reading frame located in a type III protein secretion system locus of Sinorhizobium fredii USDA257 and USDA191, encodes cysteine synthase," Mol Plant Microbe Interact 19:635-643 (2006).

Marie et al., "Rihizobium type III secretion systems: legume charmers or alarmers?," Current Opinion in Plant Biology 4:336-342 (2001).

Ngok-Ngam et al., "Roles of Agrobacterium tumefaciens RirA in iron regulation, oxidative stress response, and virulence," J Bacteriol. 191(7):2083-90 (2009).

Slater et al., "Genome sequences of three agrobacterium biovars help elucidate the evolution of multichromosome genomes in bacteria," J Bacteriol. 191(8):2501-11 (2009).

Wang et al., "The quorum-sensing system AvsR-AvsI regulates both long-chain and short-chain acyl-homoserine lactones in Agrobacterium vitis E26," Antonie van Leeuwenhoek 93(3):267-73 (2008).

Zheng et al., "A luxR homolog, aviR, in Agrobacterium vitis is associated with induction of necrosis on grape and a hypersensitive response on tobacco," Mol Plant Micorbe Interact 16(7):650-8 (2003).

Zheng et al., "An Sfp-type PPTase and associated polyketide and nonribosomal peptide synthases in Agrobacterium vitis are essential for induction of tobacco hypersensitive response and grape necrosis," Mol Plant Microbe Interact. 26:812-22 (2013).

International Search Report for International Patent Application No. PCT/US2013/031950, mailed Jul. 1, 2013 (5 pages).

International Preliminary Report on Patentability for International Patent Application No. PCT/US2013/031950, issued Oct. 21, 2014 (13 pages).

Written Opinion of the International Searching Authority for International Patent Application No. PCT/US2013/031950, mailed Jul. 1, 2013 (12 pages).

Communication pursuant to Article 94(3) EPC for European Patent Application No. 13779028.3, dated Oct. 24, 2016 (4 pages).

Figure 1. Crown gall at wounds on woody grape tissues inoculated with CG49 or CG49 mixed with F2/5 or with F2/5 mutants. Arrows point to inoculated wound sites.
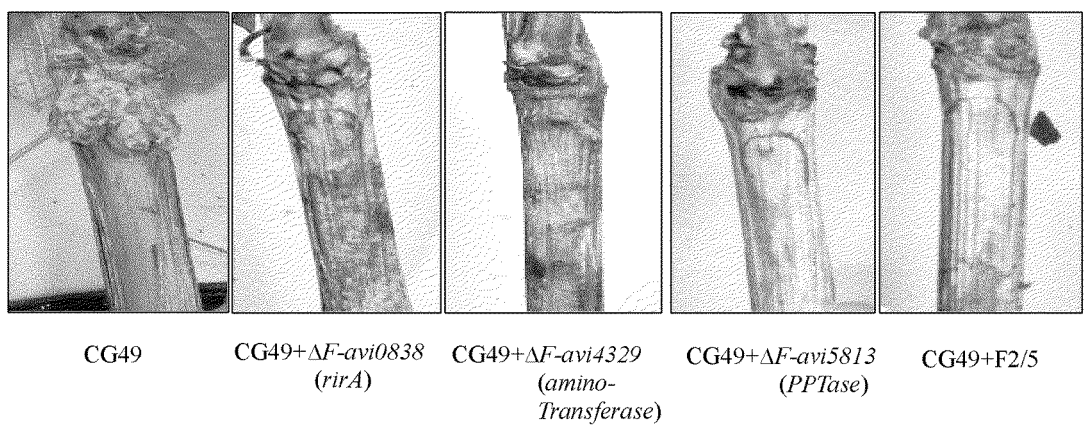
CG49    CG49+ΔF-avi0838    CG49+ΔF-avi4329    CG49+ΔF-avi5813    CG49+F2/5
             (rirA)           (amino-            (PPTase)
                             Transferase)

Figure 2. Dormant grape cuttings were soaked in suspensions of F2/5, F2/5 mutants or water and then rooted. Note heavy necrosis on roots of F2/5 treated cutting. Arrows point to necrosis on roots
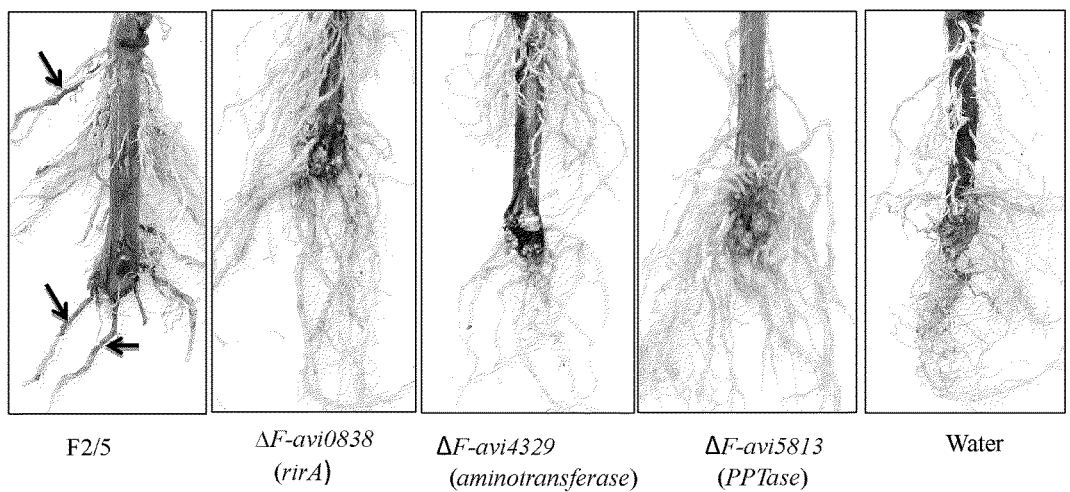
F2/5     ΔF-avi0838 (rirA)     ΔF-avi4329 (aminotransferase)     ΔF-avi5813 (PPTase)     Water Figure 3. Effects of F2/5 and three F2/5 mutants on grape shoot necrosis.
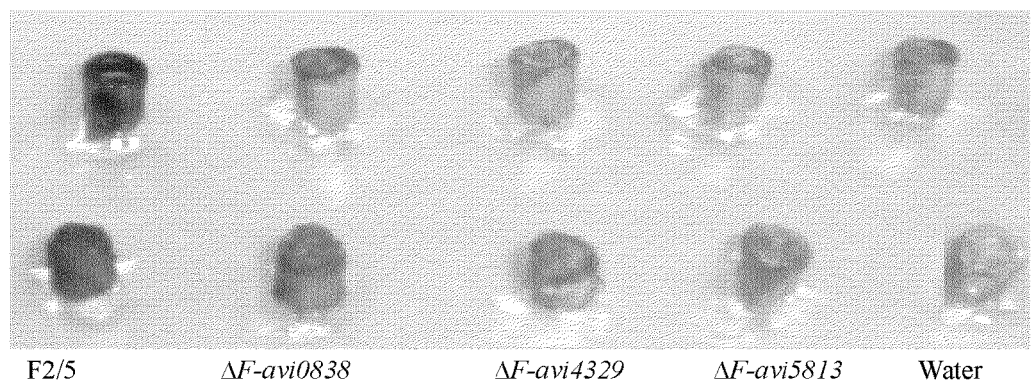
F2/5  ΔF-avi0838  ΔF-avi4329  ΔF-avi5813  Water Figure 4. Effects of treatments with *A. vitis* F2/5 and its mutants on grapevine grafts
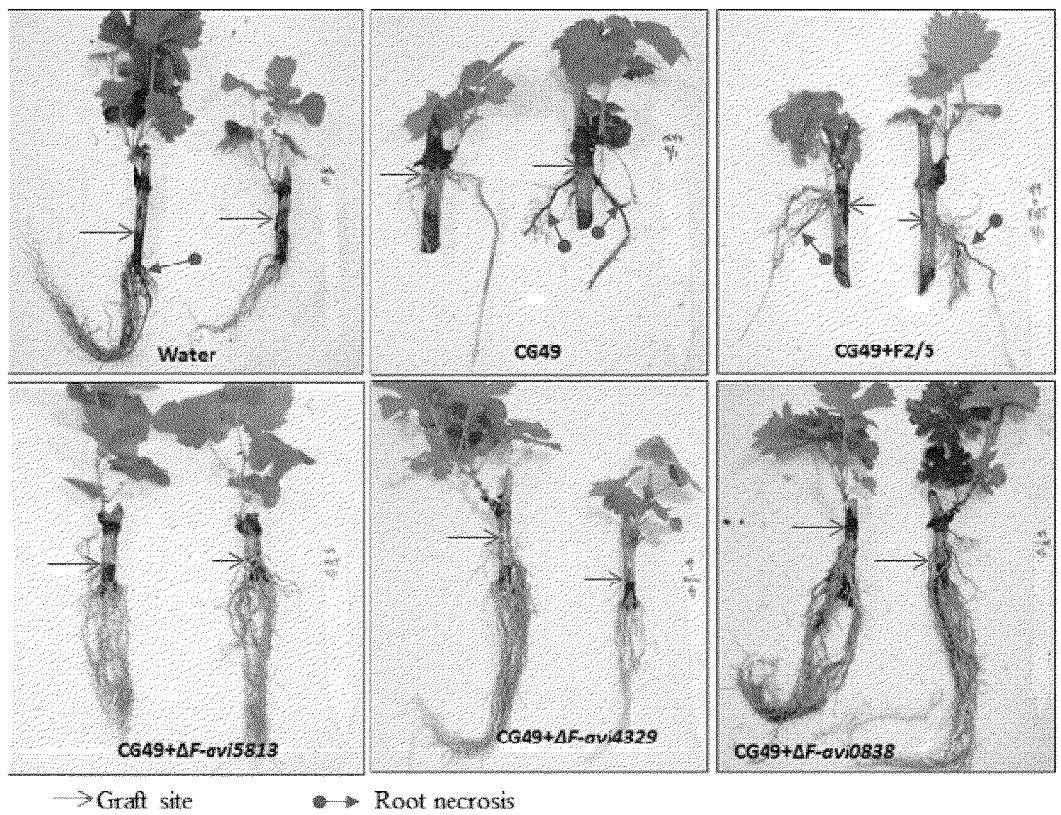

The gene organization and annotation of Avs locus (A) and the effects of knock-down mutant ΔP1391 and ΔP1396 on biological control (B).

FIG. 6A

F-avi5813 (avi5813 in A. vitis strain F2/5) encoding phosphopantetheinyltransferase (PPTase)

DNA sequence:

atgagccagcgggccaataatcaggtggaaatatactcctcatgccctgtgcctccgcttttcgaggccttcatctc
gcatcgcgctgtttgcttccgtcacaatgattttacgcccgaagcggcgattgaacttggcgtgcccctgccagaaa
gcatgggaaaggcggtcgccaagcgcaaggcggaatatgtggggcggacggttctgcgccatggaggcgattgtggcg
caaaccggccagcctgccgcacccgttacagcggggaccgcgtggcgaaccggtctggccgtcagggctggtcggctc
gattacccatacgcacgggtttgctgcggcagccgttgccgatgcagctcgatttcgcagccttggcatggatacag
aacaggtcatgacagcgcaggtcatgggcaatgtccgagagggatctgcggtccggaagaccggtttggggccagc
agctctcttttgccggaacttcataccaccctggtgttttctgccaaggaaagcctgttcaaatgtctttatccatt
ggttgaaaaaatgttctggttcgaagacgcgctgatccggatcgatccggatcgggatggtctgtttaccgccgaat
tgctgtcacgcctccatgtggaatttccggcgggaacagtgatcgaaggacgcttttgcctgacgcgggtctggtt
cataccggcatcagccttgcgaaagatgaggctgcgttataa (SEQ ID NO: 1)

Amino acid sequence:

MSQRANNQVEIYSSCPVPPLFEAFISHRAVCFRHNDFTPEAAIELGVPLPESMGKAVAKRKAEYVGGRFCAMEAIVA
QTGQPAAPVTAGPRGEPVWPSGLVGSITHTHGFAAAAVADAARFRSLGMDTEQVMTAQVMGNVRERICGPEDRFGAS
SSLLPELHTTLVFSAKESLFKCLYPLVEKMFWFEDALIRIDPDRDGLFTAELLSRLHVEFPAGTVIEGRFCLTPGLV
HTGISLAKDEAAL (SEQ ID NO: 2)

F-avi4329 (avi4329 in A. vitis strain F2/5) encoding aminotransferase

DNA sequence:

5'-
atgaatgagaacaagcgtcaggatctgctggcccgtatgcgtggcgtacaaaaggatgtggaccggagccgggccag
ccgcagccagcagagcgtgtcgcgcagccagccaggttttgccgaattgcctgaatataagcaggtggtgatgcaga
agcttgtcagcgagcaactgaacatgcccaatccgttcaccgggcgcatgagagcgcctccgggcaacggctgat
atcgacgggcgcgcctatgataattttgcctcctatgattatctcggcttgaacagtgatccacgcattcgcgatgc
cgccatggcggccatcgaccagttcggtatctcggcctccgccagccggcttgttgccggtgagcgcaccatccatg
ccgagctggaaaaggcctttgccaaaaattaccagaccgaggacgccatctgtttcgtcagcggctatctcaccaat
gtcacgaccatcggcagcttgatgggggccgaaagacctggtgatccatgacgagttcattcacaacagcgccctgac
gggcatcaagctgtcgggtgccaatcgccgcttcttcaagcataatgacatggcggacctggaccgtattcttgcga
gcctcgcccccttgcatgaacgaatcctggtgatctccatggatgagacgttgccgatctg
ccgggccttcttgcattgaaaaagcagtataatttctggctgatgatggacgaggccattctctgggcgtacttgg
acagcgtggccacggcattttcgaacatttcaatctcgatccagccgatgtcgatatctggatggggacgctgtcga
aaaccacctgtagctgcggcggctatgttgccggcagtgaagcgctgatcacgctgttgaaggcgcaggccggtggt
ttcgtttatagtgtcggcttggcaccagcgctggcggctgcggccatcgccagcctgtcggtgctggacgaggagcc
ggaccgggtagaggctttgcgtcgcaacagccagcttttcctggagcaagccaagctacggggctggataccggtc
tgagcgaaggtttctcggtggtgcctgtgatcgttgccgattcggtgcgcgctgtgcagcttttccaatgaattgttc
gaggcaggcatcaatgcgctgccgatcatctatcccgcagtaccggaaggtctggcacgtctgcggttcttcatcac
cagcgcccacacgcccgaccagatacccgcagcgtggacaaggtggacattctggatcggctgaaggccgaga
atttcggcatgggctcgatggatgtccagaaggtcatgctgcaattggcgcagcgctga-3' (SEQ ID NO: 3)

Amino acid sequence:

MNENKRQDLLARMRGVQKDVDRSRASRSQQSVSRSQPGFAELPEYKQVVMQKLVSEQLNMPNPFYRAHESASGATAD
IDGRAYDNFASYDYLGLNSDPRIRDAAMAAIDQFGISASASRLVAGERTIHAELEKAFAKNYQTEDAICFVSGYLTN
VTTIGSLMGPKDLVIHDEFIHNSALTGIKLSGANRRFFKHNDMADLDRILASLAPLHERILVISEGIFSMDGDVADL
PGLLALKKQYNFWLMMDEAHSLGVLGQRGHGIFEHFNLDPADVDIWMGTLSKTTCSCGGYVAGSEALITLLKAQAGG
FVYSVGLAPALAAAAIASLSVLDEEPDRVEALRRNSQLFLEQAKLRGLDTGLSEGFSVVPVIVADSVRAVQLSNELF
EAGINALPIIYPAVPEGLARLRFFITSAHTPDQITRSVDKVADILDRLKAENFGMGSMDVQKVMLQLAQR (SEQ
ID NO: 4)

F-avi0838(avi0838 in A. vitis F2/5) encoding Iron-responsive repressor (RirA)

FIG. 6B

DNA sequence:

5'-
atgcgcttgacgaagcagaccaattacgcggtacgcattctgatgtattgcgcggcgaacaaggaccacctgagccg
tatcccggaaattgccaaggcctatggcgtctccgaactgttcctgttcaaaatccttcagccgctcaacaaggcgg
gtctggtggaaaccgtgcgtggccgcaatggcggcgtgcgcctaggtcgtgcgcctgaaaagatcagcctgtttgac
gtggtcaaggtcacggaagacagctttgcgatggccgaatgcttcgaggacgatggcgaggtcgattgcccgttgat
cgacagctgcggcctgaattcggcgctgcgcaaggcgctcaacgcttttcttcgcggtgctggcggaatattccatcg
atgatctggtcaaggcccgcccgcagatcaacttttttgctgggtatcgaggatctgcctcgtctggcggcggcaccg
gctgcctga-3' (SEQ ID NO: 5)

Amino acid sequence:

MRLTKQTNYAVRILMYCAANKDHLSRIPEIAKAYGVSELFLFKILQPLNKAGLVETVRGRNGGVRLGRAPEKISLFD
VVKVTEDSFAMAECFEDDGEVDCPLIDSCGLNSALRKALNAFFAVLAEYSIDDLVKARPQINFLLGIEDLPRLAAAP
AA (SEQ ID NO: 6)

**F-avi4374 (avi4374 in *A. vitis* F2/5) encoding a member of transcriptional regulator LuxR family *aviR***

DNA sequence:

5'-
gtgagtgtcaatcatctcatacagttttttggctgtatctcagggatgccgaagtcgcgaggagctgatcctagaatt
ggagaaactcctcgaatttataaattcgattattacggcctcgtgcgcagtcccaaacctgaccaaaaccccatgt
cgctggtgcttgcaggacgctggccggaaaaatggccgcaggtctatatcacgaaaaaattcgtgctgatcgaccct
gccattcgctatctggcgcaagcgcaacggccgttccgttggagcgaaacgctgacggcattcagccaggacccaca
tttcaaacgcatgcagcggatgatgatggatgcccagcgctttggtctcgaggaaggctatatcttcccatccacg
ggcggggcggattgctggccaacatgaccattggcgggagaccggtggaactgaccccgattgagatcatgctgttc
gacacggtggcgaaatgcgccttctggcggctggcggaaatcaatggcgaagacgaactgctgtcgatggtgcaaaa
agtcgatgtgcgcctgacccgacgcgagcttgaaattctcaattatctcgggagggcatgacctcgaacgagatga
gcaaattgctcgagatttcgaaccacaccgtcgattggtacgtcaacgaattgcaggataagttgaacgccaagaat
cggcaacatatggtagcaattgcttatcgtctcggcctgatcagctga-3' (SEQ ID NO: 7)

Amino acid sequence:

MSVNHLIQFLAVSQGCRSREELILELEKLLEFYKFDYYGLVRSPKPDQNPMSLVLAGRWPEKWPQVYITKKFVLIDP
AIRYLAQAQRPFRWSETLTAFSQDPHFKRMQRMMMDAQRFGLEEGYIFPIHGRGGLLANMTIGGRPVELTPIEIMLF
DTVAKCAFWRLAEINGEDELLSMVQKVDVRLTRRELEILNYLGEGMTSNEMSKLLEISNHTVDWYVNELQDKLNAKN
RQHMVAIAYRLGLIS (SEQ ID NO: 8)

**F-avi1696 (avi1696 in *A. vitis* F2/5) encoding a proteolytic subunit of ATP-dependent Clp protease *clpP1***

DNA sequence:

5'-
atgagaaatccagttgataccgccatggctctggtgcctatggttgtggagcagaccaatcgcggcgaacggtccta
cgacatctactcgcgtctgttgaaggagcgcatcattttcctgaccggaccggttgaggatcatatggcgtcgcttg
tctgcgcccagctgctgtttctggaagcggaaaatccgaagaaggaaatcgcgatctacatcaattctcccggcggc
gtcgtgactgccggcatggcgatctacgatacgatgcagttcatccgtccggccgtctcgacgctgtgcgtcggcca
ggccgcctcgatgggtcgctgctgctggcggccggcgaaaaggcatgcgctttgcgaccccaacgcccgcatca
tggtgcatcagccgtccggcggtttccaggggcaggcctccgacatcgagcggcatgcccgcgacatcatcaagatg
aagcgtcgcttgaacgaggtttatgtcaagcacactggacgcacgctggaagaagtcgagcacacgcttgaccgcga
ccacttcatggaatccacggaagctaaggattggggtctgatcgacaagatcctgacgacgcgctccgaaattgaag
gggtaacgccttcttga-3' (SEQ ID NO: 9)

Amino acid sequence:

MRNPVDTAMALVPMVVEQTNRGERSYDIYSRLLKERIIFLTGPVEDHMASLVCAQLLFLEAENPKKEIAIYINSPGG
VVTAGMAIYDTMQFIRPAVSTLCVGQAASMGSLLLAAGEKGMRFATPNARIMVHQPSGGFQGQASDIERHARDIIKM
KRRLNEVYVKHTGRTLEEVEHTLDRDHFMESTEAKDWGLIDKILTTRSEIEGVTPS (SEQ ID NO: 10)

FIG. 6C
F-avi3342 (avi3342 in A. vitis F2/5) encoding nonribosomal peptide synthetase DNA sequence:

atgtcttttgtaggcagacatgagcaggttttccggtttctcttgcgcaggcaggcttgtgggtcaaacaaaaggt
agctcccgccgatctgagctttgtccttgctgaatccatcgaaattcacggtcccgttcatccaggactgttctgcc
aggcgttgcgccgcttgtcagatgatgttgctgtcacacggtctcgcatcaaggaaatcgaaggcagccacatcag
gttgtcatggcggcctattgcggcgtcttttgacgtgatcgatttcagcggtgctgacaatcctggcgcaagcgccat
ggactggatgcgcaagcagatgtctaagccgctcgatcttgccaatgacaatctctgggggtcttcacttttgaagc
tcggggccacagaatgggtctggtatcattgggcacatcatatcatcatggatgggttctctggcggcttgctggcc
cggcggctggccgatatttattcggcgctggcccagggcaaccagccggagccctatgattgcggttctccgcagga
attgctggagcttgagcgcacctaccgcgattcggtgcatttccagcgcgacaaggcctattggtcggagcagatga
agggtctgccggagccggtgaccttgatgaagaaaaaggcgagccatccggtggcctgttgcgccatacgacggtc
atcgatcgccagacggtcaaggcgcttgctgagatcagccgtggctttggcgccagcgtgccacaggccttgattgc
ccttgtcgcggcctattacgccaaggcgaccgactgcgaagagctgaccatggtcaccatggtgacggcccggatca
gccagacgatgcgccgcattccgggcatgaccgccaatgcggttcctctgcggttttcgatcacgccggacctgtcc
tggcgcgaattgaccggtcaggtttcccagcagatgagcggggcgctgcgctatcagcgctatcgctatgaggatat
tcgccgcgatctcggcatggtccgccaggatgcgcagattgcctggctgggcgtcaatatcgagccttcgactacg
atctacgcttttgatggacagccaaccaccgtgcacaaccttcgaatggcacgatgacggatttcaccatcttcgcc
tatgaccgtggtgacaatggcgacctgcgcatcgattttgatgccaatccggcgctctatacgctggaagagctggc
cgatcacgaggcgcggttcacccgcatgttgagagatcctcgcgacgcctgaacagccctgcgcgatttcagcc
tgctgtcgaagtgggagcggcaggaaattctcaccgactggaacgatacgtcccataagctgccggatcagacctgg
ccggaattgttccgggcgcaggcggcacgccggcggtagcgctatccttggcggtcgccagatgaccta
tggtgagctggatgccgcctccgatcatctggctgctatctgatggaaaagggcgccgtaccggttctctggtgg
ctgtggctgtgccgcggtctgaaaacatggttgtggcgctgctggcagtgctcaaaagcggtgccgcctatctaccg
ctcgatccggctgatccagcctcgcgggtggcgatgatcctggaggatgcgcagccagcctgcgttatcaccactga
ggaagtggcgggcaacctgccggatgccaccgacaacctgatcttcctcgacaagccctcgagcgacagggacgcg
acctgccgaaggggccatcgctgagcgacacggcctatatcatcttcacgtccggttcgaccggtcggcccaagggc
gtggaaattccacatcgcggcctgatgaacttcctgttgtcgatgcaggatctgttgaaactggacagcgaagaccg
gttgctggctgtgacgacgatttccttcgatattgcagcacttgagctttatctgcccttgctggcaggcgcgcgca
cggtgatcgcgctgcgctcggaagtgcgcgaccgggcggtgctgcatgggttgatccgcagtgcgggtatcaccatc
atgcaggcgacgccgtctttgtgcgggccttgctggccgatcatcatgagggactgacgggcttgcgcagtcttgt
cggtggtgaggcgcttcccgccgatctcgcccataagatggcgcggctcggccacccggttctcaatgtctacggac
cgacggaaaccacgatctggtccaccaacatgccgcttttgggcagcgacctcgacagtgcgccaattggccggcca
atctggaacaccgcgtttatgtcctcgatcggcattgccagccagtgccgcccggcttatcggtgagctgtatat
cggtggtgcgggcgtggcgaagggctacctgaaccgcccggacctgacggcgaaaaattcatggctgatcctttcg
caggcgaaggcgagcggatctaccggaccggcgacctggtgcgctggcggcgcgatggcgtgctggattatctcggc
cgcaacgaccaccagatcaagattcgtggattccgggtggagccgggcgaaatcgaggcggcgctttccgccctgcc
gcaggtgcgtgaagcggtggttattctgcgcgatgatccggcgcgcgaaaagcgactggttgcctatgttgtcccca
gagagggtgcggtaggcgaggggtgcctcgctggatgctgctgatccttcggagcggctaggcaaggttctgcccgtt
cacatgatcccggcggcctatgtggtgctggacgctattccgttgaattccaatggcaagaccgaccggcacgcgct
gccggtaccgcaatggacggtgacggaaggcatagccctgccggggaccgatgctgaaaagcggcttgccgccttgt
ggtgcgagatccttggtctggagcagatcggcattcacgacagtttcttcgtgctgggtggtgactcgctggctgcc
gctggaatgatttccgccgttcgcagccgattgaagggcgaaattcccctcggtgccgtgttcgaaacaccaaccat
tgccgccttggccgtgcatctggatgaggcaagctcgggttcaccactgattgaaccggttctggccatccgcgcca
agggcgagcgcccgccgctgttctgcatccatccggtgctgggcttgggctggagcttcttctcgctcgcacaacat
tgagcgaggatgtcccggtttacgccctgcaatcgacgccggttgcatgacctcgccgccctgccg
cgctctatcgaggatatgctgcgctctatgtgcagcggattcgcaagatccagccgcagggcccatatcatctgct
gggctggtcattgggcgggctgattgcccatgaaatgaccggcaattgcaggcagaaggccaggctatcgcgttcc
tgggcatgatggacagctaccatttcaaacctgctgcccaattgcaggacgatgcgacgctggcgcgggccgccctc
ggtttcctcggctttgatgaaaaggcagcgggcgacaagccatcgctggccgagcttggcgatttcgtgctgaaaat
gttcgatacggacaaccatgcctgctggaacaggttcaccagttcgatcccgagttcgtcgagcgcgccaaggcaa
ccatccttcacaatctggagattgcccagcgctttacaccgggcaagatcgatgccgatgtgcatttcttccgcgcc
gaaccaagtgcgggcagcgatgcgctgaacaccatcctcaactacgatgcggaaacctggttgccgcatgtggaggg
caggggtttacctgcgcgacatgacctgcaaccaccacgacatgctgaatatcgaaccggcatcccatatcagcgcg
tcgttcaagcagagttgctgcgtgaattcctggtcctgcgtcggccccagactgaggtcaagattgagcgtgtgtcg
cggtttg
cctaa (SEQ ID NO:11)

Amino acid sequence:

MSFVGRHEQVFPVSLAQAGLWVKQKVAPADLSFVLAESIEIHGPVHPGLFCQALRRLSDDVAVTRSRIKEIEGQPHQ
VVMAAYCGVFDVIDFSGADNPGASAMDWMRKQMSKPLDLANDNLWGSSLLKLGATEWVWYHWAHHIIMDGFSGGLLA

FIG. 6D

```
RRLADIYSALAQGNQPEPYDCGSPQELLELERTYRDSVHFQRDKAYWSEQMKGLPEPVTLMKKKGEPSGGLLRHTTV
IDRQTVKALAEISRGFGASVPQALIALVAAYYAKATDCEELTMVTMVTARISQTMRRIPGMTANAVPLRFSITPDLS
WRELTGQVSQQMSRALRYQRYRYEDIRRDLGMVRQDAQIAWLGVNIEPFDYDLRFDGQPTTVHNLSNGTMTDFTIFA
YDRGDNGDLRIDFDANPALYTLEELADHEARFTRMLREILATPEQPLRDFSLLSKWERQEILTDWNDTSHKLPDQTW
PELFRAQAARTPDAVALSFGGRQMTYGELDAASDHLAGYLMEKGAVPGSLVAVAVPRSENMVVALLAVLKSGAAYLP
LDPADPASRVAMILEDAQPACVITTEEVAGNLPDATDNLIFLDKPLERQGRDLPKGPSLSDTAYIIFTSGSTGRPKG
VEIPHRGLMNFLLSMQDLLKLDSEDRLLAVTTISFDIAALELYLPLLAGARTVIALRSEVRDPAVLHGLIRSAGITI
MQATPSLWRALLADHHEGLTGLRSLVGGEALPADLAHKMARLGHPVLNVYGPTETTIWSTNMPLLGSDLDSAPIGRP
IWNTRVYVLDRHCQPVPPGFIGELYIGGAGVAKGYLNRPDLTAEKFMADPFAGEGERIYRTGDLVRWRRDGVLDYLG
RNDHQIKIRGFRVEPGEIEAALSALPQVREAVVILRDDPGREKRLVAYVVPREGAVGEGASLDAADLSERLGKVLPV
HMIPAAYVVLDAIPLNSNGKTDRHALPVPQWTVTEGIALPGTDAEKRLAALWCEILGLEQIGIHDSFFVLGGDSLAA
AGMISAVRSRLKGEIPLGAVFETPTIAALAVHLDEASSGSPLIEPVLAIRAKGERPPLFCIHPVLGLGWSFFSLAQH
LSEDVPVYALQSDGLHDLAALPRSIEDMAALYVQRIRKIQPQGPYHLLGWSLGGLIAHEMTRQLQAEGQAIAFLGMM
DSYHFKPAAQLQDDATLARAALGFLGFDEKAAGDKPSLAELGDFVLKMFDTDNHVLLEQVHQFDPEFVERAKATILH
NLEIAQRFTPGKIDADVHFFRAEPSAGSDALNTILNYDAETWLPHVEGRVYLRDMTCNHHDMLNIEPASHISAVVQA
ELLREFLVLRRPQTEVKIERVSRFA (SEQ ID NO: 12)
```

**F-avi4330 (avi4330 in *A. vitis* F2/5) encoding polyketide synthase**

DNA sequence:

```
ttgtttgatcttttgcgtgccggcgcatgcactgtctcgaccttgcccggggatcgttgggatattgcgcgctactg
gcatcccgaaatcggcacgcctggcaaatattacaccttcgctgccggtgtgatggatggaatctatcagttcgatc
ccgccctgttcggcatgtcacggcgtgaagccgcctttatggacccgcagcagcgcatcctgctggagttgacctgg
cgggcgctggaagatgccaatatccccgccaatagtctgtccggccagaatgtcgcggtctatgtcggtgcctccag
tttcgaccatgccaatctggccggcgaagatccggctggtcccggtccgcatttcatgaccggcaatacgctatcgg
tggctctccaaccgtatctctcatgtcttcggcctgaatgtccgagcatgacggtcgatacggcctgctcgtcctcg
ctggtcgcactcgatcacgcggtgcgcgcgattgcgtctggcgaggttgacaccgccattgttgccggtgtcaacgt
tctggtccatccgctgcctttcgttggctttgcgcaggcgcgcatgctgtcgatcgacggttttgtgcaaggcctatg
ccaatgacggtatcgggtatgttcgggccgaaggcggtgccgtgctggtgctgcgatctagcgataagcccggcgc
gaaggcgaccgcagccacgcgactattgttgccagcggcaccaatgcagccgggcgcaccaacggtatttcgctgcc
gtcgcgcgaggcgcaggccgttctgttgcgcgcgtctatgacgacaatggtctcgacccggatcggctggccttta
tcgaaggccatggcaccggcaccaaggtcggcgatccgccgaagtctggtcgcttggcacggtcatcggccagcgt
cgcaaggaacctgtgtggatcggctcgatcaaaaccaatatcggtcataccgaaccccgcatccggcctgcttggcgt
gatgaaggcgatgatgccttcgcagcacgaccctgcttccggcctcgctgcattcaatgagccgaatgacacgattg
atttcgatggcctgaatgtccgggttgcctcgcaggccgttcactggcacgcgatggtgcgccgcgccttgccgga
atcaactccttggctttggcggcgccaatgcacatgtggtgattgccgatccgcagagacctgatttggtgcctgg
tttggcgcaagacgcggctaatccagccggtgccggtcgcttgttcatggccagcgcccactctcaggaaagcctga
aagcgttgctggacagttacgacaaggcctttgcggccgctggaagcgatggtgatctggaagacctgatctcggcg
gccgcctccaaccgtgcgccgctccggcaccgtttcgttgccagtggcagcgcggatgccatcgtcaaggcagtgca
ggaacggcttgccacagcgaagaccggcggcgaaaccggcgaagccttgtcgcgcaacggcaagctcgccttcgtgt
tttctggcaatgcgcccaatgggcgggcatgggtcttgatgcctaccgggcaaacgcccgcttccgcgagagctat
gagcggatcgccacgctctttacggcgcattcggacccttgacctcgttgcggccttgaccgatccggatctggaagc
ccgattgaaagataccaggcttgcccagcctatgctgtttgccatccaggcctcgctgtcggatcgctgcaacttg
ccggtctggtgccggatgctgtttacggtcattcggtcggtgaagtggctgccgcctatgtatcgggtgcgctgtcg
ctgaaggatgccgtctgtgtcatcgccaaacggtcgcagcatcaggcggtgttggccggtgaaggcacgatggcggc
cctgaagcttggcgaggccgatgcgcgcgccatgctggccgagcttggctttgatgacctgacgattgccgcgatca
atgcgcccaattcggtgaccgtgtctggtcgtgaagacgcgatccgggcgctgagggaacatgcccgcaagcagcgg
gtgccagcccaggtgctggacattgactatcccttccatcatccgctgatcgataaggcgaaggctgccttttccgc
cgatccgccgctgattacccccgcgccagaccaccctcacattcatctccacggtgacgggtgagcaactggagggca
ccgcactgacttcggattactggtgaagaatgtccgccagcgtgcagttccaaggggcgacggaagcggccatc
gcgcttggttgcaccgtgttcgttgaaatttctccgcgtgcgatccttggcggctatgtgtcggaaacggcgcagca
tgtgtcttcgacggttgccgtcagtgccagccttagccgtgaggctccggatgagacggtcgatccggtggcgcggg
ctttggcgcgtgctgtcgccagcggcgccaaggtggatgaggccaaggtcttcggtccggccgcgccgatatcgtc
ctgccgggcgtgcctttcgagcgggccgatctgcgaccggagccgaccagtgaccgcgtcgatctctatggccggtt
cggccagacggcctatcggttgagcggctggcgggtcgatttgaatggcgggcattggaaaaccatctcgacgcgc
acctgtttccggatctggccgaacatgtggtcgatggccgggccattttgccgggcagcggttttgtggaaattgcc
atttcggcgcgcgacagcatttcggcctccgaccagctcgagatcagcaatgtcgagatcatgcgaccgctggaatt
gagcgacagccggatcgtcgaactttccacgctgatttccgcgaccggcgatcttcagatccgctcgcgcgagc
ggctgagcgatgacgactggacggttgaatgcggttgcccgggttcgcaagctcacggcctccgaactggacgatgcc
gtggatttcgacctgtccagcccgacatcagagctggataaatctgccgcctatcggacggcgcgcaatttcggcct
ggattatgggccgcgcttccaattgctggaaaaggcgatctgccatggcgagcggcttgtcgaagtgttcctgaagc
cggcagccgcgccgggtcacccgttgctgcgctataatctcaacccgatgtcggttgatgcgatgttccacgggttg
```

FIG. 6E

```
gtggcgctgtttggccgcttcagcggcgagcagggtggtgcgccttatattcccgtgcgtttcggacgtgtccgcac
atgggttctcggtagcccggtccatcgggcggtgatcgagatcgaacggatcagcgacagctcgatcaaggccaatt
ttcatctctatggtgagacgggcgagcggatcgccagcttgagcgatagccggttccgacgcacctatctgaagcag
cacaagacgctcgatggacttgcctatcattatgaaaccatcgcgctacccctggtgaaagatcagggtgcggccct
ggttgcaccgttgggtgatgttttcgcatgtcaggaacgtgagctggacaatgccacggtgctgatccaggcctgcg
tgctcagcgccttctatgcgctggccgagtgccttgccggtcaagatcggcgcgtgtcgctggtcgatctgccgggc
gatgtgcggttgcggcggttcctgaccaatgccctgcacagtctgaccgatagcggctttgcccagtatgcggatgg
cagctggacgcttgaagatgcagcgatcttccgcccgcttcgagctgatcccggaactctatcgggatttcccgg
aacgcaccgttgaactggtgatgatcaatgacgtgctgacagccgttaatgcagcgctcaatcagcctgcaggtgtt
gtggacgagggtttggattgggacggggtgatcagcgaagcgacgctggaccatttcgccgttcattccacgctcgc
caccgagagtcataggggtgttgttgaaggctgtgatcgactgtctctcgaccttggatgccgatgcgccgccgctgg
tggtcgagcttggcgccagctcgcttcacttagccgcaagctcgccgatctggttcgtgcggctggcggcaatctg
gtgatttacgagcctgaggcaggcctgcgccgcaatctggagctgtctttcgaggctgatccgcgcgtcactgtcgt
ggacgcaaagggattggaccagctttcgcttttgaaagcgccggtcgatctaattgccagcgcccatgccgatctttt
gccgcttgctggatggtgaaatgctggcacggctcagccatggcgccttggcctcggccgtcgccttgtcgccgtg
caaccagcgccccggcctattgcatgatttcgccttcggtctgctggatggttggttcgacaggacggttcggagga
atttccgctcggccgatttggcggtagcgaagactggatgaaatccctgcaacaggccggttttgcggcggcccatg
cccggcaattgcaggtggatggcggtagccttatcgtggcggaagcccagggtcgggctgacgtggccgagccatat
gatgcgacgcgtcaggacggtgggtcggtggatgaggttgtggccagcgggccagtgatcatcgttcatgaaaaac
tgcggatcttgcccggcttttcggcggcagcaagagcgcttggtggttcccaggtgtctttgctgtgcctgtcaggca
gctttgaaacggaccggtcgatgctggccgatgcactgggcaaggctggaccagccgtgggcggaatggtctggctg
atgccggataccgatgcggctgcggatggatcgctgctgttgcaggacagggtcggcgctcttagcgcgctggccat
ggcgtttggcgatgttgcggcatcaacgtctgatgctgcgaggacgcttccggtcactctggttctgcccggcggtg
cgcccgtcaccggctttaccgcaaggacttgaccgctccagtcatgcgggcctgtcaatgcaggtctctgggcc
tttgcccgcgtattgcgcaatgagttcgacctgttcgacatgcaggtcgtcgataccggaccctccagcaatacgct
ggaaatcatgctggactggggcatgcgcctgctggccgccaagggcgacaaccgcgaatggctggtggagccggaaa
ccgggcggatggccgagattcgtgccgtgcctggtccggccccgctgacggcgcagcgtaccgttgcttttgaggca
gcggtcattcgccagcaggtgccgtcgcaggtcgccagcatccgctgggaaagctgcccggtcccagtcatcggtcc
aaccgaagtgctggtgaagaccgcagcgacaggcttgaatttccgcgacgtgatgtgggccatgggcctgctgccgg
aagaagcgcttgaggacggctttgccggggcctccatcggcatggaatttgccggtgaagtggtcgctgttggcggc
aaggtgagcgatcttgccctcggggacaaggtgatggcaatcgccgctcggcttcggcaccccatgtcaaggttga
gcgggctggggtggcgaagctgccgatggcgtggaccggtatcggcgacgaccattccggtggtcttcctgaccg
cctattatgccatccatgagcttgggcgggtacgtccgggcgaaaccatccttattcacggtgccgctgcggcgtc
gggcttgcggctttgcaggtcgcccggcatttcggcgccaagatcattgccacggcaggcaccgtcgaaaagcggcg
cttcctggaaacgctggggcggaccatgtgttcgatagccgctcgctcggttttgtcggcgatgtgcttgacgtga
ccggcggcgaaggtgtcgatctggtgttgaactcgctgtttggcgaggcgatgaaaaatccctgtcgctggttaag
ccgttcgggcgtttccttgagcttggcaagcgcgattattacgccgacagcaagatcggcctgcggccattccggcg
caatgtcagttatttcggcattgatgccgaccaattgctggtcctgcatcccgatctgtcgcgccgtatgctggccg
aaatcggtggcttgttcgagcagggcgtgttcacgccattgccgttccgcgccttcgaacacgatgagattggtgat
gccttccgcctgatgcagaatgccggccatatcggcaagatcgttgtcctgccccgggttgcggggccgtgaccgcgt
cgcggtaaagtctgcgccgatggtggtcgatgcggatgtatgcatctggttgtcggcggtatcggggtttcg
gccttgccgcagccgattgctggtagagcagggcgctcgccatatcgccttatcgacgcggcgcgggctggttgat
gcggagacgcagaccgtggttgaccgctgggccaagcaggggcgtgacggcctatattcgcggctgcgacgtgaccag
tgaagcggccttgtcggcgcttttgacggagcttcgcgccattgcgccgttgaagaccgttatccatgcggcaatgg
tgctggacgatgccttcatctccaatttgacgcgggcgcgaaaccagccggtgatcgacgtcaaggccaagggtgct
gtacttcttgaccggttgacccggcaggacgggatcgacaatttcattctgttttcgtcgatcaccaccctatgtcgg
caatcccggtcagggcaattatgtcgctgccaacggcttcctggaaggcttggcgcggggcgtcgcgccgatggtc
tggctggtcttgccatcgcttcgggggcaatcggcgatgcgggttatctggcccgtaatgcgcaggttaatgaacgg
cttggacgccggatcgcaagacggcgctggatgccgcgatgcgtttcggcggtcggcgctatattgctgccga
taccggctctgtcgatgcagctgtggtgatgatttccgaattcgactgggctgctgcacattcgctttccgtggtca
acgaaccgctgttttcgttgatcatgcgccgcagcaaccagcatgccggtggcagtgagggtggcgagatcgatctg
gtggcgctgattgatggcaaggcgccggctgcggcgcaggacgtgctgtttacggtgcttgccggtgaaattgccga
tacgctgcgggtgcccaaggaaagcatcgggctgaacagcgtgctgaaggacatcgggctggacagtttgatggctg
tcgaactggggatgaatttcgagcagaataccggctttgacattcccctcagcagccttgccgacaacgccactgtc
ggagacctgacgcgacgcctctatgaaaagtcagcctgcgcggacggacaggcgaca
aggatgaagcgctacctgaggacagcaagatcatggacgatctgcatcgtcgccacagcgggcaggaccagtaa
(SEQ ID NO: 13)
```

Amino acid sequence:

MFDLLRAGACTVSTLPGDRWDIARYWHPEIGTPGKYYTFAAGVMDGIYQFDPALFGMSRREAAFMDPQQRILLELTW
RALEDANIPANSLSGQNVAVYVGASSFDHANLAAEDPAGPGPHFMTGNTLSVVSNRISHVFGLNGPSMTVDTACSSS
LVALDHAVRAIASGEVDTAIVAGVNVLVHPLPFVGFAQARMLSIDGLCKAYANDGIGYVRAEGGAVLVLRSSDKARR

FIG. 6F

EGDRSHATIVASGTNAAGRTNGISLPSREAQAVLLRAVYDDNGLDPDRLAFIEGHGTGTKVGDPAEVWSLGTVIGQR
RKEPVWIGSIKTNIGHTEPASGLLGVMKAMMALQHDLLPASLHFNEPNDTIDFDGLNVRVASQAVALARDGAPRLAG
INSFGFGGANAHVVIADPQRPDLVPGLAQDAANPAGAGRLFMASAHSQESLKALLDSYDKAFAAAGSDGDLEDLISA
AASNRAPLRHRFVASGSADAIVKAVQERLATAKTGGETGEALSRNGKLAFVFSGNGAQWAGMGLDAYRANARFRESY
ERIATLFTAHSDLDLVAALTDPDLEARLKDTRLAQPMLFAIQASLSDALQLAGLVPDAVYGHSVGEVAAAYVSGALS
LKDAVCVIAKRSQHQAVLAGEGTMAALKLGEADARAMLAELGFDDLTIAAINAPNSVTVSGREDAIRALREHARKQR
VPAQVLDIDYPFHHPLIDKAKAAFSADPPLITPRQTTLPFISTVTGEQLEGTALTSDYWWKNVRQPVQFQGATEAAI
ALGCTVFVEISPRAILGGYVSETAQHVSSTVAVSASLSREAPDETVDPVARALARAVASGAKVDEAKVFGPRRADIV
LPGVPFERADLRPEPTSDRVDLYGRFGQTAYRLSGWRVDLNGGHWKNHLDAHLFPDLAEHVVDGRAILPGSGFVEIA
ISAAQAHFGSDQLEISNVEIMRPLELSDSRIVELSTLISAATGDLQIRSRERLSDDDWTVNAVARVRKLTASELDDA
VDFDLSSPTSELDKSAAYRTARNFGLDYGPRFQLLEKAICHGERLVEVFLKPAAAPGHPLLRYNLNPMSVDAMFHGL
VALFGRFSGEQGGAPYIPVRFGRVRTWVLGSPVHRAVIEIERISDSSIKANFHLYGETGERIASLSDSRFRRTYLKQ
HKTLDGLAYHYETIALPLVKDQGAALVAPLGDVFACQERELDNATVLIQACVLSAFYALAECLAGQDRRVSLVDLPG
DVRLRRFLTNALHSLTDSGFAQYADGSWTLEDGSDLPPAFELIRELYRDFPERTVELVMINDVLTAVNAALNQPAGV
VDEGLDWDGVISEATLDHFAVHSTLATESHRVLLKAVIDCLSTLDADAPPLVVELGASSLHLSRKLADLVRAAGGNL
VIYEPEAGLRRNLELSFEADPRVTVVDAKGLDQLSLLKAFVDLIASAHADLCRLLDGEMLARLSHGALASARRLVAV
QPAPGLLHDFAFGLLDGWFDRTVSEEFPLGRFGGSEDWMKSLQQAGFAAAHARQLQVDGGSLIVAEAQGRADVAEFY
DATRQDGGSVDEVVASGPVIIVHEKTADLARLSAAARALGGSQVSLLCLSGSFETDRSMLADALGKAGPAVGGMVWL
MPDTDAAADGSLLLQDRVGALSALAMAFGDVAASTSDAARTLPVTLVLPGGAPVTGFTGKDLTRSSHAGPVNAGLWA
FARVLRNEFDLFDMQVVDTGPSSNTLEIMLDWGMRLLAAKGDNREWLVEPETGRMAEIRAVPGPAPLTAQRTVAFEA
AVIRQQVPSQVASIRWESCPVPVIGPTEVLVKTAATGLNFRDVMWAMGLLPEEALEDGFAGASIGMEFAGEVVAVGG
KVSDLALGDKVMAIAAAAFGTHVKVERAGVAKLPDGVDPVSAATIPVVFLTAYYAIHELGRVRPGETILIHGAAGGV
GLAALQVARHFGAKIIATAGTVEKRRFLETLGADHVFDSRSLGFVGDVLDVTGGEGVDLVLNSLFGEAMEKSLSLVK
PFGRFLELGKRDYYADSKIGLRPFRRNVSYFGIDADQLLVLHPDLSRRMLAEIGGLFEQGVFTPLPFRAFEHDEIGD
AFRLMQNAGHIGKIVVLPPVAGRDRVAVKSARRMVVDADGMHLVVGGIGGFGLAAADWLVEQGARHIALSTRRGLVD
AETQTVVDRWAKQGVTAYIRGCDVTSEAALSALLTELRAIAPLKTVIHAAMVLDDAFISNLTRARNQPVIDVKAKGA
VLLDRLTRQDGIDNFILFSSITTYVGNPGQGNYVAANGFLEGLARARRADGLAGLAIGFGAIGDAGYIARNAQVNER
LGRRIGKTALDARDALSAVGRYIAADTGSVDAAVVMISEFDWAAAHSLSVVNEPLFSLIMRRSNQHAGGSEGGEIDL
VALIDGKAPAAAQDVLFTVLAGEIADTLRVPKESIGLNSVLKDIGLDSLMAVELGMNFEQNTGFDIPLSSLADNATV
GDLTRRLYEKVSLRGRTGDKDEALPEDSKIMDDLHRRHSGQDQ (SEQ ID NO: 14)

DNA sequence of Avs locus (ORF P1388 to P1397)

1-
GTCGCCATGACCCAGCGATAAATCGTGGAATGGTCAACCGCGACGCCCCTTTCAGCCATCATCTGTTCAAGATCGCG
GTAGCTCACCCCATAGCGGCAATACCAGCGAACTGCCCACAAGATCACCTCGCCCTGAAAATGACGCCACTTGAAAT
CGCTCATCAAAAGTCTCGCTGAAAACTATCTCCCTTATTTCCAGCACAAACGGAATCTTTGCGACAGAGCCGTATTT
CCGGCCTTTGATGGTTACCACCATCTCATCGAGGTGCCATTTATCGGCAAAGCCGCCCTTTGAGCGCCGGCGAAGCA
ACGCAGCAAACTCGGAGCCAAATTTGGCGGCCCATTCCGATACTGTCTGGAACGAAACGTCAATACCGCGTTCGGCC
AGCAAATCCTCGACATGCCGCAGGCTCAATGGAAACCGGAAGTACAGCCAAACCGCGTGAGCGATAATCTCGGCTGG
AAAGCGGTGACGTTTGTAACGATAGGAGGCGAAGGTAGACGAAGAAATGTTCATGCCCACTGCTCTATCGTACAAAA
CTTAAGGCGAAACTGCCGCTCAGGGCGCAAGGCTTATACTATAGCCTGACTTGTATTCGATTGGCAGAAAAAGGCGA
TGATATTCCCTGAATGTCTCGTCTGGATCGAGATCGGCGAACAAATCCGGATGAAGCCATTTTGCGATTTGTTGTAT
GGCGATGAATTCATAAGGGCTATTGTAGAACTGATGCCATATGCCATGGAAACTGCGGTTTTTGACCGCTTTGGTGC
CAATATAGGCATTTCTTGTCGTGAACCATTCCAGTTTTCGTTCGCCTTCCTGTCTGTTGGCACCCGGCCCCAGGGGT
ATCCAGTGTCCACCCGGAACATAAGCTTCCCAATTGGCGCTCGTGACCACAACCTGATCCGGGTCGGCAGCAATCAC
CTGTTCCGGGTTCAATTGTCCGAAGGTTCCGGGAAGAAAATCACCGCCGATATTGTGCCCGCCGGCGATTTCGACAT
AGCGACCAAAATTCTCATTGCCAAAGGTGAGGCAGCAATCATCCGCATAACCGCCAATCCGCTCGACAAAGACATTC
GGTCGTGCGGGCTTTTTTGTTCAATCACATCCGTCACTTGCGACAATGCCTTTTTCCTGAAGGCAATAATTTCCTC
GGCGCGCTTTTCACGTCCCATGATCTCGCCCAAAAGGCGGATTGTTGGTTCGGTATTGTGAAGGGGTTGATGCCGGA
AATCGATATAAAGAACCGGTATTCCAGTGATGCCAGCTTTTCGATATATTCGGACTCTTTGCTGGCACGCTGGGTT
TCGAGATTCAAAAGCACAACATCAGGCTTTTGAACAATGGCAGACTCAAGATCAATCAGACCTGCTTCCTTGCCGCC
AAAGGTTGGCAGTTGGGCCAGTTTCGGAAACTTCGCGACATATTGGGCATAGGTTGCGGGGTCGGCTTCAATGAGGT
CATTTTTCCATCCTGCCAGAAACGCCAGAGGATTCTCGGACTCCAATGACGCGACAAGATAGAGCTGCCGCCCTTCG
CCCAACAACATGCCGATGGACAGGAACAGGCAATGACACCTGCCGACCAGCAATGTCTGTCACGGTGATGCGATGCGG
CGTTGTTGCTGCATTGGATGTTTGAGCCGCCTGGCTCCCTGTGCCACAGCAGATGGCATCTGCGCGACAAGACACGACA
GCAGAGCCGCAAAGAGTGGTTGGCTGGTTTTATCACCGTTTTATCCTATGCGGTTGGGTAAGGGCCGCTTTTGAG
CAAGAGCGACAGGCCGATAAAAAATGACAGGATGTAACACGCCGATACCAGGGAAAATGCGGTATCAGCACCCCAAA
GCTGCATGGACCCAACACCGGCTGCTATACCCAGAATGGAAGCGATTTGCTGCCAGCTTTGCGCACGGCCCAAAATT
TCACCTTGCCGATTGAAGGCTGTGGACTGGGAAAGACGCGAGGTAAGAACCGGTGTCGTACCACCAAGCAGAATGCC
CCAGACAAAGTATAATCCTGCAAAAACGGGAACGAGGGTTGTGTAGCCCGCTATCAAAGCGATGCTTGCGCAGGCCA
GAGCGATCGCGGTGTTTGCCGCCAACACAAAGCCAAGGCTGCGCATTTTGAACAGACGCGCCCAGAGGGGGCGCCA

FIG. 6G

```
ATCACAAAACCAAACGCCATGAGCCCGTAGCTGAGGCCAATAATCCAGTGGTTGGCTCCGAAAGCTTGGGTCATGTA
GAGCGAAAACGGCACTTGCAGCACCATTCGGCTGGCCAACAATACGCAAATCAAAACCAGCAACCCGACGACTGGTG
CAGAACTTTCTGGATGGCCCGGGGTGAGCGCGCTTGAAGCGGAGCGCGGTGCATTCTGTCTGATGGGCGGGATGGGC
AATGTTGCCCAGGCAACAAGGGCACATAGACCACATACGGCCCCGGCCGTGATATTAACGGCCGCGAATGGCATTGC
ATCCAGAATGAGACCACCCGCAAATGCGCCGCCCAGCGAACCGACATTGGTCGCCACCTGCAACCAGGCGAACAGAC
TGGCGCGATCACGCCCGCTATTGACCTGCACGGCATAGGCTTGCGCGGGCGCAATATAGCCGGCGAAAGCCCCCTGT
AAGAACCGCAGAAACAGGATGACCCAGACATCTTGGGCAAGCGCAATCAGAAGCTGGGTGATCGCCAACCCCGCCAA
GGCCCGAACCATCATCAAGCGATTGCCATAGCGGTCACCCATACGCCCCCAGAATGCGCTGGTGAGGGAAATGCCAA
GCATGGGCAAATATAAACCCCGATACTTGCCAATCGAACGCCGTATCCGACGGGCTGAGTACCCTGATCTGCAGC
GGCCAGAAAGGACCGCTCATTTCCATGGCTCCCATGGAAATGAACTGGAGCGCAAACAGCAGCAGAAACACAGGCGT
GCTTGCCCTGAGCATGGCAAAAGCGTTCAGCATTCACGGCCAACCAGAGGATTGGGCAGCTCATGCTCCACCCGATA
GTCGCTATATCGCTGGAGATGCATGGTGAGAACCGACCGGGTGGGCCATTTTTTTTCAAGCAGGGCATCTCGTTCTT
CTTGCCAGAACGTGTCCGAAGACACACGAGGCCGCAATGTTTCAAACGCCTCTTGCGTTACCTCTTTGATCACTGTC
CAGAGCCTATCATTGCCGATACTATAGTGCTGGGTCAGGCACAGAGCAATTTCATGCAGATGGCATATAAAGCAGGC
GTCGATCAAAAACGAGCGAACCAGCCCAATGTCATCGTCAAAGGTGGTGGGCAAAATCCCAGCACGCTGAAAGGGTT
TGAGGTGATAGCCACGCTGTTTGAGCAGAGGCGCAAAGCTGCGGCCATCACCAAAATCCCGAATGATCAGCTTTTCC
GCAGAACCGGAAGGATCAAACACGATGGTGGTGTTTTGCTGATGGGCCTCAAAAGCGATGCCATAAAGAAGATACAT
CGCCAACGCAGGCCGAACCACCACCTCAACATACCGGCGGAAAAAGCCGACAACGCTTGCCTGTTCCTCATTGCCGT
AACGGGCAATCAGCTCGCAGATCAATGGTCGTCCATCCTTGGGACTTGCACTTAGAAGTGCGGCGACCGTCACCGCA
TAGCGTCCATCCTCGCGCTTTAAAGGCTGGGCGTTGCGATAGACCACCGACAAAAATCGCCCGCGATGCTCATCGCC
GGTATCGGGATCGTGCAGAATGGCTCCCAATTCTTCGGTGAAGATTTCCAATTGTGCGGCCATGTCCGGTTCATTGG
CCAGAATATCGGTGATCAACGTGGAAAGCCGAGGCCCCATGTGAATGGATTTGGCCTGCAAGCTGCGCTGCTCGCTG
GTGAGCCAGATGGCAACCGGCAACTTGATGAAAGGGCGCAACGTTTCATCGTCCGGTAACATGGTCCGAAATGACAT
GGATGGCGAGGTGTCAATGTCTGGCCCGTCCAACAGCAAGATGCCAGAGGCGATTTCCTGTCCAAATTCGCGGCGGA
CAAAATGCTCGAGGTGCCATCCGTGGATGGGCAAAGGAATCCAGTCTTGCGCTGATTTGCCCTGTGCGCTCAGATGG
TCTTTCCACGCGGCAAACAATTCGGGAAACTGGGCAGAAAACCAGTCATTGTAATCAGTCACATGTGGCATTTTTTC
CACATAGGCCCAACCCCGACGCAAGGCCGCAATCCGGACCGGCACCTTGGCCCCGAATTCAGGCGGAAAGGGCAACAA
CCTCTTCGGCTGCAAACTCGGTTTTGCCTTCCATGTCGGATAAAACGGATGACCTTCGAGCGCACCCCACTGGTCA
ATCAGCATTGCCGCCAGATGTGCAGGCAAATGACCGTAGAGATAGCCCAGAAAATCCACCGCACCGGATTGTTTGAT
CTTCTCATTCAGGCTCGCAGCCCAGACCTGCCGGTGTCGGCGGGCCAGCATATCATTGTTGATGCTGTCGGCGATAT
CGCGCATCAAAACCTCAAGCCCATCAGGGGCCGGAGAGATGGACAACGAAGCGAACACTTCCCGCAGCAAAGCATCG
GGATGGTCAATCCGGGCATGGCCGCCGTCGGCGTCGAGAATTTCAATCTCGCCACGGTTTTGCAAGGTGCCAGCGGG
TGCCGCATGCAAATGTTTAAAATGCAGCACACGGCGCGTGTTCCACAGCCGCAACCAGGCTTGATGCTTGTCACGCG
ACCAGAGCAACGCTTCAGGAGCCAGAAGACGTTCTGCAAACAGGCAGCGAACAAGGCGACTGATTGCATTGGCAACG
GCAAAATCCCGCAACGGCTGGTCATCGGTCTGCGCATGGATGTCAAACAAAGGCGAAAGCAAATGGGTCATCAGGCA
GCCTCCAGCCAATCATCAGGAACCGGGCTTAATCCATCCGGCAAAGCACCATGATAGTGGCGCGCCCACGTGTAGGT
TTTCGAGATGGTTGGAATCGGTACCGCCAGCCGCTCTGCGATCTTGACCAGCAATGCCTGCCCGCATGCAACATCCT
CATGAAAGGCACGGCTTTGCAGATCGATCAACCAGCCTTGACCATGATGATTGGGGATCAGCGGCAATTGAATTCCC
GCATAGGCGCTGTTTGTTCTGAGCAGGGAATACATCGTTTGACTATCGGCAATCTGATCGCCATAGGCTTCAATCAG
TTCCTGCCGCAAAGGTTTGACGGAGCTGAGATCAAGACCGGTTCGGGTCGCAATCGCCTGACATATGGCCTGATTTT
CGGCATCGAACATTTCGAGCAAGCGCGCGCCCTTCCTCAGGGCAATCACTCCACCAGCACAGCGGCTCGGAGAACGGT
TTACGCTCCCAGGGAGCGCCCGGCCCCAGCAGGCCGTAGAGCACCGCTGGATGCATCAGCGCATTGCCGGGTGTCAG
GGTGATTTCCAGATAGTCCTGCAAAAGGGTTACAGGCGCATTGTAAAGTGCGGTCAGCATTGTTTGCAGAGCCTTGG
CACTTTGGGCGGATTCCCGCCGATGAAGGCCAGCAAACAAATGGGCTTTAGCGCCGCCCATGCGAACGCTCTGTCCG
GCAACAAGGTCGTAGGCGATATGCGGCACATCCTTCAAACCCCAGATGACCACATTATCCCTTGCGCCTAAGTGATC
GGCAGCCAGCCAGTCAAAACCGCAAAAGCCCGGAATAGCACCCACGAAAACCTGCTTGGTGCTGGAGATACTGCCTG
CGATCCGCTGCAAAACAGCGGATCTGGCATGGGCTGGCTGGGTAATGACAATCAGATCAGCGTTCCCAACCGCTTTA
TCGGGGTTGTTGCCAACGTAATCAGGACGCCCGGACATACCCTGACCATCCGGCAAAAAGCCTGCCATGGAGCAGG
ATTTCCAGCCCAATTGGCGGCAAGAGTGTCATTCTCCGTCAAAACGGAGAGATGGACCTGCGGATTTTGCTTAAAAA
GCACGGCATTCAAATGCCCGGTGCGGCCTGCGCCGCAAATGGCGACCCTCATCCGCACCTGCCAAGCCATTGAACC
AACCATCCAATTGAGCTGCGATTGCCGGATTGAGAAGCCCGCTTTTCCATCCACTCATCGTCAAACACGGATGCC
AGGTATTTTCACCCCCATCTGCGACGGCTGTAACAATTGTGCCGCTCAATTTACCGGATGCGATGAATTCGAGAGC
TTTGTAAATTGTACCCCGGTTGATCCACCAACGAGAATACCTTTGCGTCGGGCAATATAGCGTGCCGTTTCAAATG
CTTGCGTATCGGTGACCTGAACACCTTCATCAATGCAGCTATAATCCAGAACCTTGCCGACTTCATCGCCTGCGGGC
GTACCTGTGCCAGATTGGTAATAGGAATGCCCCGGCTTACCAAAAACAATGGAACCAGCAGGCTCAACCGCAATTGT
CTTGATGGCGGGATTGAGGCGCTTGAGGCGCTGGGATATGCCCGTCATCGACCCACCCGTACCCACGCAACCAACAA
AGGCATCCAATCCATCAGGCAGTTGTGCCATCAACTCATCCACAAATCCGGCATAGCCGTCAGGATTGCGGGATTG
TCGGACTGGTTCATGAACAGTGCACCAGGCAGTTGCGCGCCGAGCTGGGCGGGCCAGTCTCTGCCTTTCAACGACGGC
CACTTCATCTTCCGCGATAGTCGCCTTCAACATAGCGAATTTCGGCACCCAAGGCCCGCATCATCCGGATTTTATCCG
GCGCGGCCGTGATGATCCACGACCGCGATAAAGCGAAGACCAAACTCCAGCGCCGCAAGAGCCAGACCTGTGCCCGTG
TTGCCTGATGAGGATTCAACGATCGTGCCGCCACGCGGCAGGCGCCCATCCGCCAAGGCCGCAACCACCATGCTGCG
CGCCATGCGGTCTTTCATTGAGCCGCCAGGATTGTTCTTCTCCATTTTGAGCAAAAGTTTTGCATTGCTTGTTGCCA
GATCAAGCGCGATCAGGGGGTCTGGCCAATCAATTGCGTGACGGTTGTATAGAGCATAGTACCTCCTCACAGGTAT
```

FIG. 6H

```
CCGGAATAAGTTCGGACAGTCCATCTGCGGTCCTCCTGACACATAAGCGGATTGGCATGGGGTGGCGGTGAAACTGG
TTTTCCATCAGATCCATCTGATAGCCGCCGGTATTGACATAGATGAGCAAATCACCAGCTTGCGGGGTAATCGGAAA
GTCGAGCCAGCGGTTGGAGACAATATCTTCATCAAGGCAGCTATGTCCGGCAAGATAGGCGCGCACAGGAGTGGTGC
GTGCAGCTTCCGGCCCGTGCGGCACCACAATGGGATCGATCAGAAATTCTGATGCGAACCATGTTTCGCATGCACTG
AAGCTGCTGCCCTCCACAAAAATTGCTGCTGACTGCGCACCCAGTGCCTTCACTCTCGTCACTCTGAAAGCCGTGAT
TGCAGTCTGATCCGCAAGGGCCCGCCCCGGCTCCATCCCCAGCGTAAGATTTTCCTGACGGAAATATGTTGCGACAT
CGCGCCCGTCCTGCATTTTGGATTGCAACAGGTGAGTTAACCACTCCGTTGCGCAAACAGGTCCTCCATAGGGATAA
AAAGACTGTGGCAGATGGTTGGTGCGATAATCCTGCGCCGTTTGCGCCTCCAGAAAGGCGGCGTAGGTCGGGTGATC
GACATATTGCACCGGCAACCCACCACCAATATCGATCATGCGGGGAGAAAGCCCCATGCCGCGCGCTTTGGCAATGA
GATCCGCTGCTTCATTCAATGCTTCGATGCGCGCCTTAACGCTATAACCACTCAAGTGGAAATGGATTCCATCAAAT
CGTAGGGCTGGGGTGCCTGCCAAACGATGCAGGCACGAAACAACGTCTTGAGCATCCATGCCGAAGCGGCTTTGCCC
TTGATTTTGGGGCCTTAATCTCAAAAGCACGGGCTGAGGGTCACCGGCGCTTGGCAATTCCTTCAAAATATCATCGA
ATTCCTCAACGGAATCGATGGAAATCAGGGCCTTGCAGGCCATCAACGCTCTATGAAATGTCGATGTTTTGGCAGGA
CCGGTCGCAACAATATCGGCACCCTTTGCACCCAATGCCAAGGCATCCTGCAACTCGTACAGGCTGGAGACATCAAC
GCCTCCTTCAGCCTGAAGGGCAGCTCCCATAAGATTCACAGACTTGTTGACCTTCACACCATAATAAATTCTGCATG
GAACTTGACTGCCGCTCAATATGGCCTGCAAAGCCAGAAGATTATCGGCCAGCAGATCAGGCCAGATCAAATGGAGC
GGCGAGCCAAATCTGTTGAATCCTTCCCGCAACTGTTCATGCTTGTTTTCAATAAAATCTGCGACCTCGTCATGAAT
CAGGGGCGTCAGAGTGTGAGATTGCTTGGAGCCAAGTCTGTCATGCACAGCACCGCCCTGCCGCCTTGCATCGCCGAATC
CATGGTAGCCACAATTCCGGCTAATACCGCGAGCGGTACATCACATACAGGGTAATCATCCGCGAAGACGTGACGTG
TCGTTTTGATCGGAAATTTTTTGCCGGACCGCGCCATGGCAAAAATATCGTCTGGTGTAATGCATTCCTCAGGCCGC
CAACTCGTGACAGACACACGCTCATAATCCAGGAGGACAACAGGAATGACAGCGAGATTGAGCTGCCTTGCGACCTC
AAGCCGGTGATGCCCATCCATCACCAGAAACTGAGTGCGCTCGACCGCAATAGGGCGTGTCCAGATCTGCTGACGTA
AAATGTTTGGCGCAAATTCTCAACAACGCTTTGATCGACTTCTTCAGTGTCGACAAGTTTTTTGGGAGAGGCAAAA
TGATATGGCATAAAATACAGCCCTTCGGTGAAAATCGCTATTTCCGAAAATATGACTACATAAATCATGTTTAACAT
GTAGCGTTTATTTCCAGATGTCAATTTACAATCCTAAAAAAATATCCAGTATAAACAGATGGATAAAAGATATCTGG
CTATTTCATTCGCGATGAAAATAAAATCTTGACTCTTAATGTCATGTTCAATACCCAGCTGCTTGGGCGTGTATTTT
AAAGACATAGTTCACGGCAACCTTGCCGGTTCTGCTGAGGGGGATGCTGACATGATGGGTTTGAAAAGTGGCGTTG
CCATGGGTGCAATTCTGGCTGCTCTCGGCACTGTTGCGCAGGCAGAAGAGGACACGGTTCTCAAGCCAATTGTTGTT
GAGGGACAATCCTCATCGCCCAACGCAACCATAGGCAAACAGAGCGAACCTTATGCAGGGGGCATGGTCACCGGTAG
CGCTCGATTGGGCAGTCTGGGCAACCGCAGTTTCATGGATATGCCTTTCAGCACCAGCGGATATACTGCAAAAGTCA
TAGAGGATAAGGGAGCATCAACGGTTGGTGATGTGATGGAGAGCGATGCATCGGTGCGCAATACGCATCCGTCTGGC
GGCATTGTCGACTCTTTCTATATCCGTGGCTTTCCCATCGGTGACGGCAATTTTGGTGAAATTGCGTTTGATGGCAT
GTTCGGCGTCGCACCAAACTATCGCGTTTTTACCGATTATGCGGAATCCGTAGAAGTCCTGAAAGGGCCAACCTCCT
TCCTCTATGGCATTTCTCCCAATGGTGGTGTGGGCGGAACCATCAATATTGTTCCAAAGCGTGCTCTGGATACGGAC
CTGACCCGTGTCACCACCAGCTATGAATCGGATCTTCAGGTTGGAACGCATGTGGATATCAGCCGCCGCTATGGCAG
TGAACGGCAATTTGGCGTCCGGCTGAATGGCAGCGTTCAAGGTGGTGATGGCACTATCGACGATCTTTCTCGTTTTG
CCTATGTCGGTGCGGTTGCGCTGACTACGAAGGAGAAAATCTGCGCGCAACGCTCGATGTCATCAATCAATATGAA
CATTATGACGCGCCACAGCGTCCATTCTATCCCACAGCCGGCATTAAACTGCCGAGTGCACCGGACAATCGTCTGAA
TGTGCAGGAGTCCTGGGAATGGTCAGCAACCCGGGAGTTTTCAACACTGGGGCGCGTTGAATATGACCTCAGCGATG
ACGTGACCGTGTTTGGTGCCGTCGGTGGTGGGAAGTCAAACGTCGAGCGTCTGTTTGGCACGCCCACAATCACGGAC
TCTGCCGGCAATGTCAGCATCGTACCGCAGCATTATATTTTGATGTGCAGAGACGAACCGCAGAAATCGGCACTCG
CGGACAGTTCGACACCGGCATCATCGAGCACTCCGTGACATTGCAGGCAATTATATGCTGCAATGGCTGTCGCGAG
GCTCCAATTCCGGTACGGCCCAAACCACCAATCTGTATAATCCGGTTGATCGTGAGGAGCAATTTGTTGCCAAGCCG
TCCAGCGTACCGAAAGTAACGGAAAGCGAATTCTACGGTGTGGCTTTATCCGATACAATGTCCATATGGGATGAGCG
GGCGCAATTGATGGTTGGCGGGCGCTTTCAACACATCGATTCCGAAAACTACAGCTCGACAACTGGCGCTGTAACAT
CCTCTTCCGACGCGAGCGCAATAACACCCATGGTTGCTGTGGTTAAGCCGTGGGAAAATGTATCGCTATATGCA
AACTATGCGGAAGGGTTGAGCATCGGGGAAACGGCTCCGACAAACGCCGTAAACGCAGGCGAAACCCTCAGCCCCTA
TAAATCCAAGCAATATGAAGTGGGAACCAAGATAGACACCGGTCCGGTGACGCTCACCGCCAGTCTTTTCCAGATCG
AAAAGCCGTTTGGTGTTTTGGAGACGCGTGGCAGCGATCTGGTTTTCGAACGCGGTGGCGAACAGCGTAACCGGGGT
CTTGAACTTTCAGCGTTCGGCGAGTTGACCGACACCGTGAGACTGCTTGGCGGCGTTACGTTCATGCGGGGCGAGTT
GACGAAAACCAACAATGCCTCGACGCAAGGCAATGACCCCATTGGCGTGCCAAAAGTCCTCGTAAACCTCGGTGCAG
AATGGGACACCCCATTCCTGAGCGGCTTCACCCTGACGGGCAACGTCATCCACACCGGCAAACAATATGCCGATACA
GCCAATATCCAAAAACTACCGGCATGGACACGTCTTGATCTCGGCGCGCGCTACAAGACAACGATCAAGGAGCGACC
CGTTACCTTCCGTGCCGAAGTCGAAAACGTCTTCAACAAGAATTACTGGTCAGGTGTCGCAAGCTTTGGCACTGTGA
CACAAGGGCCCGTTGACCGTTAAAATATCGATGACAACCGATTTTTAAGTCTCGTTAACCACTTGATGTATCGTTT
GCGAGTCAGCCGCCTTTCGAAGAGGCGTTGTCTTCGTCTATGGGGCTTGACTGTCGATTTCCACTTGGCCGGCACTG
TAAACTTACCGCCTTGAACGCAACATCTGGGCGTGAGGAATTAGTTCATGCGGCGTTGAAGGCGCGCGATTTGGTGCC
ATGCTTGCATGGCAGCTGTTCGCAGTTCGCGATGGTGGACGGATGGAATATCGTGGCGGGGAATGTGAAAAAGGTTG
GTGATCGGGTCATGGATGGAAACGAAACGCTGAAGATGTCGTGTTGACTTGAAGCGCTTCATGATCCTCTCCCGTCG
TCGGACGGGCTGATGAGAGTTTTCCGACCGATTTTTCAATCCTTTGTGAGAACGATGCTCAATGCCGGGCATGACCT
CCCGCTTTGCTGCACCATAGGATCGTAGTTTGTCGGTAATCATCACACGCAGCGCACGGCCTTGGGCTTTCAGGAGC
TTGCGCATCAAACGTTTTGCCGCCTTGGTATTGCTGCGGTTTTGCACCAGCACATCGAGAACAAAGCCATCCTGATC
```

FIG. 6I

```
AACGGCGCGCCAAAGCCAGTGTTTCCTTCCACCGATGGTGATGACAACCTCATCGAGATGCCATTTGTCCCCGAGCC
TGCCGGTAGATCGCTTGCGGATATCGTTGGCAAAATGTCTA-11899 (SEQ ID NO: 15)
```

FIG. 6J

**P1388 in *Agrobacterium vitis* F2/5 encoding transposase**

DNA sequence:

5'-
ttgtacgatagagcagtgggcatgaacatttcttcgtctaccttcgcctcctatcgttacaaacgtcaccgctttcc
agccgagattatcgctcacgcggtttggctgtacttccggtttccattgagcctgcggcatgtcgaggatttgctgg
ccgaacgcggtattgacgtttcgttccagacagtatcggaatgggccgccaaatttggctccgagtttgctgcgttg
cttcgccggcgctcaaagggcggctttgccgataaatggcacctcgatgagatggtggtaaccatcaaaggccggaa
atacggctctgtcgcaaagattccgtttgtgctggaaataagggagatagttttcagcgagacttttgatgagcgat
ttcaagtggcgtcatttcagggcgaggtgatcttgtgggcagttcgctggtattgccgctatggggtgagctaccg
cgatcttga-3' (SEQ ID NO: 16)

Amino acid sequence:

MYDRAVGMNISSSTFASYRYKRHRFPAEIIAHAVWLYFRFPLSLRHVEDLLAERGIDVSFQTVSEWAAKFGSEFAAL
LRRRSKGGFADKWHLDEMVVTIKGRKYGSVAKIPFVLEIREIVFSETFDERFQVASFSGRGDLVGSSLVLPLWGELP
RS (SEQ ID NO: 17)

**P1389 in *Agrobacterium vitis* F2/5 encoding a hypothetical protein**

DNA sequence:

5'-
gtgataaaaccagccaccactctctttgcggctctgctgtcgtgtcttgtcgcgcagatgccatctgctgtggcaca
ggagccagcggctcaaacatccaatgcagcaacaacgccgcatcgcatcaccgtgacagacattgctggtcggcagg
tgtcattgcctgttcctgtccatcgcatgttgttgggcgaaggcggcagctctatcttgtcgcgtcattggagtcc
gagaatcctctggcgtttctggcaggatggaaaaatgacctcattgaagccgacccgcaacctatgcccaatatgt
cgcgaagtttccgaaactggcccaactgccaacctttggcggcaaggaagcaggtctgattgatcttgagtctgcca
ttgttcaaaagcctgatgttgtgcttttgaatctcgaaaccagcgtgccagcaaagagtccgaatatatcgaaaag
ctggcatcactgggaataccggttctttatatcgatttccggcatcaaccccttcacaataccgaaccaacaatccg
ccttttgggcgagatcatgggacgtgaaaagcgcgccgaggaaattattgccttcaggaaaaaggcattgtcgcaag
tgacggatgtgattgaacaaaaaagcccgcacgaccgaatgtctttgtcgagcggattggcggttatgcggatgat
tgctgcctcacctttggcaatgagaattttggtcgctatgtcgaaatcgccggcgggcacaatatcggcggtgattt
tcttccggaaccttcggacaattgaaccggaacaggtgattgctgccgacccggatcaggttgtggtcacgagcg
ccaattgggaagcttatgttccgggtggacactggataccctggggccgggtgccaacagacaggaagccgaacga
aaactggaatggttcacgacaagaaatgcctatattggcaccaaagcggtcaaaaaccgcagtttccatggcatatg
gcatcagttctacaatagcccttatgaattcatcgccataacaaatcgcaaaatggcttcatccggatttgttcg
ccgatctcgatccagacgagacattcaggaatatcatcgcctttttctgccaatcgaatacaagtcaggctatagt
ataagccttgcgccctga-3' (SEQ ID NO: 18)

Amino acid sequence:

MIKPATTLFAALLSCLVAQMPSAVAQEPAAQTSNAATTPHRITVTDIAGRQVSLPVPVHRMLLGEGRQLYLVASLES
ENPLAFLAGWKNDLIEADPATYAQYVAKFPKLAQLPTFGGKEAGLIDLESAIVQKPDVVLLNLETQRASKESEYIEK
LASLGIPVLYIDFRHQPLHNTEPTIRLLGEIMGREKRAEEIIAFRKKALSQVTDVIEQKKPARPNVFVERIGGYADD
CCLTFGNENFGRYVEIAGGHNIGGDFLPGTFGQLNPEQVIAADPDQVVVTSANWEAYVPGGHWIPLGPGANRQEAER
KLEWFTTRNAYIGTKAVKNRSFHGIWHQFYNSPYEFIAIQQIAKWLHPDLFADLDPDETFREYHRLFLPIEYKSGYS
ISLAP (SEQ ID NO: 19)

FIG. 6K

**P1390 in *Agrobacterium vitis* F2/5 encoding MFS-type transporter y4xM**

DNA sequence:

5'-
atgctcagggcaagcacgcctgtgtttctgctgctgtttgcgctccagttcatttccatgggagccatggaaatgag
cggtcctttctggccgctgcagatcagggtactcagcccgtcggatacggcgttcggattggcaagtatcggggttt
atatttgcccatgcttggcatttccctcaccagcgcattctgggggcgtatgggtgaccgctatggcaatcgcttg
atgatggttcgggccttgcgggggttggcgatcacccagcttctgattgcgcttgcccaagatgtctgggtcatcct
gtttctgcggttcttacaggggcttcgccggctatattgcgcccgcgcaagcctatgccgtgcaggtcaatagcg
ggcgtgatcgcgccagtctgttcgcctggttgcaggtggcgaccaatgtcggttcgctgggcggcgcatttgcgggt
ggtctcattctggatgcaatgccattcgcggccgttaatatcacggccggggccgtatgtggtctatgtgcccttgt
tgcctgggcaacattgcccatcccgcccatcagacagaatgcaccgcgctccgcttcaagcgcgtcacccgggcc
atccagaaagttctgcaccagtcgtcgggttgctggttttgatttgcgtattgttggccagccgaatggtgctgcaa
gtgccgttttcgctctacatgacccaagcttttcggagccaaccactggattattggcctcagctacgggctcatggc
gtttggttttgtgattggcgccccctctgggcgtctgttcaaaatgcgcagccttggctttgttggcggcaa
acaccgcgatcgctctggcctgcgcaagcatcgctttgatagcgggctacacaaccctcgttccgttttttgcagga
ttatactttgtctggggcattctgcttggtggtacgacaccggttcttacctcgcgtctttcccagtccacagcctt
caatcggcaaggtgaaattttgggccgtgcgcaaagctggcagcaaatcgcttccattctgggtatagcagccggtg
ttgggtccatgcagctttggggtgctgataccgcattttccctggtatcggcgtgttacatcctgtcatttttatc
ggcctgtcgctcttgctcaaaagcggccccttacccaaccgcataggataa-3' (SEQ ID NO: 20)

Amino acid sequence:

MLRASTPVFLLLFALQFISMGAMEMSGPFWPLQIRVLSPSDTAFGLASIGVYICPMLGISLTSAFWGRMGDRYGNRL
MMVRALAGLAITQLLIALAQDVWVILFLRFLQGAFAGYIAPAQAYAVQVNSGRDRASLFAWLQVATNVGSLGGAFAG
GLILDAMPFAAVNITAGAVCGLCALVAWATLPIPPIRQNAPRSASSALTPGHPESSAPVVGLLVLICVLLASRMVLQ
VPFSLYMTQAFGANHWIIGLSYGLMAFGFVIGAPLWARLFKMRSLGFVLAANTAIALACASIALIAGYTTLVPVFAG
LYFVWGILLGGTTPVLTSRLSQSTAFNRQGEILGRAQSWQQIASILGIAAGVGSMQLWGADTAFSLVSACYILSFFI
GLSLLLKSGPLPNRIG (SEQ ID NO: 21)

**P1391 in *Agrobacterium vitis* F2/5 encoding siderophore synthase**

DNA sequence:

5'-
atgacccatttgctttcgcctttgtttgacatccatgcgcagaccgatgaccagccgttgcgggattttgccgttgc
caatgcaatcagtcgccttgttcgctgcctgtttgcagaacgtcttctggctcctgaagcgttgctctggtcgcgtg
acaagcatcaagcctggttgccgctgtggaacacgcgccgtgtgctgcattttaaacatttgcatgcggcacccgct
ggcaccttgcaaaaccgtggcgagattgaaattctcgacgccgacggcggccatgcccggattgaccatcccgatgc
tttgctgcgggaagtgttcgcttcgttgtccatctctccggccctgatgggcttgaggttttgatgcgcgatatcg
ccgacagcatcaacaatgatatgctggcccgccgacaccggcaggtctggctgcgagcctgaatgagaagatcaaa
caatccggtgcggtgcattttctgggctatctctacggtcatttgcctgcacatctgccggcaatgctgattgacca
gtgggtgcgctcgaaggtcatccgttttatccgacatggaaggcaaaaccgagtttgcagcccgaagaggttgttg
ccctttcgcctgaattcggggccaaggtgccggtccggattgcggccttgcgtcggggttgggcctatgtggaaaaa
atgccacatgtgactgattacaatgactggttttctgcccagtttcccgaattgtttgccgcgtggaaagaccatct
gagcgcacagggcaaatcagcgcaagactggattcctttgcccatccacggatggcacctcgagcattttgtccgcc
gcgaatttggacaggaaatcgcctctggcatcttgctgttggacgggccagacattgacacctcgccatccatgtca
tttcggaccatgttaccggacgatgaaacgttgcgcccttttcatcaagttgccggttgccatctggctcaccagcga
gcagcgcagcttgcaggccaaatccattcacatggggcctcggctttccacgttgatcaccgatattctggccaatg
aaccggacatggccgcacaattggaaatcttcaccgaagaattgggagccattctgcacgatcccgataccggcgat
gagcatcgcggcgattttttgtcggtggtctatcgcaacgcccagccttaaagcgcgaggatggacgctatgcggt
gacggtcgcgcacttctaagtgcaagtcccaaggtggacgaccattgatctgcgagctgattgcccgttacgcga
atgaggaacaggcaagcgttgtcgctttttccgccggtatgttgaggtggtggttcggcctgcgttggcgatgtat
cttctttatggcatcgcttttgaggcccatcagcaaaacaccaccatcgtgtttgatccttccggttctgcggaaaa
gctgatcattcgggattttggtgatggccgcagctttgcgcctctgctcaaacagcgtggctatcacctcaaaccct
ttcagcgtgctgggattttgcccaccacctttgacgatgacattgggctggttcgctcgttttttgatcgacgcctgc
tttatatgccatctgcatgaaattgctctgtgcctgacccagcactatagtatcggcaatgataggctctggacagt
gatcaaagaggtaacgcaagaggcgtttgaaacattgcggcctcgtgtgtcttcggacacgttctggcaagaagaac
gagatgccctgcttgaaaaaaaatggcccacccggtcggttctcaccatgcatctccagcgatatagcgactatcgg
gtggagcatgagctgcccaatcctctggttggccgtgaatgctga-3' (SEQ ID NO: 22)

FIG. 6L

Amino acid sequence:

MTHLLSPLFDIHAQTDDQPLRDFAVANAISRLVRCLFAERLLAPEALLWSRDKHQAWLPLWNTRRVLHFKHLHAAPA
GTLQNRGEIEILDADGGHARIDHPDALLREVFASLSISPAPDGLEVLMRDIADSINNDMLARRHRQVWAASLNEKIK
QSGAVDFLGYLYGHLPAHLAAMLIDQWGALEGHPFYPTWKAKPSLQPEEVVALSPEFGAKVPVRIAALRRGWAYVEK
MPHVTDYNDWFSAQFPELFAAWKDHLSAQGKSAQDWIPLPIHGWHLEHFVRREFGQEIASGILLLDGPDIDTSPSMS
FRTMLPDDETLRPFIKLPVAIWLTSEQRSLQAKSIHMGPRLSTLITDILANEPDMAAQLEIFTEELGAILHDPDTGD
EHRGRFLSVVYRNAQPLKREDGRYAVTVAALLSASPKDGRPLICELIARYGNEEQASVVGFFRRYVEVVVRPALAMY
LLYGIAFEAHQQNTTIVFDPSGSAEKLIIRDFGDGRSFAPLLKQRGYHLKPFQRAGILPTTFDDDIGLVRSFLIDAC
FICHLHEIALCLTQHYSIGNDRLWTVIKEVTQEAFETLRPRVSSDTFWQEERDALLEKKWPTRSVLTMHLQRYSDYR
VEHELPNPLVGREC. (SEQ ID NO: 23)

**P1392 in *Agrobacterium vitis* F2/5 encoding Y4xO (Tauropine dehydrogenase)**

DNA sequence:

5'-
atgagggtcgccatttgcggcgcaggccgcaccgggcatttgaatgccgtgcttttttaagcaaaatccgcaggtcca
tctctccgttttgacggagaatgacactcttgccgccaattgggctggaaatcctgctccatggcaggctttttttgc
cggatggtcagggtatgtccgggcgtcctgattacgttggcaacaaccccgataaagcggttgggaacgctgatctg
attgtcattacccagccagccatgccagatccgctgttttgcagcggatcgcaggcagtatctccagcaccaagca
ggttttcgtgggtgctattccgggcttttgcggttttgactggctggctgccgatcacttaggcgcaagggataatg
tggtcatctggggtttgaaggatgtgccgcatatcgcctacgaccttgttgccggacagagcgttcgcatgggcggc
gctaaagcccatttgtttgctggccttcatcggcgggaatccgcccaaagtgccaaggctctgcaaacaatgctgac
cgcactttacaatgcgcctgtaaccttttgcaggactatctggaaatcaccctgacaccccgcaatgcgctgatgc
atccagcggtgctctacggcctgctggggccgggcgctccctgggagcgtaaaccgttctccgagccgctgtgctgg
tggagtgattgccctgaggaaggcgcgcgcttgctcgaaaatcaggccgcatatgtcaggcgat
tgcgacccgaaccggtcttgatctcagctccgtcaaacctttgcgcaggaactgattgaagcctatggcgatcaga
ttgccgatagtcaaacgatgtattccctgctcagaacaaacagcgcctatgcgggaattcaattgccgctgatcccc
aatcatcatggtcaaggctggttgatcgatctgcaaagccgtgcctttcatgaggatgttgcatgcgggcaggcatt
gctggtcaagatcgcagagcggctggcggtaccgattccaaccatctcgaaaacctacacgtgggcgcgccactatc
atggtgctttgccggatggattaagcccggttcctgatgattggctggaggctgcctga-3' (SEQ ID NO: 24)

Amino acid sequence:

MRVAICGAGRTGHLNAVLFKQNPQVHLSVLTENDTLAANWAGNPAPWQAFLPDGQGMSGRPDYVGNNPDKAVGNADL
IVITQPAHARSAVLQRIAGSISSTKQVFVGAIPGFCGFDWLAADHLGARDNVVIWGLKDVPHIAYDLVAGQSVRMGG
AKAHLFAGLHRRESAQSAKALQTMLTALYNAPVTLLQDYLEITLTPGNALMHPAVLYGLLGPGAPWERKPFSEPLCW
WSDCPEEGARLLEMFDAENQAICQAIATRTGLDLSSVKPLRQELIEAYGDQIADSQTMYSLLRTNSAYAGIQLPLIP
NHHGQGWLIDLQSRAFHEDVACGQALLVKIAERLAVPIPTISKTYTWARHYHGALPDGLSPVPDDWLEAA (SEQ
ID NO: 25)

**P1393 in *Agrobacterium vitis* F2/5 encoding Y4xP (Cysteine synthase)**

DNA sequence:

5'-
atgctctatacaaccgtcacgcaattgattggccagaccccctgatcgcgcttgatctggcaacaagcaatgcaaa
acttttgctcaaaatggagaagaacaatcctggcggctcaatgaaagaccgcatggcgcgcagcatggtggttgcgg
ccttggcggatgggcgcctgccgcgtggcggcacgatcgttgaatcctcatcaggcaacacgggcacaggtctggct
cttgcggcgctggagtttggtcttcgctttatcgcggtcgtggatcatcacgccgcgccggataaaatccggatgat
gcgggccttgggtgccgaaattcgctatgttgaaggcgactatcgcgaagatgaagtggccgtcgttgaaaggcaga
gactggccgcccagctcggccgcgcaactgcctggtgcactgcttcatgaaccagtccgacaatcccgcaatcctgac
ggctatgccgatttgtggatgagttgatgcgcacaactgcttcctgatggattggatgcctttgttggttgcgtgggtac
gggtgggtcgatgacgggcatatcccagcgcctcaagcgcctcaatcccgccatcaagacaattgcggttgagcctg
ctggttccattgttttggtaagccggggcattcctattaccaatctggcacaggtacccgcaggcgatgaagtc
ggcaaggttctggattatagctgcattgatgaaggtgttcaggtcaccgatacgcaagcatttgaaacggcacgcta
tattgcccgacgcaaaggtattctcgttggtggatcaaccgggggtacaatttacaaagctctcgaattcatcgcat
ccggtaaattgagcggcacaattgttacagccgtcgcagatgggggtgaaaaatacctggcatccgtgtttgacgat
gagtggatggaaaagcgcgggcttctcaatccggcaatcgcagctcaattggatggttggttcaatggcttggcagg
tgcggcatga-3' (SEQ ID NO: 26)

FIG. 6M

Amino acid sequence:

MLYTTVTQLIGQTPLIALDLATSNAKLLLKMEKNNPGGSMKDRMARSMVVAALADGRLPRGGTIVESSSGNTGTGLA
LAALEFGLRFIAVVDHHAAPDKIRMMRALGAEIRYVEGDYREDEVAVVERQRLAAQLGAQLPGALFMNQSDNPANPD
GYAGFVDELMAQLPDGLDAFVGCVGTGGSMTGISQRLKRLNPAIKTIAVEPAGSIVFGKPGHSYYQSGTGTPAGDEV
GKVLDYSCIDEGVQVTDTQAFETARYIARRKGILVGGSTGGTIYKALEFIASGKLSGTIVTAVADGGEKYLASVFDD
EWMEKRGLLNPAIAAQLDGWFNGLAGAA (SEQ ID NO: 27)

**P1394 in *Agrobacterium vitis* F2/5 encoding diaminopimelate decarboxylase**

DNA sequence:

5'-
atgagacttggctccaagcaatctcacactctgacgccctgattcatgacgaggtcgcagattttattgaaaacaa
gcatgaacagttgcgggaaggattcaacagatttggctcgccgctccatttgatctggcctgatctgctggccgata
atcttctggctttgcaggccatattgagcggcagtcaagttccatgcagaatttattatggtgtgaaggtcaacaag
tctgtgaatcttatgggagctgcccttcaggctgaaggaggcgttgatgtctccagcctgtacgagttgcaggatgc
cttggcattgggtgcaaagggtgccgatattgttgcgaccggtcctgccaaaacatcgacatttcatagagcgttga
tggcctgcaaggccctgatttccatcgattccgttgaggaattcgatgatattttgaaggaattgccaagcgccggt
gaccctcagcccgtgcttttgagattaaggcccccaaaatcaagggcaaagccgcttcggcatggatgctcaagacgt
tgtttcgtgcctgcatcgtttggcaggcaccccagccctacgatttgatggaatccatttccacttgagtggttata
gcgttaaggcgcgcatcgaagcattgaatgaagcagccggatcttcattgccaaagcgcgccgcatggggctttctccc
cgcatgatcgatattggtggtgggttgccggtgcaatatgtcgatcaccgacctacgccgcctttctgaggcgca
aacggcgcaggattatcgcaccaaccatctgccacagtcttttttatccctatggaggacctgtttgcgcaacggagt
ggttaactcacctgttgcaatccaaaatgcaggacgggcgcgatgtcgcaacatatttccgtcaggaaaatcttacg
ctggggatggagccggggcgggcccttgcggatcagactgcaatcacggctttcagagtgacgagagtgaaggcact
gggtgcgcagtcagcagcaattttttgtggagggcagcagcttcagtgcatgcgaaacatggttcgcatcagaatttc
tgatcgatcccattgtggtgccgcacgggccggaagctgcacgcaccactcctgtgcgcgccctatcttgcggacat
agctgccttgatgaagatattgtctccaaccgctgctcgacttttccgattacccccgcaagctggtgatttgctcat
ctatgtcaataccggcggctatcagatggatctgatggaaaaccagtttcaccgccaccccatgccaatccgcttat
gtgtcaggaggaccgcagatggactgtccgaacttattccggatacctgtgaggaggtactatgctctatacaaccg
tcacgcaattga-3' (SEQ ID NO: 28)

Amino acid sequence:

MRLGSKQSHTLTPLIHDEVADFIENKHEQLREGFNRFGSPLHLIWPDLLADNLLALQAILSGSQVPCRIYYGVKVNK
SVNLMGAALQAEGGVDVSSLYELQDALALGAKGADIVATGPAKTSFHRALMACKALISIDSVEEFDDILKELPSAG
DPQPVLLRLRPQNQGQSRFGMDAQDVVSCLHRLAGTPALRFDGIHFHLSGYSVKARIEALNEAADLIAKARGMGLSP
RMIDIGGGLPVQYVDHPTYAAFLEAQTAQDYRTNHLPQSFYPYGGPVCATEWLTHLLQSKMQDGRDVATYFRQENLT
LGMEPGRALADQTAITAFRVTRVKALGAQSAAIFVEGSSFSACETWFASEFLIDPIVVPHGPEAARTTPVRAYLAGH
SCLDEDIVSNRWLDFPITPQAGDLLIYVNTGGYQMDLMENQFHRHPMPIRLCVRRTADGLSELIPDTCEEVLCSIQP
SRN (SEQ ID NO: 29)

**P1395 in *Agrobacterium vitis* F2/5 encoding Y4yB**

DNA sequence:

5'-
atgttaaacatgatttatgtagtcatattttcggaaatagcgatttttcaccgaagggctgtattttatgccatatca
ttttgcctctcccaaaaaacttgtcgacactgaagaagtcgatcaaagcgttgttgagaatttgcgccaaaccattt
tacgtcagcagatctggacacgcccctattgcggtcgagcgcactcagtttctggtgatggatgggcatcaccggctt
gaggtcgcaaggcagctcaatctcgctgtcattcctgttgtcctcctggattatgagcgtgtgtctgtcacgagttg
gcggcctgaggaatgcattacaccagacgatattttgccatggcgcggtccggcaaaaaatttccgatcaaaacga
cacgtcacgtcttcgcggatgattaccctgtatgtgatgtaccgctcgcggtattagccggaattgtggctaccatg
gattcggcgatgcaaggcggcagggcggtgctgtcatga-3' (SEQ ID NO: 30)

Amino acid sequence:

MLNMIYVVIFSEIAIFTEGLYFMPYHFASPKKLVDTEEVDQSVVENLRQTILRQQIWTRPIAVERTQFLVMDGHHRL
EVARQLNLAVIPVVLLDYERVSVTSWRPEECITPDDIFAMARSGKKFPIKTTRHVFADDYPVCDVPLAVLAGIVATM
DSAMQGGRAVLS (SEQ ID NO: 31)

FIG. 6N

P1396 in *Agrobacterium vitis* F2/5 encoding Ferrichrome-iron receptor

DNA sequence:

5'-
atgatgggtttgaaaagtggcgttgccatgggtgcaattctggctgctctcggcactgttgcgcaggcagaagagga
cacggttctcaagccaattgttgttgagggacaatcctcatcgcccaacgcaaccataggcaaacagagcgaacctt
atgcagggggcatggtcaccggtagcgctcgattgggcagtctgggcaaccgcagtttcatggatatgcctttcagc
accagcggatatactgcaaaagtcatagaggataagggagcatcaacggttggtgatgtgatggagagcgatgcatc
ggtgcgcaatacgcatccgtctggcggcattgtcgactcttttctatatccgtggctttcccatcggtgacggcaatt
ttggtgaaattgcgtttgatggcatgttcggcgtcgcaccaaactatcgcgttttttaccgattatgcggaatccgta
gaagtcctgaaagggccaacctccttcctctatggcatttctcccaatggtggtgtgggcggaaccatcaatattgt
tccaaagcgtgctctggatacggacctgaccgtgtcaccaccagctatgaatcggatcttcaggttggaacgcatg
tggatatcagccgccgctatggcagtgaacggcaatttggcgtccggctgaatggcagcgttcaaggtggtgatggc
actatcgacgatcttttctcgttttgcctatgtcggtgcggttgcgctggactacgaaggagaaaatctgcgcgcaac
gctcgatgtcatcaatcaatatgaacattatgacgcgccacagcgtccattctatcccacagccggcattaaactgc
cgagtgcaccggacaatcgtctgaatgtgcaggagtcctgggaatggtcagcaacccgggagttttcaacactgggg
cgcgttgaatatgacctcagcgatgacgtgaccgtgtttggtgccgtcggtggtgggaagtcaaacgtcgagcgtct
gtttggcacgccacaatcacggactctgccggcaatgtcagcatcgtaccgcagcattatattttttgatgtgcaga
gacgaaccgcagaaatcggcactcgcggacagttcgacaccggcatcatcgagcactccgtgacattgcaggccaat
tatatgctgcaatggctgtcgcgaggctccaattccggtacggcccaaaccaccaatctgtataatccggttgatcg
tgaggagcaatttgttgccaagccgtccagcgtaccgaaagtaacggaaagcgaattctacggtgtggctttatccg
atacaatgtccatatgggatgagcgggcgcaattgatggttggcgggcgctttcaacacatcgattccgaaaactac
agctcgacaactggcgctgtaacatcctcttccgacgcgagcgcaataacacccatggttggtgtcgtgttaagcc
gtgggaaaatgtatcgctatatgcaaactatgcggaagggttgagcatcggggaaacggctccgacaaacgccgtaa
acgcaggcgaaaccctcagcccctataaatccaagcaatatgaagtgggaaccaagatagacaccggtccggtgacg
ctcaccgccagtcttttccagatcgaaaagccgtttggtgttttggagacgcgtggcagcgatctggttttcgaacg
cggtggcgaacagcgtaaccggggtcttgaactttcagcgttcggcgagttgaccgacaccgtgagactgcttggcg
gcgttacgttcatgcggggcgagttgacgaaaaccaacaatgcctcgacgcaaggcaatgacccattggcgtgcca
aaagtcctcgtaaacctcggtgcagaatgggacaccccattcctgagcggcttcaccctgacgggcaacgtcatcca
caccggcaaacaatatgccgatacagccaatatccaaaaactaccggcatggacacgtcttgatctcggcgcgct
acaagacaacgatcaaggagcgacccgttaccttccgtgccgaagtcgaaaacgtcttcaacaagaattactggtca
ggtgtcgcaagctttggcactgtgacacaaggggccccgttgaccgttaaaatatcgatgacaaccgattttaa-
3' (SEQ ID NO: 32)

FIG. 6O

Amino acid sequence:

MMGLKSGVAMGAILAALGTVAQAEEDTVLKPIVVEGQSSSFNATIGKQSEPYAGGMVTGSARLGSLGNRSFMDMPFS
TSGYTAKVIEDKGASTVGDVMESDASVRNTHPSGGIVDSFYIRGFPIGDGNFGEIAFDGMFGVAPNYRVFTDYAESV
EVLKGPTSFLYGISPNGGVGGTINIVPKRALDTDLTRVTTSYESDLQVGTHVDISRRYGSERQFGVRLNGSVQGGDG
TIDDLSRFAYVGAVALDYEGENLRATLDVINQYEHYDAPQRPFYPTAGIKLPSAPDNRLNVQESWEWSATREFSTLG
RVEYDLSDDVTVFGAVGGGKSNVERLFGTPTITDSAGNVSIVPQHYIFDVQRRTAEIGTRGQFDTGIIEHSVTLQAN
YMQWLSRGSNSGTAQTTNLYNPVDREEQFVAKPSSVPKVTESEFYGVALSDTMSIWDERAQLMVGGRFQHIDSENYS
STTGAVTSSSDASAITPMVGVVVKFWENVSLYANYAEGLSIGETAPTNAVNAGETLSPYKSKQYEVGTKIDTGPVTL
TASLFQIEKPFGVLETRGSDLVFERGGEQRNRGLELSAFGELTDTVRLLGGVTFMRGELTKTNNASTQGNDPIGVPK
VLVNLGAEWDTPFLSGFTLTGNVIHTGKQYADTANIQKLPAWTRLDLGARYKTTIKERPVTFRAEVENVFNKNYWSG
VASFGTVTQGAPLTVKISMTTDF (SEQ ID NO: 33)

**P1397 in *Agrobacterium vitis* F2/5 encoding transposase**

DNA sequence:

5'-
atgaccagatccagccgtgatccctttatcgtcgccaccgatttcccgcgaggtgattgcccatgcagtttggct
gtatttccggtttccgcttagcctgcggatggtcgaggatctgctggcagcgcgtggcatcatcgtctctcatcaaa
gcgtgcggctctgggcggagaaattcggtagacattttgccaacgatatccgcaagcgatctaccggcaggctcggg
gacaaatggcatctcgatgaggttgtcatcaccatcggtgcaaggaaacactggctttggcgcgccgttgatcagga
tggctttgttctcgatgtgctggtgcaaaaccgcagcaataccaaggcggcaaaacgtttgatgcgcaagctcctga
aagcccaaggccgtgcgctgcgtgtgatgattaccgacaaactacgatcctatggtgcagcaaagcgggaggtcatg
cccggcattgagcatcgttctcacaaaggattgaaaaatcggtcggaaaactctcatcagcccgtccgacgacggga
gaggatcatgaagcgcttcaagtcaacacgacatcttcagcgtttcgtttccatccatgacccgatcaccaaccttt
ttcacattccccgccacgatattccatccgtccaccatcgcgaactgcgaacagctgccatgcaagcatggcaccaa
atcgcgcgccttcacgccgcatga-3' (SEQ ID NO: 34)

Amino acid sequence:

MTRSSRDPLYRRHRFPAEVIAHAVWLYFRFPLSLRMVEDLLAARGIIVSHQSVRLWAEKFGRHFANDIRKRSTGRLG
DKWHLDEVVITIGGRKHWLWRAVDQDGFVLDVLVQNRSNTKAAKRLMRKLLKAQGRALRVMITDKLRSYGAAKREVM
PGIEHRSHKGLKNRSENSHQPVRRRERIMKRFKSTRHLQRFVSIHDPITNLFHIPRHDIPSVHHRELRTAAMQAWHQ
IARLHAA (SEQ ID NO: 35)

**F-avi5730 ( avi5730 in *Agrobacterium vitis* F2/5) Encoding siderophore
synthase (vicibactin biosynthesis non-ribosomal peptide synthase protein)**

DNA sequence:

ttgtcgcaggcgggccatgaagtggtctatgggcgtcagtctatcggctttcgcttcgcgcctgtcggggttgatcg
tgcacacgctggaattgagacgctgatgcttcgtcatccctgttaaatcgtcgctttgaagtgcgggcaggcggga
tcgtttatcagttgcttggccaaaagcccttgcctgttgttgagcgtgagcttgcaaaggatggggagttggagact
gtattacgggaggtttcctccacctattccggtagggcgcttgatctggaaaaggatgccgccgcgcaatttacgct
atttacggtaggtgggcaggctattggccttcctattgttgtcgttgcatcctctgattggtgaccggacggccctcgacc
ggttgccgtcgattccttgatgggcttgatcgacaggcgtgatttagggcgtgaagaggcgggttttgatgcg
gcacattggctggttcaaggcgccgcaatgccgcagatagcagatgctgacgccgatttctggtttaaccgattggt
ggcacaggagacggtggcgatgctgcccgccaggctccagcggcaggtgtggcaaattctggtccgcaaacatggc
gcgagcaggtcatcgaggtcgtgtgctcggcctcgacatctgtgttgatgtgacgcaggacagtctggcggcgctg
gccattgtgcttcgtcgctatagcggttgtggtacccagcggatcggctggtgacgcggcaggccgattgcccgt
tgcgacccgcaccgaagatctgttgctcgtcaccagcgaaatcgacggtcgtttggctcttgacgcagcgcgcgaac
ggctggcgaggggttgcaccgcctgttcccaccatttgccgttcgaagcgctgacgaatgccctggcgcggcgc
gacgatgggttcgaggcaggctattggccttgttcgcaaccggtgcgtgctgcggcccgcctccagctggaggctcaagg
tgtggccggtcagccggttgccgttctggtagagccgcctgcgcggcgcgatgcaggtctggtggttaccgtttccg
gtctggggtcggagacattggcgatccggctgggctatgaccagcagagccatagtgatgcaatgatcgaccggttc
gccacgatctccgtctggcgttcgaggctctgcggggcagccgagcagctggtcagcgattgctttcatgtc
ggttgaagagctggaccggctgtcagcgccctatcccgaccagcctgagaccgatgatggcacgccgatccatcagg
tgatttcggcccaggcgcagcgaaggccagacgctttcgcggtggcgcagggcgatacgtcaattacccatggcgcg
ctggaagccgcgccaaccggctcgcccatcggctggtcgccatgggatcggcccggaagaccgagtcgccgtggc

FIG. 6P

```
gctgaacaaatccatcgacgcgattatcgccattctggcggtgctgaaggccggtggcgcttttacgccggtcgagc
cggatcatccagaagcccgcaaccgccatatcctgagcgcgccgggtctgacgctggtgatttcgcggggcgttat
atcaccgatctgcgcgcgtgatatcggcacgccgatcctcaatctcgacacgctcgatctatcctcggaaagcaccga
gccgccggtcatcgccattgcgccagcccagcttgcctatgtgatctatacgtccggctccaccggtatccccaagg
gggtggctgttgagcatggtccgctggcgcatcattgcaaggcgacgctacgcatctatgaaatggatgagacttcc
tgcgaatatccggtcttgcccttcacctcggatggtgggcatgaacgctggatggtgccgctgatggcgggtggcgg
tgtggtgctgacggcggataagctggcgacgccggaagatgctttcgcgttgatgcgcaggcacggcgtcaacaatg
ccagcttgccgaccagctatgtccgggccttgccgaatatgcggcggaaagggcgggataccgcagctgcggctc
tattccttcggcggtgaagcgctatccaggcggtcttcgatctgctgaccgataatctcaaggcgcagatgctgat
caacggttatgggccaaccgaaaccatcatgacgccgatggtgtggaaaatcccggcgggaacccggtttgagggaa
cggttgcaccgattggccgggggtgtaggcgaccgccgcatctatgctggacagcgatctggtgccggtgccggtc
ggggtgatcggcgagatccatatcgcggcagcggtattgctcgcggctatctcggccagcggagctgacggcgga
tcgtttcattgatgatcctttttccgccaacggtgggcggatgtacaagtccggcgatctcggccgctggcgcgaag
atggcactgtagaatttgccggccgggtcgatcaccagatcaagttgcgtggctatcgcatcgagccgggcgaaatc
gaggcggtgctgcgggccgatccaacgtgtcggaagccgtggtgctgctgcatcaggacagtggacgcagcgcgtt
gatcgcctatgtggtggcgcgtgacgatgaggatgtcaacgtcaacgatcttcgccgccgccgtcaccgccctgc
cggattacatggtgccgcagcatatcatggtgcttgatgcgctgccgatggggccgaacagcaagcttgatcgaagc
gcgctgccgctgcccaagctgcaacgtgatatcgtcccccccgccgacgacaaggaagccgccattctggaggtctg
gaaacaggtccttgatatcgcagaactcagcgtcaccgaaaacttcttcgatgtcggcggccagtcgctggcggcgg
tgcggatcgtctcgcggctgaaaatgcagcaccgaaatgccgctgaccattgccgatatgttcaactatccgacc
gtgcgggatctggcgctggcgatggacgaaaaccggcaggaggacaaggtcggggcgatctatctcgccgcgacgg
cgaccgtccggtgctctattgcttcccgggtcttctggtcagcacgcgggaatatatgcggttggtggattatctcg
ggccgaaccagccggccacgggcttcgtctgctattcgctgaccgaaacgccagcgctcagcaccagggtcgaggat
attaccgcccgctacgccgaagcggtgcgcagccaggctaagggacggccttgcgccttttcttgggtggtcctgggg
cgggcttctcgcctatgaggcagcgcagcagcttggcaatgacgtcgatcttcggatgatcggcatggtcgatgtct
gcgacatgggcgatgaatttgccattggcgtctggccgcatttcgaacctggcgtgcgcgaacgaacccatgaggcc
gtgcagcgctggctgacagtcgcgccaatgcgcgaggcctggttgacgctaatggcggcgatggatgccgaggttta
cgagcaattcctgcatcatatcgttaagcataacgtgccgctgcctgtcgatgggccggatatcggctcggaagagc
atattttctgggttctgctcgataacgcgatgatttttccgtaattacagctgaaaacctccgcgttccgcatccat
gcgttttcggctgaagattcggtaacgcggggcctcagtgtcatcgactggcgccgctattctcctaatgcgacggc
ttgcgaattggtgaccggcaccaaccatctgtcgattatcggcaagtcccgtttccatcagcgttttgcccagcggc
tcgatctagccatccaggacaagccctaa (SEQ ID NO: 36)
```

Amino acid sequence:

```
MSQAGHEVVYGRQSIGFRFAPVGVDRAHAGIETLMLRHPLLNRRFEVRAGGIVYQLLGQKPLPVVERELAKDGELET
VLREVSSTYSGRALDLEKDAAAQFTLFTVGGQAIGLLLSLHPLIGDRTALDRLAVDFLDGLDRQADLGREEAGLLDA
AHWLVQGAAMPQIADADADFWFNRLVAQETVAMLPAQAPAAGVANSGPQTWREQVIEVVCSASTSVVDVTQDSLAAL
AIVLRRYSGCGTQRIGLVTRQADCPVATRTEDLLLVTSEIDGRLALDAARERLGEGVATALSHHLPFEALTNALARR
DDGFEAASLVATVLDVRPALQLEAQGVAGQPVAVLVEPPARRDAGLVVTVSGLGSETLAIRLGYDQQSHSDAMIDRF
AHDLRLAFEALRGQPEQLVRAIAFMSVEELDRLSAPYPDQPETDDGTPIHQVISAQAQRRPDAFAVAQGDTSITHGA
LEAAANRLAHRLVAMCIGPEDRVAVALNKSIDAIIAILAVLKACGAFTPVEPDHPEARNRHILSAPCLTLVISRGRY
ITDLPRDIGTPILNLDTLDLSSESTEPPVIAIAPAQLAYVIYTSGSTGIPKGVAVEHGPLAHHCKATLRIYEMDETS
CEYPVLPFTSDGGHERWMVPLMAGGGVVLTADKLATPEDAFALMRRHGVNNASLPTSYVRGLAEYAAEKGGIPQLRL
YSFGGEALSQAVFDLLTDNLKAQMLINGYGPTETIMTPMVWKIPAGTRFEGTVAPIGRGVGDRRIYVLDSDLVPVPV
GVIGEIHIGGSGIARGYLGQPELTADRFIDDPFSANGGRMYKSGDLGRWREDGTVEFAGRVDHQIKLRGYRIEPGEI
EAVLRADPNVSEAVVLLHQDSGRSALIAYVVARDDEDVNVNDLRRAAVTALPDYMVPQHIMVLDALPMGPNSKLDRS
ALPLPKLQRDIVPPADDKEAAILEVWKQVLDIAELSVTENFFDVGGQSLAAVRIVSRLKMQHPKWPLTIADMFNYPT
VRDLALAMDENRQEDKVGAIYLRRDGDRPVLYCFPGLLVSTREYMRLVDYLGPNQPATGFVCYSLTETPALSTRVED
ITARYAEAVRSQAKGRPCAFLGWSWGGLLAYEAAQQLGNDVDLRMIGMVDVCDMGDEFAIGVWPHFEPGVRERTHEA
VQRWLTVAPMREAWLTLMAAMDAEVYEQFLHHIVKHNVPLPVDGPDIGSEEHIFWVLLDNAMIFRNYQLKTSAFRIH
AFSAEDSVTRGLSVIDWRRYSPNATACELVTGTNHLSIIGKSRFHQRFAQRLDLAIQDKP (SEQ ID NO: 37)
```

BIOLOGICAL CONTROL OF CROWN GALL DISEASE ON GRAPEVINES

CROSS-REFERENCE TO RELATED APPLICATIONS

This application claims benefit of U.S. Provisional Application No. 61/635,160, filed Apr. 18, 2012, which is hereby incorporated by reference in its entirety.

STATEMENT AS TO FEDERALLY FUNDED RESEARCH

This invention was made with government support under Hatch Grant No. 2009-10-381 awarded by the U.S. Department of Agriculture. The government has certain rights in the invention.

BACKGROUND OF THE INVENTION

This invention relates to biological control of crown gall disease on grapevines as well as enhancing grapevine development.

Crown gall disease of grapevine caused by *Agrobacterium vitis* is a limiting factor to grape production in several regions of the world (Burr et al. (1999) Annu. Rev. Phytopathol. 37:53-80). *A. vitis* survives systemically in grapevines and therefore is disseminated in propagation material (Burr et al. (1984) Plant Dis. 68:976-978; Burr and Katz (1983) Phytopathology 73:163-165; Goodman et al. (1987) Am. J. Enol. Vitic 38:189-193). Like crown gall on other plant species, tumorigenesis results following the transfer of a set of oncogenes called the T-DNA that are carried on a bacterial Ti plasmid; the T-DNA becomes integrated and expressed in the plant host (Chilton et al., (1977) Cell 11: 263-271) leading to crown gall. *A. vitis* strains can be grouped based on the type of Ti plasmid they carry and may also be designated by the opine catabolic gene(s) that resides on their Ti plasmid (Otten et al. (1996) Mol. Plant-Microbe Interact. 9:782-786).

There are no effective chemical controls to combat crown gall and therefore the interest in developing a biological control. Biological control of crown gall on specific crops, such as stone fruits has been successfully implemented in commercial agriculture using *A. radiobacter* strain K84 (Farrand, (1990) In R. R. Baker, and P. E. Dunn (Eds.) pp. 679-691). K84 is not effective against *A. vitis* strains on grapevine and therefore several research groups have investigated other candidate biological control strains for crown gall control on grape. Some of the more recent research on biological control of grape crown gall included nontumorigenic *A. vitis* strain E26 (Liang et al. (1990) Acta Microbio Sin 30:165-171) and strain VAR03-1 (Kawaguchi et al. (2008) Phytopathology 98:1218-1225). Other strains including *Rahnella aquatilis* strain HX2 (Chen et al. (2007) Plant Disease 91: 957-963), *Serratia plymuthica* strain IC1270, *Pseudomonas fluorescens* strain Q8r1-96, *P. fluorescens* strain B-4117 (Dandurishvili et al. (2010) Journal of Applied Microbiology 110: 341-352) and others were shown to provide various levels of grape crown gall inhibition under experimental conditions (Eastwell et al. (2006) Crop Protection 25:1191-1200).

Accordingly, there is a need in the art for effective controls of crown gall disease on grapevines. The present invention provides such a need.

SUMMARY OF THE INVENTION

The invention described herein relates to genetically engineered *Agrobacterium* strains (for example, *Agrobacterium vitis* F2/5) useful as a biological control agent for the prevention of crown gall disease caused by the infection of nursery stock and vineyards by many virulent strains of *Agrobacterium* such as *A. vitis*.

Accordingly, in general, the invention features genetic derivatives of a non-tumorigenic *Agrobacterium vitis* strain F2/5. In particular, such derivatives have a reduced ability to cause a necrosis of grape tissue while retaining biological control of crown gall disease. Identification of such derivatives is accomplished through standard methods such as those described herein.

In one aspect, the invention features a necrosis-minus, *Agrobacterium vitis* derivative of strain F2/5, wherein the derivative retains crown gall biological control. Exemplary derivatives are typically provided in an isolated or pure form. In one embodiment, the necrosis-minus *A. vitis* derivative of F2/5 has an inactivated gene encoding phosphopantetheinyl transferase (PPTase) (e.g., an inactivated homolog of *A. vitis* S4 (avi5813)), an inactivated gene encoding aminotransferase (e.g., an inactivated homolog of *A. vitis* S4 (avi4329)), an inactivated gene encoding iron response regulator (e.g., an inactivated rirA homolog of *A. vitis* S4 (avi0838)); or a combination thereof. Other genes of necrosis which may be inactivated to engineer a necrosis-minus *A. vitis* derivative of strain F2/5 include a member of transcriptional regulator LuxR family aviR (F-avi4374), a proteolytic subunit of ATP-dependent Clp protease clpP1(F-avi1696), nonribosomal peptide synthetase (F-avi3342) and polyketide synthase (F-avi4330). Methods for inactivating such genes in bacteria are well known in the art and include, without limitation, standard methods such as gene disruption by insertion of a DNA fragment and gene replacement in which the target gene is replaced by a select marker such as antibiotic resistance gene via double recombination at flanking regions of the target gene as well as the methods and biological control assays for analyzing such derivatives as is disclosed herein.

Exemplary sequences for *A. vitis* strain F2/5 related to necrosis and crown gall biological control are listed in Table 1.

TABLE 1

| | | |
|---|---|---|
| F-avi5813 | Nucleic acid (735 nucleotides) | SEQ ID NO: 1 |
| F-avi5813 | Protein (244 amino acids) | SEQ ID NO: 2 |
| F-avi4329 | Nucleic acid (1368 nucleotides) | SEQ ID NO: 3 |
| F-avi4329 | Protein (455 amino acids) | SEQ ID NO: 4 |
| F-avi0838 | Nucleic acid (471 nucleotides) | SEQ ID NO: 5 |
| F-avi0838 | Protein (156 amino acids) | SEQ ID NO: 6 |
| F-avi4374 | Nucleic acid (741 nucleotides) | SEQ ID NO: 7 |
| F-avi4374 | Protein (246 amino acids) | SEQ ID NO: 8 |
| F-avi1696 | Nucleic acid (633 nucleotides) | SEQ ID NO: 9 |
| F-avi1696 | Protein (210 amino acids) | SEQ ID NO: 10 |
| F-avi3342 | Nucleic acid (4005 nucleotides) | SEQ ID NO: 11 |
| F-avi3342 | Protein (1334 amino acids) | SEQ ID NO: 12 |
| F-avi4330 | Nucleic acid (7524 nucleotides) | SEQ ID NO: 13 |
| F-avi4330 | Protein (2187 amino acids) | SEQ ID NO: 14 |
| Avs locus | Nucleic acid (11899 nucleotides) | SEQ ID NO: 15 |
| P1388 | Nucleic acid (471 nucleotides) | SEQ ID NO: 16 |
| *A. vitis* strain F2/5 | Protein (156 amino acids) - transposase | SEQ ID NO: 17 |
| P1389 | Nucleic acid (1173 nucleotides) | SEQ ID NO: 18 |
| *A. vitis* strain F2/5 | Protein (390 amino acids) - hypothetical | SEQ ID NO: 19 |
| P1390 | Nucleic acid (1206 nucleotides) | SEQ ID NO: 20 |
| *A. vitis* strain F2/5 | Protein (401 amino acids) - multidrug resistant protein | SEQ ID NO: 21 |
| P1391 | Nucleic acid (1893 nucleotides) | SEQ ID NO: 22 |
| *A. vitis* strain F2/5 | Protein (630 amino acids) - siderophore synthetase | SEQ ID NO: 23 |

TABLE 1-continued

| | | |
|---|---|---|
| P1392 | Nucleic acid (1137 nucleotides) | SEQ ID NO: 24 |
| A. vitis strain F2/5 | Protein (378 amino acids) - tauropine dehydrogenase | SEQ ID NO: 25 |
| P1393 | Nucleic acid (1011 nucleotides) | SEQ ID NO: 26 |
| A. vitis strain F2/5 | Protein (336 amino acids) - cysteine synthetase | SEQ ID NO: 27 |
| P1394 | Nucleic acid (1398 nucleotides) | SEQ ID NO: 28 |
| A. vitis strain F2/5 | Protein (465) - diaminopimelate decarboxylase | SEQ ID NO: 29 |
| P1395 | Nucleic acid (501 nucleotides) | SEQ ID NO: 30 |
| A. vitis strain F2/5 | Protein (166 amino acids) | SEQ ID NO: 31 |
| P1396 | Nucleic acid (2154 nucleotides) | SEQ ID NO: 32 |
| A. vitis strain F2/5 | Protein (716 amino acids) - ferrichrome iron receptor | SEQ ID NO: 33 |
| P1397 | Nucleic acid (717 nucleotides) | SEQ ID NO: 34 |
| A. vitis strain F2/5 | Protein (238 amino acids) - transposase | SEQ ID NO: 35 |
| F-avi5730 | Nucleic acid (3879 nucleotides) | SEQ ID NO: 36 |
| F-avi5730 | Protein (1292 amino acids) | SEQ ID NO: 37 |

In another aspect, the invention features a biologically-pure culture including a necrosis-minus, *A. vitis* derivative of strain F2/5, wherein the derivative retains crown gall biological control. Exemplary derivatives are described herein.

In another aspect, the invention features a composition including a necrosis-minus, *A. vitis* derivative of strain F2/5, wherein the derivative retains crown gall biological control. Exemplary derivatives are described herein.

In still other aspects, the invention features a grapevine or grapevine component including a necrosis-minus, *A. vitis* derivative of strain F2/5, wherein the derivative retains crown gall biological control. Exemplary derivatives are described herein. In one embodiment, the grapevine component is a somatic embryo, a seed, a seedling, a scion, a rootstock, a cane, a cutting (e.g., a green cutting or a dormant cutting), a leaf, a stem, or a root. In another embodiment, the grapevine or grapevine component includes one or more of the F2/5 derivatives, described herein.

Exemplary grape plants for use in the practice of the invention include, but are not limited to, grapevines (for example, *Vitis* spp., *Vitis* spp. hybrids, and all members of the subgenera *Euvitis* and *Muscadinia*), including scion or rootstock cultivars. Exemplary scion cultivars include, without limitation, those which are referred to as table or raisin grapes and those used in wine production such as Cabernet Franc, Cabernet Sauvignon, Chardonnay (for example, CH 01, CH 02, CH Dijon), Merlot, Pinot Noir (PN, PN Dijon), Semillon, White Riesling, Lambrusco, Thompson Seedless, Autumn Seedless, Niagrara Seedless, and Seval Blanc. Other scion cultivars which can be used include those commonly referred to as Table or Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Caberet, Sauvignon, Calzin, Carignan, Charbono, Chardonnay, Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tarmat, Teroldico, Tinta Madeira, Tinto cao, Touriga, Traminer, Trebbiano Toscano, Trousseau, Valdepenas, Viognier, Walschriesling, White Riesling, and Zinfandel.

Rootstock cultivars that are useful in the invention include, without limitation, *Vitis rupestris* Constantia, *Vitis rupestris* St. George, *Vitis california*, *Vitis girdiana*, *Vitis rotundifolia*, *Vitis rotundifolia* Carlos, Richter 110 (*Vitis berlandieri*×*rupestris*), 101-14 Millarder et de Grasset (*Vitis riparia*×*rupestris*), Teleki 5C (*Vitis berlandieri*×*riparia*), 3309 Courderc (*Vitis riparia*×*rupestris*), Riparia Gloire de Montpellier (*Vitis riparia*), 5BB Teleki (selection Kober, *Vitis berlandieri*×*riparia*), SO$_4$ (*Vitis berlandieri*×*rupestris*), 41B Millardet (*Vitis vinifera*×*berlandieri*), and 039-16 (*Vitis vinifera*×*Muscadinia*). Additional rootstock cultivars which can be used include Couderc 1202, Couderc 1613, Couderc 1616, Couderc 3309, Dog Ridge, Foex 33EM, Freedom, Ganzin 1 (A×R #1), Harmony, Kober 5BB, LN33, Millardet & de Grasset 41B, Millardet & de Grasset 420A, Millardet & de Grasset 101-14, Oppenheim 4 (SO$_4$), Paulsen 775, Paulsen 1045, Paulsen 1103, Richter 99, Richter 110, Riparia Gloire, Ruggeri 225, Saint-George, Salt Creek, Teleki 5A, *Vitis rupestris* Constantia, *Vitis california*, and *Vitis girdiana*.

In still another aspect, the invention features a method for reducing crown gall disease on a grapevine or grapevine component, the method including administering to a grapevine or grapevine component an effective amount of a necrosis-minus, *A. vitis* derivative of strain F2/5, wherein the derivative retains crown gall biological control; a culture including a necrosis-minus, *A. vitis* derivative of strain F2/5, wherein the derivative retains crown gall biological control or a composition including a necrosis-minus, *A. vitis* derivative of strain F2/5, wherein the derivative retains crown gall biological control. Exemplary derivatives are described herein. In one embodiment, one or more of the bacterial derivatives, culture, or composition is administered at grafting time. In another embodiment, one or more of the bacterial derivatives, culture, or composition is administered on graft unions or the base of grapevine. In still another embodiment, one or more of the bacterial derivatives, culture, or composition is administered during field grafting of grapevine. In this case, the biocontrol agent is applied when vinyardists are top-grafting vines; a process that is used to change varieties in vineyards without removing current vines. In other embodiments, one or more of the bacterial derivatives, culture, or composition is administered to a dormant grapevine cutting. The biocontrol agent may also be applied to the basal end of each grafted or nongrafted vine to control crown gall and to stimulate callus and root formation. In certain embodiments, one or more of the bacterial derivatives, culture, or composition is administered to a dormant cane cutting or to a green shoot cutting. And in yet other embodiments, one or more of the bacterial derivatives, culture, or composition is administered to grapevine plant part above the ground (e.g., a trunk or cane). If desired, one or more of the necrosis-minus F2/5 derivatives is administered in any of the aforementioned embodiments.

In still another aspect, the invention features a method for reducing necrosis on a grapevine or grapevine component, the method including administering to a grapevine or grapevine component an effective amount of one or more of bacterial derivatives, cultures, or compositions described herein, wherein the method reduces necrosis on the grapevine or grapevine component. Administration of the derivative of F2/5, culture, or composition is administered at grafting time; for example, on graft unions or the base of grapevine. In other embodiments, administration occurs during field grafting of grapevine or to a dormant cane cutting prior to rooting. In other embodiments administration is to a green shoot cutting. Typically, the bacterial derivatives, culture, or composition, in this method, is administered to grapevine plant part which grows below the ground. If desired, one or more of the necrosis-minus F2/5 derivatives is administered in any of the aforementioned embodiments.

In still another aspect, the invention features a method for controlling crown gall disease, the method including administering to a locus for planting a grapevine or grapevine component an effective amount of the derivatives of F2/5, cultures, or compositions described herein, wherein the method controls crown gall disease. In one embodiment, the locus is a furrow or soil (e.g., the area where grape plants of a vineyard are to be planted). If desired, one or more of the necrosis-minus F2/5 derivatives is administered in any of the aforementioned embodiments.

In still another embodiment, the invention features a method for identifying an *A. vitis* F2/5 as a biocontrol agent for crown gall disease, the method including the steps of: a) administering the derivative of F2/5, culture, or composition to a grapevine or grapevine component; and b) assaying incidence of crown gall disease on the grapevine or grapevine component, wherein a reduction in crown gall disease compared to a control grapevine or grapevine component identifies the *A. vitis* strain F2/5 as a biocontrol agent for crown gall disease. In one embodiment, the *A. vitis* strain F2/5 is a biocontrol agent for crown gall disease on a grape plant part growing above the ground (e.g., where the grape plant part is a graft, trunk, or cane). Again, if desired, one or more of the necrosis-minus F2/5 derivatives is administered in any of the aforementioned embodiments.

In another aspect, the invention features a method for identifying an *A. vitis* F2/5 as a biocontrol agent for necrosis, the method including the steps of: a) administering any one of a derivative of F2/5, culture, or composition to a grapevine or grapevine component; and b) assaying incidence of necrosis on the grapevine or grapevine component, wherein a reduction in necrosis compared to a control grapevine or grapevine component identifies the *A. vitis* strain F2/5 as a biocontrol agent for necrosis. In one embodiment, the *A. vitis* strain F2/5 is a biocontrol agent for necrosis on a grape plant part growing below the ground (e.g., where the grape plant part is a root or callus). And still again, if desired, one or more of the necrosis-minus F2/5 derivatives is administered in any of the aforementioned embodiments.

In another aspect, the invention features a method for identifying an *A. vitis* F2/5 to promote callus development, the method including the steps of: a) administering any one of a derivative of F2/5, culture, or composition to a grapevine or grapevine component; to a grapevine or grapevine component; and b) assaying callus development on the grapevine or grapevine component, wherein an increase in callus development compared to a control grapevine or grapevine component identifies the *A. vitis* strain F2/5 promoting callus development.

In still another embodiment, the invention features a method for identifying an *A. vitis* F2/5 to promote root development, the method including the steps of: a) administering any one of a derivative of F2/5, culture, or composition to a grapevine or grapevine component; and b) assaying root development on the grapevine or grapevine component, wherein an increase in development compared to a control grapevine or grapevine component identifies the *A. vitis* strain F2/5 promoting root development.

In another aspect, the invention features a method of producing an *A. vitis* resistant vineyard, the method including the steps of: a) administering at least one necrosis-minus necrosis, *A. vitis* strain F2/5, wherein the *A. vitis* F2/5 retains crown gall biological control to a grapevine or grapevine component; b) planting the grapevine or grapevine component; c) growing the grapevine or grapevine component to establish the *A. vitis* resistant vineyard. In certain embodiments, administration of the derivative of F2/5 occurs in the vineyard. The invention accordingly features a vineyard produced according to this method. The invention further features a product derived from a grapevine produced in the vineyard. Such products include grapes, raisins, or other foodstuffs or beverages such as wine or juice.

In another aspect, the invention features a method of engineering a necrosis-minus derivative of *A. vitis* F2/5, the method including the steps of: a) introducing into an *A. vitis* F2/5 bacterium a construct which inactivates a gene which induces grape necrosis; and b) determining whether the *A. vitis* F2/5 induces grape necrosis, wherein a reduction in grape necrosis compared to a control *A. vitis* F2/5 is taken as identifying a necrosis-minus derivative of *A. vitis* F2/5. In one embodiment, the gene encodes a PPTase, an aminotransferase or is a homolog of iron response regulator, rirA. Exemplary genes are described herein including homologs of *A. vitis* S4 avi5813, avi4329, avi0838, avi4374, avi3342, avi1696, or avi3342. In certain embodiments, the gene includes a deletion of all or part of the gene with a suicide vector.

In another embodiment, the invention features a method for promoting callus development, the method including administering to a grapevine or grapevine component an effective amount of any one of a derivative of F2/5, culture, or composition, wherein the method promotes callus development on the grapevine or grapevine component.

In yet another aspect, the invention features a method for promoting root development, the method including administering to a grapevine or grapevine component an effective amount of any one of a derivative of F2/5, culture, or composition, wherein the method promotes root development on the grapevine or grapevine component.

In still another aspect, the invention features a method for reducing necrosis, the method includes administering to a grapevine or grapevine component an effective amount of any one of a derivative of F2/5, culture, or composition, wherein the method reduces necrosis of grapevine or grapevine component tissue growing below ground.

In still other aspects, the invention features an *A. vitis* bacterium attenuated by a non-reverting mutation in one or more of the PPTase gene (avi5813), the aminotransferase gene (avi4329), and the iron-responsive regulator gene, rirA (avi0838) or a functional homolog of the PPTase gene, aminotransferase gene, or the iron-responsive regulator gene. Such a bacterium is a non-tumorigenic *A. vitis*, for example, the F2/5 strain. In some embodiments, the invention includes a method for reducing crown gall disease on a grapevine or grapevine component, the method including administering to the grapevine or grapevine component an effective amount of these described *A. vitis* strains.

In another aspect, the invention features an engineered *Agrobacterium* bacterium including (a) one or more recombinant genes encoding (i) a sequence including SEQ ID NO: 19 or a functional homolog, (ii) a multidrug resistance protein B (SEQ ID NO: 21) or a functional homolog, (iii) a siderophore synthetase (SEQ ID NO: 23) or a functional homolog, (iv) a tauropine dehydrogenase (SEQ ID NO: 25) or a functional homolog, (v) a cysteine synthetase (SEQ ID NO: 27) or a functional homolog, (vi) diaminopimelate decarboxylase (SEQ ID NO: 29) or a functional homolog, (vii) a sequence including SEQ ID NO: 31 or a functional homolog, or (viii) a ferrichrome-iron receptor (SEQ ID NO: 33) or a functional homolog; and optionally (b) one or more recombinant genes encoding a transposase or a functional homolog. In some embodiments of the engineered *Agrobacterium* bacterium, the one or more recombinant genes encoding one or more recombinant proteins encode at least one protein listed in FIG. 5A or a functional homolog of at least one protein listed in FIG. 5A. In some embodiments of the engineered *Agrobacterium* bacterium, expression of an operon including at least a siderophore synthetase or a ferrichrome-iron receptor is controlled by a recombinant promoter, and wherein the promoter is constitutive or inducible. In some other embodiments of the engineered *Agrobacterium* bacterium, the *Agrobacterium* is a non-tumorgenic *A. vitis*, for example, *A. vitis* F2/5. Typically, the engineered *Agrobacterium* bacterium is necrosis minus Such engineered bacteria are useful for controlling crown gall disease; in particular, biological control.

In other aspects, the invention features an engineered *Agrobacterium* bacterium including one or more recombinant gene encoding a sequence including SEQ ID NO: 37. In some embodiments, the engineered *Agrobacterium* bacterium is a non-tumorgenic *A. vitis*.

In other aspect, the invention features a method for producing an *Agrobacterium* species having biological control on grapevine, the method including the steps of (a) providing a non-tumorigenic *Agrobacterium* species having a control of crown gall disease negative phenotype; and (b) introducing into the *Agrobacterium* species a sequence including one or more recombinant genes encoding (i) a sequence including SEQ ID NO: 19 or a functional homolog, (ii) a multidrug resistance protein B (SEQ ID NO: 21) or a functional homolog, (iii) a siderophore synthetase (SEQ ID NO: 23) or a functional homolog, (iv) a tauropine dehydrogenase (SEQ ID NO: 25) or a functional homolog, (v) a cysteine synthetase (SEQ ID NO: 27) or a functional homolog, (vi) diaminopimelate decarboxylase (SEQ ID NO: 29) or a functional homolog, (vii) a sequence including SEQ ID NO: 31 or a functional homolog, or (viii) a ferrichrome-iron receptor (SEQ ID NO: 33) or a functional homolog; and optionally, (viiii) a sequence including SEQ ID NO: 37 or a functional homolog thereof.

In other embodiments, the invention features an isolated and purified nucleic acid molecule, obtainable from *A. vitis*, which consists of at least one gene capable of conferring biological control of crown gall phenotype upon a genetically engineered microorganism, wherein the nucleic acid molecule is contained in the within a locus referred to herein as Avs (SEQ ID NO: 15). In some embodiments, the invention features a plasmid containing such a nucleic acid molecule. In other embodiments, the invention includes a genetically engineered *Agrobacterium* bacterium having stably and functionally incorporated therein the nucleic acid molecule. Typically, the *Agrobacterium* bacterium is *A. vitis* F2/5 such as a derivative that is necrosis minus.

In another aspect, the invention features an isolated nucleic acid molecule, wherein the isolated nucleic acid molecule includes a nucleotide sequence substantially identical to any one of SEQ ID NOs: 1, 3, 5, 7, 9, 11, 13, 15, 16, 18, 20, 22, 24, 26, 28, 30, 32, 34, 36 as described in Table 1 and herein. Typically, nucleic acid molecule includes a heterologous nucleotide sequence that inactivates, diminishes, or abrogates expression of the isolated nucleic acid molecule.

In another aspect, the invention features an isolated nucleic acid molecule, wherein the isolated nucleic acid molecule includes a nucleotide sequence that encodes an amino acid sequence substantially identical to any one of SEQ ID NOs: 2, 4, 6, 8, 10, 12, 14, 17, 19, 21, 23, 25, 27, 29, 31, 33, 35, 37 as described in Table 1 and herein.

In another aspect, the invention features an engineered *Agrobacterium* bacterium, wherein the bacterium includes any one of the isolated nucleic acid molecules having a sequence according to SEQ ID NOs: 1, 3, 5, 7, 9, 11, 13, 15, 16, 18, 20, 22, 24, 26, 28, 30, 32, 34, 36 as described in Table 1 and herein.

By "substantially identical" is meant an amino acid sequence or nucleic acid sequence that exhibits at least 50% identity to a reference sequence. Such a sequence is generally at least, e.g., 50%, 60%, 70%, 75%, 80%, 85%, 90%, 95%, 96%, 97%, 98%, or 99% identical at the amino acid level or nucleic acid level to a reference sequence. In general, for polypeptides, the length of comparison sequences can be at least five amino acids, e.g., 10, 20, 30, 40, 50, 60, 70, 80, 90, 100, 125, 150, 175, 200, 250, 300, or more amino acids, up to the entire length of the polypeptide. For nucleic acids, the length of comparison sequences can generally be at least 10, 20, 30, 40, 50, 60, 70, 80, 90, 100, 125, 150, 175, 200, 250, 300, 400, 500, 600, 700, 800, 900, or more nucleotides, up to the entire length of the nucleic acid molecule. It is understood that for the purposes of determining sequence identity when comparing a DNA sequence to an RNA sequence, a thymine nucleotide is equivalent to a uracil nucleotide.

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined in various ways that are within the skill in the art, for instance, the Smith Waterman alignment algorithm (Smith et al., J. Mol. Biol. 147:195-7, 1981) and BLAST (Basic Local Alignment Search Tool; Altschul et al., J. Mol. Biol. 215: 403-10, 1990). These and other alignment algorithms are accessible using publicly available computer software such as "Best Fit" (Smith and Waterman, Advances in Applied Mathematics, 482-489, 1981) as incorporated into GeneMatcher Plus™ (Schwarz and Dayhof, Atlas of Protein Sequence and Structure, Dayhoff, M. O., Ed pp 353-358, 1979), BLAST, BLAST-2, BLAST-P, BLAST-N, BLAST-X, WU-BLAST-2, ALIGN, ALIGN-2, CLUSTAL, or Megalign (DNASTAR). In addition, those skilled in the art can determine appropriate parameters for measuring alignment, including any algorithms needed to achieve optimal alignment over the length of the sequences being compared.

The invention provides significant advantages for viticulturists, vineyardists, and grape nurserymen among others. Crown gall causes significant economic loss in nurseries worldwide. Application of derivatives of F2/5 offers great promise for controlling this disease and for improving survival and quality of grapevines in the nursery as well as in vineyards. The invention is especially advantageous because the disclosed necrosis-minus necrosis, *A. vitis* strain F2/5, which retains crown gall biological control minimizes necrosis. Furthermore, this biocontrol agent is not detrimental to grafting, callus formation and rooting of grapevines. Indeed, such bacteria enhance callus and root formation on grapes.

Other features and advantages of the invention will be apparent from the following Drawings, Detailed Description, and Claims.

BRIEF DESCRIPTION OF DRAWINGS

FIG. 1 shows crown gall at wounds on woody grape tissues inoculated with CG49 or CG49 mixed with F2/5 or with F2/5 mutants. Arrows point to inoculated wound sites.

FIG. 2 shows dormant grape cuttings were soaked in suspensions of F2/5, F2/5 mutants or water and then rooted. Arrows point to necrosis on roots.

FIG. 3 shows effects of F2/5 and three necrosis-minus derivatives of F2/5 on grape shoot necrosis.

FIG. 4 shows effects of treatments with *A. vitis* F2/5 and its mutants on grapevine grafts

FIGS. 6A through 6P show the sequences listed in Table 1.

DETAILED DESCRIPTION

Figure 5A:
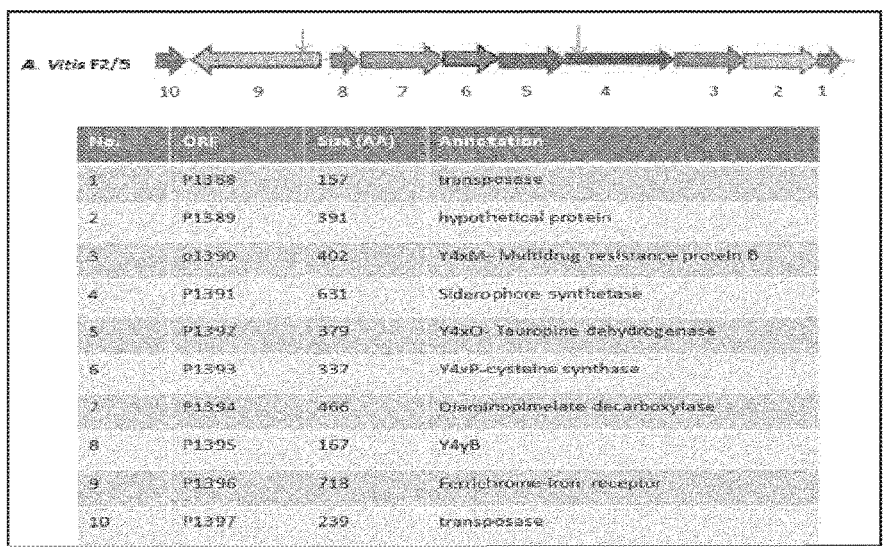
FIGS. 5A and 5B show the gene organization and annotation of Avs locus (A) and the effects of knock-down mutant ΔP1391 and ΔP1396 on biological control (B).

Crown gall of grapevines is caused by the bacterium, *Agrobacterium vitis*. The disease is initiated at wound sites, such as graft unions and freeze injuries and limits grape production worldwide. There are no chemical or biological controls that have been successful to control this disease to date. A non-tumorigenic strain of *A. vitis*, F2/5, prevents crown gall on grapevines at wounds but also causes a necrosis that can be deleterious to graft union development and to root formation. *A. vitis* strain F2/5 is publically available from a number of laboratories throughout the world including from the laboratory of the Applicant's inventor, Dr. Thomas J. Burr (Department of Plant Pathology & Plant-Microbe Biology, New York State Agricultural Experiment Station, Cornell University, A104 Barton Hall 630 W. North Street, Geneva, N.Y. 14456-0462). As is disclosed herein, specific necrosis-minus derivatives of F2/5 that still retain biological control activities have been engineered. One mutant was generated by knocking out of a gene encoding phosphopantetheinyl transferase (PPTase), which is required for post-translational modification of polyketide synthase and non-ribosomal peptide synthase genes; another mutant was generated through the disruption of an aminotransferase; yet another mutant was targeted at an iron-response regulator. These mutations result in abolished necrosis but did not affect the ability of F2/5 to function as a biological control agent.

Such strains may be used in nurseries at grafting time (on graft unions and base of plants) as well as during field grafting of vines to prevent crown gall. Other uses are described herein.

The following examples are intended only to further illustrate the invention and are not intended to limit the scope of the invention as defined by the claims.

Example 1

Development of *Agrobacterium vitis* F2/5 Mutants:

Mutants of specific genes were generated through disruption with suicide vector pVIK165 (Kalogeraki et al. (1997) Gene 188: 69-75). Internal fragments of specific target genes were amplified from F2/5 genomic DNA with corresponding primer pairs. The specific genes that were mutated and primers used to amplify internal gene fragments are listed in the Table 2.

TABLE 2

Genes mutated and primers used in generation of the mutants

| Gene targeted | primer name | primer sequence* | size of fragment amplified |
|---|---|---|---|
| F-avi5813 (PPTase) | avi5813-F: avi5813-R: | 5'-AA<u>GAATTC</u>TTGATCTCGCATCGCGCTG-3' 5'-AA<u>TCTAGA</u>TGCGCTGTCATGACCTGTTCTG-3' | 336 bp |
| F-avi4329 (amino-transferase) | avi4329-F: avi4329-R: | 5'-AC<u>GAGCTC</u>AGCTCGTCAGCGAGCAGCTG-3' 5'-AG<u>TCTAGA</u>TGAACTCGTCATGGATCACCAG-3' | 382 bp |
| F-avi0838 (rirA) | avi0838-F avi0838-R | 5'-AC<u>GAGCTC</u>TGCCAAGGCCTGTGGTGTCTC-3' 5'-AG<u>TCTAGA</u>TGTCGATCAACGGGCAATCGAC-3' | 224 bp |

*Restriction sites are underlined

XbaI and SacI restriction sites were introduced into forward and reverse primers respectively. PCR products were purified, digested and then ligated into suicide vector pVIK165 at XbaI and SacI sites. The constructs were transformed into *E. coli* strain S17-1/λpir by electroporation and transformants were selected on Luria-Bertani agar amended with kanamycin (50 μg/ml). After verification by sequencing, the constructs were transferred to F2/5 via conjugal mating and gene disruptions occurred following single homologous recombination. Derivatives of F2/5 were selected on AB minimal medium amended with 10% mannitol and kanamycin (50 µg/ml). Mutations were verified by PCR using primers derived from sequences of the F2/5 chromosome that flank the insertion site and sequence from the pVIK165 vector. Derivatives were then tested for their ability to prevent crown gall formation as described below.

Biological Control Assays:

F2/5 derivatives, Δ F-avi5813, Δ F-avi4329 and Δ F-avi0838, which are all grape necrosis-minus, were tested for their ability to prevent crown gall on potted 1- to 2-month-old grapevines (*V. vinifera* cv. Chardonnay) in the greenhouse. Avi numbers correspond to gene homologs in the *A. vitis* S4 genome as described in the literature (see, for example, http://agro.vbi.vt.edu/public/index.html) (Slater et al., J. Bacteriol. 191:2501-11 (2009).). F2/5, derivatives of F2/5, and tumorigenic *A. vitis* strain CG49 were grown overnight on Potato Dextrose Agar (PDA) or PDA plus kanamycin and suspended in sterile distilled water and adjusted to $OD_{600}=0.1$ (corresponding to about $10^8$ cells/ml). F2/5 and derivatives of F2/5 were mixed 1:1 with CG49, and 50 µl of the mixed suspensions were inoculated on slice wounds made with a scalpel on woody trunks and/or green shoot tissues of the potted grapevines. Wounds were made just below a side shoot on woody tissue and below a bud on green shoots. After inoculum suspensions dried, the wound sites were wrapped with Parafilm. In general eight plants were inoculated for each treatment and experiments were repeated. The number of inoculation sites at which galls developed was recorded at least 6 weeks after inoculation for green shoots and 8 weeks for woody cutting tissue (Table 3 and FIG. 1). The necrosis-minus derivatives of F2/5 maintained their biological control activity.

TABLE 3

Biological control of crown gall in grapevine with F2/5 and F2/5 mutants

| Treatment | Experiment[b] | Gall[c]/Inoculations | Average gall size[d] (mm²) |
|---|---|---|---|
| CG49 | T-1 | 8/8 | 217.45 |
| | T-2 | 8/8 | 141.78 |
| | T-3 | 8/8 | 175.21 |
| | T-4 | 6/6 | 203.75 |
| CG49 + F2/5 | T-1 | 0/8 | |
| | T-2 | 0/8 | |
| | T-3 | 0/8 | |
| | T-4 | 0/6 | |
| CG49 + Δavi0838 (rirA)[a] | T-1 | 0/8 | |
| | T-2 | 2/8 | >10 |
| | T-3 | 1/9 | 170.10 |
| | T-4 | 3/12 | 28.98 |
| CG49 + Δavi4329 (amino-transferase) | T-1 | 2/8 | 92.45 |
| | T-2 | 1/8 | 33.50 |
| | T-3 | 1/8 | 145.92 |
| | T-4 | 4/10 | 27.04 |
| CG49 + Δavi5813 (PPTase) | T-1 | 0/8 | |
| | T-2 | 0/8 | |
| | T-3 | 0/8 | |
| | T-4 | 4/12 | 21.84 |

[a]avi numbers correspond to genes annotated in the *A. vitis* strain S4 genome sequence
[b]T-1, experiment initiated on Dec. 6, 2011; T-2. initiated on Dec. 13, 2011; T-3, initiated on Dec. 19, 2011; T-4 initiated on Jan. 28, 2012.
[c]"Gall" on the avi0838, avi4329 and avi5813 mutants treated vines may be callus development and not crown gall.
[d]The average gall size is calculated as total gall size/gall number instead of inoculation number.

Effect of F2/5 and Derivatives of F2/5 on Necrosis, Root and Callus Development:

Dormant grapevine cuttings were inoculated with strain F2/5 and derivatives of F2/5, ΔF-avi5813), ΔF-avi4329 and ΔF-avi0838 by submersing basal ends of cuttings in water suspensions of the bacteria (about $10^8$ cfu/ml) for 4 hours prior to planting them in perlite to initiate callus and rooting. Data on necrosis, callus and root development and incidence of crown gall infection were collected 8 weeks after inoculation (Table 4 and FIG. 2). Cuttings treated with necrosis-minus derivatives produced enhanced roots and callus and lacked the significant necrosis seen on F2/5 treated cuttings.

TABLE 4

Effect of F2/5 and derivatives on root and callus development and on the level of necrosis on roots.
Phenotypes were rates as 0-2 for necrosis (2 being more than 90% of roots having necrosis, 0-3 for root development with a 3 having the largest root mass and 0-3 for callus development with 3 equalling the largest amount of callus development at the cutting base.

| Treatment/Response | F2/5 | Water | ΔF-avi0838 (rirA) | ΔF-avi4329 (amino-transferase) | ΔF-avi 5813 (PPTase) |
|---|---|---|---|---|---|
| Necrosis (0-2) | 2 | 0.1 | 0.3 | 0.2 | 0.3 |
| Root development (0-3) | 1.5 | 1.5 | 1.9 | 1.9 | 1.7 |
| Callus development (0-3) | 0.3 | 1.5 | 2.3 | 2.2 | 1.7 |

On young stem explants, it was also shown that derivatives of F2/5 are necrosis-negative (FIG. 3).

SUMMARY

Crown gall is a significant disease of grapevines that often is initiated at grafts. Grafting may be done in the nursery (scion grafted onto rootstocks) or in the field when changing varieties of an established vineyard. Strain F2/5 is able to prevent the development of crown gall at wound sites on grapevines however is detrimental to graft take. As shown in FIG. 2, F2/5 is also detrimental to root formation. This is likely due to the fact that F2/5, like other *A. vitis* strains, initiates a necrosis of certain grape tissues.

Mutations in specific genes of strain F2/5 to generate F2/5 derivatives that no longer cause necrosis but have maintained biological control function were generated. These results have been repeatedly confirmed in the greenhouse as presented herein. In some cases small galls develop when the derivatives are applied together with a tumorigenic *A. vitis* strain (CG49) however the degree of galling is greatly reduced and, in most cases, no gall forms.

It was also observed that when dormant cuttings were treated with the mutants compared to the wildtype F2/5 strain, necrosis on roots was absent, an increased amount of roots were formed and increased callus at the base of the cuttings was noted. This is significant because the treatment is therefore beneficial to use even on grape cuttings that are not grafted. For example certain American and hybrid varieties are not grafted on rootstocks but rather grown on their own roots. Therefore treatment of such varieties with the F2/5 mutants may be advantageous in stimulating callusing and root development.

Example 2

Mutants that Display a Necrosis-Minus Phenotype and Remain Biological Control Positive:

Effects of F2/5 Necrosis-Minus Mutants on Grapevine Graft Take

Effects of F2/5 and the mutant ΔF-avi5813 (PPTase), ΔF-avi4329 (aminotransferase) and ΔF-avi0838 (rirA) on graft take and root or shoot development were determined by treatment of grapevine cuttings (Cabernet Franc) with the bacterial suspensions. Bacterial strains were grown on PDA or PDA amended with kanamycin (50 μg/ml) for 48 hr. The bacterial cells were suspended in water and adjusted to be OD=0.1. Dormant woody cuttings were cut with an omega graft tool. Following cutting the cut surfaces were dipped in bacterial suspensions and then fitted together and wrapped with Parafilm. The cuttings were planted in greenhouse potting mixture and kept moist until analyzed.

TABLE 5

Effects of *A. vitis* F2/5 and mutants on grapevine grafts

| Treatment | Vines that formed shoots* | Root formation on plants | Graft take (%) | Root necrosis |
|---|---|---|---|---|
| Water | 8/11 (72.7%) | 7 with roots, all from rootstock 1 without roots | 87% | + |
| F2/5 | 9/12 (75.0%) | 8 with roots, all from graft sites 1 without roots | 0 | ++ |
| CG49 | 5/12 (41.7%) | 4 with roots, 3 from graft sites and 1 from rootstock, 1 without roots | 20% | ++ |
| ΔF-avi5813 (PPTase) | 10/14 (71.4) | 10 with roots, 8 from rootstock and 2 from graft sites | 80% | − |
| ΔF-avi0838 (rirA) | 10/19 (52.6%) | 9 with roots, 6 from rootstock and 3 from graft sites, 1 without root | 66% | − |
| ΔF-avi4329 (aminotransferase) | 9/14 (64.3%) | 9 with roots, 7 from rootstock and 2 from graft sites | 77% | − |
| F2/5 + CG49 | 7/18 (38.9%) | 5 with roots, all from graft sites 2 without roots | 0 | ++ |
| ΔF-avi5813 + CG49 | 15/18 (83.3%) | 14 with roots,12 from rootstock and 2 from graft sites, 1 without root | 85% | − |
| ΔF-avi0838 + CG49 | 8/13 (61.5%) | 8 with roots, 4 from rootstock and 4 from graft sites | 50% | − |
| ΔF-avi4329 + CG49 | 8/13 (61.5%) | 8 with roots, 4 from rootstock and 4 from graft sites | 50% | − |

−, no root necrosis;
++, heavy roots necrosis
*Cuttings had single buds. Some buds did not grow and therefore the plants did not develop as shown in results.

The results indicate that the mutants improve graft take and root growth as compared to strain F2/5, tumorigenic strain CG49, or CG49 combined with F2/5 (FIG. 4 and Table 5). The roots from cuttings treated with the mutants grow with no or less necrosis and produce more roots (FIG. 4). Graft take was increased in mutant treatments as compared to F2/5, CG49 or CG49 and F2/5 (Table 5).

*A. vitis* F2/5 Genes Required for Biological Control but not for Necrosis: Avs Locus and F-avi5730

Avs Locus

Figure 5B:

The Avs locus as being unique to *A. vitis* strain F2/5 as no homologous loci present have been identified in other *A. vitis* strains using PCR screens. The Avs locus is approximately 12 kb in length and contains 10 ORFs that are flanked by two genes putatively encoding transposases (FIG. 5A) thereby suggesting horizontal gene transfer as a potential means of inquiry by F2/5. The DNA sequences and deduced amino acid sequences of the genes within Avs locus are shown in FIG. 5. Mutation of either gene P1391 encoding a siderophore synthase or gene P1396 encoding a siderophore ferrichrome-iron receptor resulted in loss of biological control activity by F2/5 (FIG. 5B). All of the genes listed in FIG. 5A are common in *A. vitis* strains except for those that reside in the Avs locus. Accordingly, one or more genes of the Avs locus is useful for generating new biological control strains by transferring it and expressing in non-tumorigenic *A. vitis* strains. Exemplary non-tumorigenic *A. vitis* strains are described in Burr et al. (1999) Plant Disease 83:102-107. Examples of such non-tumorigenic strains are nontumorigenic *A. vitis* from *Vitis riparia* (CG511, CG515, CG517, CG518, CG523, CG526, CG529, CG531, CG535, CG537, CG538, CG542, and CG544), nontumorigenic *A. vitis* from *V. riparia* (CG546, CG548, CG550, CG553, CG555, CG556, CG559, CG561, and CG565), nontumorigenic *A. vitis* from *V. riparia* (CG567, CG569, CG571, and CG572), nontumorigenic *A. vitis*, biocontrol for grape crown gall (F2/5), and nontumorigenic *A. rhizogenes*, biocontrol strain (K-84).

NRPS (F-avi5730)

A non-ribosomal peptide synthase (NRPS) gene (F-avi5730) in F2/5 as being required for biological control but not for necrosis was also identified. Avi5730 in F2/5 was mutagenized by gene disruption. The F-avi5730 (residing on chromosome II) mutant did not affect grape necrosis. Gene disruption also resulted in loss of biological control similar to results described above for disruption of the P1391 encoding the siderophore synthase and disruption of P1396 encoding the siderophore ferrichrome-iron receptor. Like Avs and its genes, the NRPS is useful for generating new biological control strains by transferring it and expressing in non-tumorigenic *A. vitis* strains.

Use

Exemplary uses of any of the engineered strains of *Agrobacterium* described herein are as follows.

Methods and rates of application of a necrosis-minus, non-tumorigenic *Agrobacterium* sp. such as a mutant derivative of *A. vitis* F2/5 which retains biological control of crown gall disease (for example, the PPTase, rirA, and aminotransferase gene mutants described herein) is accomplished according to standard practices known in the art. Typically, bacteria are applied as a dip solution (such as an inoculant) to any grapevine or grapevine component (grapevine component is a somatic embryo, a seed, a seedling, a scion, a rootstock, a cane, a cutting (e.g., a green cutting or a dormant cutting), a leaf, a stem, or a root in, for example, laboratories, nurseries, greenhouses, or in vineyards.

For purposes of the present invention, the bacteria are used as formulations or compositions. Such formulations or compositions contain one or more bacterium described herein and optionally a carrier. The carrier component can be a liquid or a solid material for delivering the formulation or composition to a desired site on a grapevine or grapevine component. Liquids suitable as carriers include water, and any liquid which will not affect the viability of the bacteria. Similarly, solid carriers can be virtually anything that is non-toxic to the bacterium. Non-limiting examples of solid carriers include peat, vermiculite, perlite, and soil or any other material used in commercial propagation of grape. Bacteria may be lyophilized or in powder form prepared according to standard methods known in the art.

Bacteria are administered according to standard practices for applying compositions to grapevine, grapevine component, or for application to a locus for planting a grapevine or a grapevine component such as soil. By the term "effective amount" or "amount effective for" is meant that minimum amount of a bacterial composition or bacterial formulation needed to at least reduce, or substantially eliminate crown gall disease on a grapevine or a grapevine component when compared to an untreated grapevine or grapevine component. Similarly, the terms refer to the minimum amount of bacteria needed to reduce necrosis or to promote callus or root development or both. The precise amount needed will vary in accordance with the particular bacterial composition used; the grapevine or grapevine component to be treated; and the environment in which the grapevine or grapevine component is located. The exact amount of bacteria in a composition needed can easily be determined by one having ordinary skill in the art given the teachings of the present specification. The examples herein show typical concentrations which will be needed to at least reduce crown gall disease as well as for promoting callus and root development.

In some embodiments, the active ingredient of a solid formulation is a necrosis-minus, biological control positive derivative of *A. vitis* F2/5 (e.g., the PPTase, rirA and aminotransferase gene mutants described herein or any combination of these derivatives) that includes not less than 1,000 million colony forming units (cfu) per gram of moist peat medium. For preparation, 100 grams of solid formulation when mixed with 1 gallon of water typically provides a suspension of approximately $2.6 \times 10^7$ (cfu) per milliliter in a dip solution.

In other embodiments, the active ingredient of a liquid formulation is a necrosis-minus, biological control positive derivative of *A. vitis* F2/5 that includes not less than 1,000 million cfu per milliliter of water.

Plants are typically dipped in a solution of a necrosis-minus, biological control positive derivative of *Agrobacterium* sp. such as any one of the mutant derivative of *A. vitis* F2/5 described herein. Alternatively, the formulation or composition is sprayed on a plant; for example, by spraying to graft surfaces during grafting. In other applications, the formulation or composition is applied to a locus where the plant is growing or to be planted.

Compositions and formulations are applied to grapevine or grapevine components as needed according to standard viticultural methods. The compositions can be applied as needed to any plant wound or damaged plant tissue that allows entry of a tumorigenic *A. vitis* sp. Typically, such applications may be sprayed or painted on the plant. In other situations, applications of the compositions or formulations would be to grafts at time of grafting. This would be most typically done in a nursery as well as in field grafting. An exemplary grafting situation is where a grower changes varieties in the vineyard by grafting to a current vine, for example, changing from Riesling to Chardonnay by field grafting. For example, for grafting applications, grapevine or grapevine components should be treated with the bacteria after cutting or other handling operations that damage plant tissue and before and after cold storage. Bare rootstock or scion material should be dipped or sprayed with the formulation solution until all root surfaces or scion surfaces or the stem above the graft union are completely wet, or spray these tissues to runoff.

Grapevines or grapevine components may also be treated with a formulation or composition before and after cold storage or at both times.

Because the strains described herein also enhance callus and rooting of dormant cuttings, the bacteria useful in the nursery for rooting purposes. This is beneficial on grafted and non-grafted varieties. For example, many of grape hybrids and labrusca varieties are not grafted but callusing and rooting is important for regeneration. Another exemplary use involves a grower to dip rooted and grafted (or non-grafted) vines obtained from a nursery in a formulation or composition prior to planting. Such treatments would enhance growth in the vineyard.

Any of the genes described herein are useful for engineering *A. vitis* strains (tumorigenic and non-tumorgenic alike) to necrosis minus phenotype and crown gall positive phenotype. Methods for engineering such strains are according to standard methods in the art including those described herein.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth.

All publications are herein incorporated by reference in their entirety to the same extent as if each individual publication, patent or patent application was specifically and individually indicated to be incorporated by reference in its entirety.

What is claimed is:

1. An isolated, necrosis-minus, *Agrobacterium vitis* derivative of strain F2/5, said derivative comprising a nucleic acid molecule encoding an aminotransferase comprising 95% sequence identity to SEQ ID NO:4, wherein expression of said aminotransferase is diminished or abrogated.

2. The *A. vitis* of claim 1, wherein said nucleic acid molecule is inactivated.

3. The *A. vitis* of claim 2, wherein said aminotransferase is a homolog of *A. vitis* S4 (avi4329).

4. A culture comprising the *A. vitis* of claim 1.

5. A composition comprising the *A. vitis* of claim 1.

6. A method for reducing crown gall disease on a grapevine or a grapevine component, said method comprising administering to said grapevine or grapevine component an effective amount of the *A. vitis* of claim 1, wherein said method reduces crown gall disease on said grapevine or grapevine component.

7. The method of claim 6, wherein said *A. vitis*, culture, or composition is administered at grafting time; is administered on graft unions or the base of the grapevine; is administered during field grafting of grapevine; is administered to a dormant cane cutting; composition is administered to a green shoot cutting; or is administered to a grapevine plant part above the ground.

8. A method for reducing necrosis on a grapevine or a grapevine component, said method comprising administering to said grapevine or grapevine component an effective amount of the *A. vitis* of claim 1, wherein said method reduces necrosis on said grapevine or grapevine component.

9. A method for controlling crown gall disease, said method comprising administering to a locus for planting a grapevine or grapevine component an effective amount of the *A. vitis* of claim 1, wherein said method controls crown gall disease.

10. The method of claim 9, wherein said locus is a furrow or soil.

11. A method for promoting callus development, said method comprising administering to a grapevine or grapevine component an effective amount of the *A. vitis* of claim 1, wherein said method promotes callus development on said grapevine or grapevine component.

12. A method for promoting root development, said method comprising administering to a grapevine or grapevine component an effective amount of the *A. vitis* of claim 1, wherein said method promotes root development on said grapevine or grapevine component.

13. A method for reducing necrosis, said method comprising administering to a grapevine or grapevine component an effective amount of the *A. vitis* of claim 1, wherein said method reduces necrosis of grapevine or grapevine component tissue below ground.

14. The *A. vitis* of claim 1, wherein said aminotransferase comprises 96% sequence identity to SEQ ID NO:4.

15. The *A. vitis* of claim 1, wherein said aminotransferase comprises 97% sequence identity to SEQ ID NO:4.

16. The *A. vitis* of claim 1, wherein said aminotransferase comprises 98% sequence identity to SEQ ID NO:4.

17. The *A. vitis* of claim 1, wherein said aminotransferase comprises 99% sequence identity to SEQ ID NO:4.

18. The *A. vitis* of claim 1, wherein said aminotransferase comprises SEQ ID NO:4.

* * * * *

SEQUENCE LISTING

<160> NUMBER OF SEQ ID NOS: 37

<210> SEQ ID NO 1
<211> LENGTH: 735
<212> TYPE: DNA
<213> ORGANISM: A. vitis strain F2/5
<220> FEATURE:
<221> NAME/KEY: misc_feature
<222> LOCATION: (1)..(735)
<223> OTHER INFORMATION: avi5813

<400> SEQUENCE: 1

```
atgagccagc gggccaataa tcaggtggaa atatactcct catgccctgt gcctccgctt      60
ttcgaggcct tcatctcgca tcgcgctgtt tgcttccgtc acaatgattt tacgcccgaa     120
gcggcgattg aacttggcgt gcccctgcca gaaagcatgg gaaaggcggt cgccaagcgc     180
aaggcggaat atgtgggcgg acggttctgc gccatggagg cgattgtggc gcaaaccggc     240
cagcctgccg caccgttac agcgggaccg cgtggcgaac cggtctggcc gtcagggctg      300
gtcggctcga ttacccatac gcacgggttt gctgcggcag ccgttgccga tgcagctcga     360
tttcgcagcc ttggcatgga tacagaacag gtcatgacga cgcaggtcat gggcaatgtc     420
cgagagcgga tctgcggtcc ggaagaccgg tttggggcca gcagctctct tttgccggaa     480
cttcatacca ccctggtgtt ttctgccaag gaaagcctgt tcaaatgtct ttatccattg     540
gttgaaaaaa tgttctggtt cgaagacgcg ctgatccgga tcgatccgga tcgggatggt     600
ctgtttaccg ccgaattgct gtcacgcctc catgtggaat ttccggcggg aacagtgatc     660
gaaggacgct tttgcctgac gccgggtctg gttcataccg gcatcagcct tgcgaaagat     720
gaggctgcgt tataa                                                      735
```

<210> SEQ ID NO 2
<211> LENGTH: 244
<212> TYPE: PRT
<213> ORGANISM: A. vitis strain F2/5
<220> FEATURE:
<221> NAME/KEY: MISC_FEATURE
<222> LOCATION: (1)..(244)
<223> OTHER INFORMATION: avi5813

<400> SEQUENCE: 2

```
Met Ser Gln Arg Ala Asn Asn Gln Val Glu Ile Tyr Ser Ser Cys Pro
1               5                   10                  15

Val Pro Pro Leu Phe Glu Ala Phe Ile Ser His Arg Ala Val Cys Phe
            20                  25                  30

Arg His Asn Asp Phe Thr Pro Glu Ala Ala Ile Glu Leu Gly Val Pro
        35                  40                  45

Leu Pro Glu Ser Met Gly Lys Ala Val Ala Lys Arg Lys Ala Glu Tyr
    50                  55                  60

Val Gly Gly Arg Phe Cys Ala Met Glu Ala Ile Val Ala Gln Thr Gly
65                  70                  75                  80

Gln Pro Ala Ala Pro Val Thr Ala Gly Pro Arg Gly Glu Pro Val Trp
                85                  90                  95

Pro Ser Gly Leu Val Gly Ser Ile Thr His Thr His Gly Phe Ala Ala
            100                 105                 110

Ala Ala Val Ala Asp Ala Ala Arg Phe Arg Ser Leu Gly Met Asp Thr
        115                 120                 125

Glu Gln Val Met Thr Ala Gln Val Met Gly Asn Val Arg Glu Arg Ile
    130                 135                 140
```

Cys Gly Pro Glu Asp Arg Phe Gly Ala Ser Ser Leu Leu Pro Glu
145                 150                 155                 160

Leu His Thr Thr Leu Val Phe Ser Ala Lys Glu Ser Leu Phe Lys Cys
                165                 170                 175

Leu Tyr Pro Leu Val Glu Lys Met Phe Trp Phe Glu Asp Ala Leu Ile
            180                 185                 190

Arg Ile Asp Pro Asp Arg Asp Gly Leu Phe Thr Ala Glu Leu Leu Ser
        195                 200                 205

Arg Leu His Val Glu Phe Pro Ala Gly Thr Val Ile Glu Gly Arg Phe
    210                 215                 220

Cys Leu Thr Pro Gly Leu Val His Thr Gly Ile Ser Leu Ala Lys Asp
225                 230                 235                 240

Glu Ala Ala Leu

<210> SEQ ID NO 3
<211> LENGTH: 1368
<212> TYPE: DNA
<213> ORGANISM: A. vitis strain F2/5
<220> FEATURE:
<221> NAME/KEY: misc_feature
<222> LOCATION: (1)..(1368)
<223> OTHER INFORMATION: avi4329

<400> SEQUENCE: 3

```
atgaatgaga acaagcgtca ggatctgctg gcccgtatgc gtggcgtaca aaaggatgtg      60
gaccggagcc gggccagccg cagccagcag agcgtgtcgc gcagccagcc aggttttgcc     120
gaattgcctg aatataagca ggtggtgatg cagaagcttg tcagcgagca actgaacatg     180
cccaatccgt tttaccgggc gcatgagagc gcctccgggg caacggctga tatcgacggg     240
cgcgcctatg ataattttgc ctcctatgat tatctcggct tgaacagtga tccacgcatt     300
cgcgatgccg ccatggcggc catcgaccag ttcggtatct cggcctccgc cagccggctt     360
gttgccggtg agcgcaccat ccatgccgag ctggaaaagg cctttgccaa aaattaccag     420
accgaggacg ccatctgttt cgtcagcggc tatctcacca atgtcacgac catcggcagc     480
ttgatggggc cgaaagacct ggtgatccat gacgagttca ttcacaacag cgccctgacg     540
ggcatcaagc tgtcgggtgc caatcgccgc ttcttcaagc ataatgacat ggcggacctg     600
gaccgtattc ttgcgagcct cgcccccttg catgaacgaa tcctggtgat ctccgagggc     660
attttctcca tggatggaga cgttgccgat ctgccgggcc ttcttgcatt gaaaaagcag     720
tataatttct ggctgatgat ggacgaggcc attctctggg gcgtacttgg acagcgtggc     780
cacggcattt tcgaacattt caatctcgat ccagccgatg tcgatatctg gatggggacg     840
ctgtcgaaaa ccacctgtag ctgcggcggc tatgttgccg gcagtgaagc gctgatcacg     900
ctgttgaagg cgcaggccgg tggtttcgtt tatagtgtcg gcttggcacc agcgctggcg     960
gctgcggcca tcgccagcct gtcggtgctg acgaggagc cggaccgggt agaggctttg    1020
cgtcgcaaca gccagctttt cctggagcaa gccaagctac gggggctgga taccggtctg    1080
agcgaaggtt tctcggtggt gcctgtgatc gttgccgatt cggtgcgcgc tgtgcagctt    1140
tccaatgaat tgttcgaggc aggcatcaat gcgctgccga tcatctatcc cgcagtaccg    1200
gaaggtctgg cacgtctgcg gttcttcatc accagcgccc acacgcccga ccagattacc    1260
cgcagcgtgg acaaggtggc ggacattctg atcggctga aggccgagaa tttcggcatg    1320
ggctcgatgg atgtccagaa ggtcatgctg caattggcgc agcgctga                1368
```

```
<210> SEQ ID NO 4
<211> LENGTH: 455
<212> TYPE: PRT
<213> ORGANISM: A. vitis strain F2/5
<220> FEATURE:
<221> NAME/KEY: MISC_FEATURE
<222> LOCATION: (1)..(455)
<223> OTHER INFORMATION: avi4329

<400> SEQUENCE: 4

Met Asn Glu Asn Lys Arg Gln Asp Leu Leu Ala Arg Met Arg Gly Val
1               5                   10                  15

Gln Lys Asp Val Asp Arg Ser Arg Ala Ser Arg Ser Gln Gln Ser Val
            20                  25                  30

Ser Arg Ser Gln Pro Gly Phe Ala Glu Leu Pro Glu Tyr Lys Gln Val
        35                  40                  45

Val Met Gln Lys Leu Val Ser Glu Gln Leu Asn Met Pro Asn Pro Phe
    50                  55                  60

Tyr Arg Ala His Glu Ser Ala Ser Gly Ala Thr Ala Asp Ile Asp Gly
65                  70                  75                  80

Arg Ala Tyr Asp Asn Phe Ala Ser Tyr Asp Tyr Leu Gly Leu Asn Ser
                85                  90                  95

Asp Pro Arg Ile Arg Asp Ala Ala Met Ala Ala Ile Asp Gln Phe Gly
            100                 105                 110

Ile Ser Ala Ser Ala Ser Arg Leu Val Ala Gly Glu Arg Thr Ile His
        115                 120                 125

Ala Glu Leu Glu Lys Ala Phe Ala Lys Asn Tyr Gln Thr Glu Asp Ala
    130                 135                 140

Ile Cys Phe Val Ser Gly Tyr Leu Thr Asn Val Thr Thr Ile Gly Ser
145                 150                 155                 160

Leu Met Gly Pro Lys Asp Leu Val Ile His Asp Glu Phe Ile His Asn
                165                 170                 175

Ser Ala Leu Thr Gly Ile Lys Leu Ser Gly Ala Asn Arg Arg Phe Phe
            180                 185                 190

Lys His Asn Asp Met Ala Asp Leu Asp Arg Ile Leu Ala Ser Leu Ala
        195                 200                 205

Pro Leu His Glu Arg Ile Leu Val Ile Ser Glu Gly Ile Phe Ser Met
    210                 215                 220

Asp Gly Asp Val Ala Asp Leu Pro Gly Leu Leu Ala Leu Lys Lys Gln
225                 230                 235                 240

Tyr Asn Phe Trp Leu Met Met Asp Glu Ala His Ser Leu Gly Val Leu
                245                 250                 255

Gly Gln Arg Gly His Gly Ile Phe Glu His Phe Asn Leu Asp Pro Ala
            260                 265                 270

Asp Val Asp Ile Trp Met Gly Thr Leu Ser Lys Thr Thr Cys Ser Cys
        275                 280                 285

Gly Gly Tyr Val Ala Gly Ser Glu Ala Leu Ile Thr Leu Leu Lys Ala
    290                 295                 300

Gln Ala Gly Gly Phe Val Tyr Ser Val Gly Leu Ala Pro Ala Leu Ala
305                 310                 315                 320

Ala Ala Ala Ile Ala Ser Leu Ser Val Leu Asp Glu Glu Pro Asp Arg
                325                 330                 335

Val Glu Ala Leu Arg Arg Asn Ser Gln Leu Phe Leu Glu Gln Ala Lys
            340                 345                 350

Leu Arg Gly Leu Asp Thr Gly Leu Ser Glu Gly Phe Ser Val Val Pro
        355                 360                 365
```

Val Ile Val Ala Asp Ser Val Arg Ala Val Gln Leu Ser Asn Glu Leu
        370                 375                 380

Phe Glu Ala Gly Ile Asn Ala Leu Pro Ile Ile Tyr Pro Ala Val Pro
385                 390                 395                 400

Glu Gly Leu Ala Arg Leu Arg Phe Phe Ile Thr Ser Ala His Thr Pro
                405                 410                 415

Asp Gln Ile Thr Arg Ser Val Asp Lys Val Ala Asp Ile Leu Asp Arg
                420                 425                 430

Leu Lys Ala Glu Asn Phe Gly Met Gly Ser Met Asp Val Gln Lys Val
        435                 440                 445

Met Leu Gln Leu Ala Gln Arg
        450                 455

<210> SEQ ID NO 5
<211> LENGTH: 471
<212> TYPE: DNA
<213> ORGANISM: A. vitis strain F2/5
<220> FEATURE:
<221> NAME/KEY: misc_feature
<222> LOCATION: (1)..(471)
<223> OTHER INFORMATION: avi0838

<400> SEQUENCE: 5

```
atgcgcttga cgaagcagac caattacgcg gtacgcattc tgatgtattg cgcggcgaac    60
aaggaccacc tgagccgtat cccggaaatt gccaaggcct atggcgtctc cgaactgttc   120
ctgttcaaaa tccttcagcc gctcaacaag gcgggtctgg tggaaaccgt gcgtggccgc   180
aatggcggcg tgcgcctagg tcgtgcgcct gaaaagatca gcctgtttga cgtggtcaag   240
gtcacggaag acagctttgc gatggccgaa tgcttcgagg acgatggcga ggtcgattgc   300
ccgttgatcg acagctgcgg cctgaattcg gcgctgcgca aggcgctcaa cgctttcttc   360
gcggtgctgg cggaatattc catcgatgat ctggtcaagg cccgcccgca gatcaacttt   420
ttgctgggta tcgaggatct gcctcgtctg gcggcggcac cggctgcctg a            471
```

<210> SEQ ID NO 6
<211> LENGTH: 156
<212> TYPE: PRT
<213> ORGANISM: A. vitis strain F2/5
<220> FEATURE:
<221> NAME/KEY: MISC_FEATURE
<222> LOCATION: (1)..(156)
<223> OTHER INFORMATION: avi0838

<400> SEQUENCE: 6

Met Arg Leu Thr Lys Gln Thr Asn Tyr Ala Val Arg Ile Leu Met Tyr
1               5                   10                  15

Cys Ala Ala Asn Lys Asp His Leu Ser Arg Ile Pro Glu Ile Ala Lys
                20                  25                  30

Ala Tyr Gly Val Ser Glu Leu Phe Leu Phe Lys Ile Leu Gln Pro Leu
        35                  40                  45

Asn Lys Ala Gly Leu Val Glu Thr Val Arg Gly Arg Asn Gly Gly Val
    50                  55                  60

Arg Leu Gly Arg Ala Pro Glu Lys Ile Ser Leu Phe Asp Val Val Lys
65                  70                  75                  80

Val Thr Glu Asp Ser Phe Ala Met Ala Glu Cys Phe Glu Asp Asp Gly
                85                  90                  95

Glu Val Asp Cys Pro Leu Ile Asp Ser Cys Gly Leu Asn Ser Ala Leu
            100                 105                 110

Arg Lys Ala Leu Asn Ala Phe Phe Ala Val Leu Ala Glu Tyr Ser Ile
            115                 120                 125

Asp Asp Leu Val Lys Ala Arg Pro Gln Ile Asn Phe Leu Leu Gly Ile
    130                 135                 140

Glu Asp Leu Pro Arg Leu Ala Ala Ala Pro Ala Ala
145                 150                 155

<210> SEQ ID NO 7
<211> LENGTH: 741
<212> TYPE: DNA
<213> ORGANISM: A. vitis strain F2/5
<220> FEATURE:
<221> NAME/KEY: misc_feature
<222> LOCATION: (1)..(741)
<223> OTHER INFORMATION: avi4374

<400> SEQUENCE: 7
gtgagtgtca atcatctcat acagtttttg gctgtatctc agggatgccg aagtcgcgag      60
gagctgatcc tagaattgga gaaactcctc gaatttata aattcgatta ttacggcctc     120
gtgcgcagtc ccaaacctga ccaaaacccc atgtcgctgg tgcttgcagg acgctggccg     180
gaaaatggc cgcaggtcta tatcacgaaa aaattcgtgc tgatcgaccc tgccattcgc      240
tatctggcgc aagcgcaacg gccgttccgt tggagcgaaa cgctgacggc attcagccag     300
gacccacatt tcaaacgcat gcagcggatg atgatggatg cccagcgctt tggtctcgag     360
gaaggctata tcttcccat ccacgggcgg ggcggattgc tggccaacat gaccattggc      420
gggagaccgg tggaactgac cccgattgag atcatgctgt cgacacggt ggcgaaatgc      480
gccttctggc ggctggcgga atcaatggc gaagacgaac tgctgtcgat ggtgcaaaaa      540
gtcgatgtgc gcctgacccg acgcgagctt gaaattctca attatctcgg ggagggcatg     600
acctcgaacg agatgagcaa attgctcgag atttcgaacc acaccgtcga ttggtacgtc     660
aacgaattgc aggataagtt gaacgccaag aatcggcaac atatggtagc aattgcttat     720
cgactcggcc tgatcagctg a                                              741

<210> SEQ ID NO 8
<211> LENGTH: 246
<212> TYPE: PRT
<213> ORGANISM: A. vitis strain F2/5
<220> FEATURE:
<221> NAME/KEY: MISC_FEATURE
<222> LOCATION: (1)..(246)
<223> OTHER INFORMATION: avi4374

<400> SEQUENCE: 8

Met Ser Val Asn His Leu Ile Gln Phe Leu Ala Val Ser Gln Gly Cys
1               5                   10                  15

Arg Ser Arg Glu Glu Leu Ile Leu Glu Leu Glu Lys Leu Leu Glu Phe
            20                  25                  30

Tyr Lys Phe Asp Tyr Tyr Gly Leu Val Arg Ser Pro Lys Pro Asp Gln
        35                  40                  45

Asn Pro Met Ser Leu Val Leu Ala Gly Arg Trp Pro Glu Lys Trp Pro
    50                  55                  60

Gln Val Tyr Ile Thr Lys Lys Phe Val Leu Ile Asp Pro Ala Ile Arg
65                  70                  75                  80

Tyr Leu Ala Gln Ala Gln Arg Pro Phe Arg Trp Ser Glu Thr Leu Thr
                85                  90                  95

Ala Phe Ser Gln Asp Pro His Phe Lys Arg Met Gln Arg Met Met Met

Asp Ala Gln Arg Phe Gly Leu Glu Glu Gly Tyr Ile Phe Pro Ile His
            115                 120                 125

Gly Arg Gly Gly Leu Leu Ala Asn Met Thr Ile Gly Gly Arg Pro Val
130                 135                 140

Glu Leu Thr Pro Ile Glu Ile Met Leu Phe Asp Thr Val Ala Lys Cys
145                 150                 155                 160

Ala Phe Trp Arg Leu Ala Glu Ile Asn Gly Glu Asp Glu Leu Leu Ser
                165                 170                 175

Met Val Gln Lys Val Asp Val Arg Leu Thr Arg Arg Glu Leu Glu Ile
            180                 185                 190

Leu Asn Tyr Leu Gly Glu Gly Met Thr Ser Asn Glu Met Ser Lys Leu
        195                 200                 205

Leu Glu Ile Ser Asn His Thr Val Asp Trp Tyr Val Asn Glu Leu Gln
    210                 215                 220

Asp Lys Leu Asn Ala Lys Asn Arg Gln His Met Val Ala Ile Ala Tyr
225                 230                 235                 240

Arg Leu Gly Leu Ile Ser
            245

<210> SEQ ID NO 9
<211> LENGTH: 633
<212> TYPE: DNA
<213> ORGANISM: A. vitis strain F2/5
<220> FEATURE:
<221> NAME/KEY: misc_feature
<222> LOCATION: (1)..(633)
<223> OTHER INFORMATION: avi1696

<400> SEQUENCE: 9
atgagaaatc cagttgatac cgccatggct ctggtgccta tggttgtgga gcagaccaat      60
cgcggcgaac ggtcctacga catctactcg cgtctgttga aggagcgcat cattttcctg     120
accggaccgg ttgaggatca tatggcgtcg cttgtctgcg cccagctgct gtttctggaa     180
gcggaaaatc cgaagaagga aatcgcgatc tacatcaatt ctcccggcgg cgtcgtgact     240
gccggcatgg cgatctacga tacgatgcag ttcatccgtc cggccgtctc gacgctgtgc     300
gtcggccagg ccgcctcgat ggggtcgctg ctgctggcgg ccggcgaaaa gggcatgcgc     360
tttgcgaccc ccaacgcccg catcatggtg catcagccgt ccggcggttt ccaggggcag     420
gcctccgaca tcgagcggca tgcccgcgac atcatcaaga tgaagcgtcg cttgaacgag     480
gtttatgtca agcacactgg acgcacgctg aagaagtcg agcacacgct tgaccgcgac     540
cacttcatgg aatccacgga agctaaggat tggggtctga tcgacaagat cctgacgacg     600
cgctccgaaa ttgaaggggt aacgccttct tga                                  633

<210> SEQ ID NO 10
<211> LENGTH: 210
<212> TYPE: PRT
<213> ORGANISM: A. vitis strain F2/5
<220> FEATURE:
<221> NAME/KEY: MISC_FEATURE
<222> LOCATION: (1)..(210)
<223> OTHER INFORMATION: avi1696

<400> SEQUENCE: 10

Met Arg Asn Pro Val Asp Thr Ala Met Ala Leu Val Pro Met Val Val
1               5                   10                  15

Glu Gln Thr Asn Arg Gly Glu Arg Ser Tyr Asp Ile Tyr Ser Arg Leu

```
                20                  25                  30
Leu Lys Glu Arg Ile Ile Phe Leu Thr Gly Pro Val Glu Asp His Met
             35                  40                  45

Ala Ser Leu Val Cys Ala Gln Leu Leu Phe Leu Glu Ala Glu Asn Pro
 50                  55                  60

Lys Lys Glu Ile Ala Ile Tyr Ile Asn Ser Pro Gly Gly Val Val Thr
 65                  70                  75                  80

Ala Gly Met Ala Ile Tyr Asp Thr Met Gln Phe Ile Arg Pro Ala Val
                 85                  90                  95

Ser Thr Leu Cys Val Gly Gln Ala Ala Ser Met Gly Ser Leu Leu Leu
            100                 105                 110

Ala Ala Gly Glu Lys Gly Met Arg Phe Ala Thr Pro Asn Ala Arg Ile
            115                 120                 125

Met Val His Gln Pro Ser Gly Gly Phe Gln Gly Gln Ala Ser Asp Ile
        130                 135                 140

Glu Arg His Ala Arg Asp Ile Ile Lys Met Lys Arg Arg Leu Asn Glu
145                 150                 155                 160

Val Tyr Val Lys His Thr Gly Arg Thr Leu Glu Glu Val Glu His Thr
                165                 170                 175

Leu Asp Arg Asp His Phe Met Glu Ser Thr Glu Ala Lys Asp Trp Gly
            180                 185                 190

Leu Ile Asp Lys Ile Leu Thr Thr Arg Ser Glu Ile Glu Gly Val Thr
            195                 200                 205

Pro Ser
    210

<210> SEQ ID NO 11
<211> LENGTH: 4005
<212> TYPE: DNA
<213> ORGANISM: A. vitis strain F2/5
<220> FEATURE:
<221> NAME/KEY: misc_feature
<222> LOCATION: (1)..(4005)
<223> OTHER INFORMATION: avi3342

<400> SEQUENCE: 11
atgtcttttg taggcagaca tgagcaggtt tttccggttt ctcttgcgca ggcaggcttg      60
tgggtcaaac aaaaggtagc tcccgccgat ctgagctttg tccttgctga atccatcgaa     120
attcacggtc ccgttcatcc aggactgttc tgccaggcgt tgcgccgctt gtcagatgat     180
gttgctgtca cacggtctcg catcaaggaa atcgaagggc agccacatca ggttgtcatg     240
gcggcctatt gcggcgtctt tgacgtgatc gatttcagcg gtgctgacaa tcctggcgca     300
agcgccatgg actggatgcg caagcagatg tctaagccgc tcgatcttgc caatgacaat     360 ctctggggggt cttcactttt gaagctcggg gccacagaat gggtctggta tcattgggca     420
catcatatca tcatggatgg gttctctggc ggcttgctgg cccggcggct ggccgatatt     480
tattcggcgc tggcccaggg caaccagccg agcccatatg attgcggttc ccgcaggaa      540 ttgctggagc ttgagcgcac ctaccgcgat cggtgcatt tccagcgcga caaggcctat     600
tggtcggagc agatgaaggg tctgccggag ccggtgacct tgatgaagaa aaaaggcgag     660
ccatccggtg gcctgttgcg ccatacgacg gtcatcgatc gccagacggt caaggcgctt     720
gctgagatca gccgtggctt tggcgccagc gtgccacagg ccttgattgc ccttgtcgcg     780
gcctattacg ccaaggcgac cgactgcgaa gagctgacca tggtcaccat ggtgacggcc     840
cggatcagcc agacgatgcg ccgcattccg ggcatgaccg ccaatgcggt tcctctgcgg     900
```

| | |
|---|---|
| ttttcgatca cgccggacct gtcctggcgc gaattgaccg gtcaggtttc ccagcagatg | 960 |
| agccgggcgc tgcgctatca gcgctatcgc tatgaggata ttcgccgcga tctcggcatg | 1020 |
| gtccgccagg atgcgcagat tgcctggctg ggcgtcaata tcgagccttt cgactacgat | 1080 |
| ctacgctttg atggacagcc aaccaccgtg cacaaccttt cgaatggcac gatgacggat | 1140 |
| ttcaccatct tcgcctatga ccgtggtgac aatggcgacc tgcgcatcga ttttgatgcc | 1200 |
| aatccggcgc tctatacgct ggaagagctg gccgatcacg aggcgcggtt cacccgcatg | 1260 |
| ttgagagaga tcctcgcgac gcctgaacag cccctgcgcg atttcagcct gctgtcgaag | 1320 |
| tgggagcggc aggaaattct caccgactgg aacgatacgt cccataagct gccggatcag | 1380 |
| acctggccgg aattgttccg ggcgcaggcg gcacgcacgc cggatgcggt agcgctatcc | 1440 |
| tttggcggtc gccagatgac ctatggtgag ctggatgccg cctccgatca tctggctggc | 1500 |
| tatctgatgg aaaagggcgc cgtacccggt tctctggtgg ctgtggctgt gccgcggtct | 1560 |
| gaaaacatgt tgtgcgct gctggcagtg ctcaaaagcg gtgccgccta tctaccgctc | 1620 |
| gatccggctg atccagcctc gcgggtggcg atgatcctgg aggatgcgca gccagcctgc | 1680 |
| gttatcacca ctgaggaagt ggcgggcaac ctgccggatg ccaccgacaa cctgatcttc | 1740 |
| ctcgacaagc ccctcgagcg acagggacgc gacctgccga aggggccatc gctgagcgac | 1800 |
| acggcctata tcatcttcac gtccggttcg accggtcggc ccaagggcgt ggaaattcca | 1860 |
| catcgcggcc tgatgaactt cctgttgtcg atgcaggatc tgttgaaact ggacagcgaa | 1920 |
| gaccggttgc tggctgtgac gacgatttcc ttcgatattg cagcacttga gctttatctg | 1980 |
| cccttgctgg caggcgcgcg cacggtgatc gcgctgcgct cggaagtgcg cgaccccggcg | 2040 |
| gtgctgcatg ggttgatccg cagtgcgggt atcaccatca tgcaggcgac gccgtctttg | 2100 |
| tggcgggcct tgctggccga tcatcatgag ggactgacgg gcttgcgcag tcttgtcggt | 2160 |
| ggtgaggcgc ttcccgccga tctcgcccat aagatggcgc ggctcggcca cccggttctc | 2220 |
| aatgtctacg gaccgacgga aaccacgatc tggtccacca acatgccgct ttgggcagc | 2280 |
| gacctcgaca gtgcgccaat tggccggcca atctggaaca cccgcgttta tgtcctcgat | 2340 |
| cggcattgcc agccagtgcc gcccggcttt atcggtgagc tgtatatcgg tggtgcgggc | 2400 |
| gtggcgaagg gctacctgaa ccgcccggac ctgacggcgg aaaaattcat ggctgatcct | 2460 |
| ttcgcaggcg aaggcgagcg gatctaccgg accggcgacc tggtgcgctg gcggcgcgat | 2520 |
| ggcgtgctgg attatctcgg ccgcaacgac caccagatca agattcgtgg attccgggtg | 2580 |
| gagccgggcg aaatcgaggc ggcgctttcc gccctgccgc aggtgcgtga agcggtggtt | 2640 |
| attctgcgcg atgatccggg ccgcgaaaag cgactggttg cctatgttgt cccagagag | 2700 |
| ggtgcggtag gcgagggtgc ctcgctggat gctgctgatc tttcggagcg gctaggcaag | 2760 |
| gttctgcccg ttcacatgat cccggcggcc tatgtggtgc tggacgctat tccgttgaat | 2820 |
| tccaatggca agaccgaccg gcacgcgctg ccggtaccgc aatggacggt gacggaaggc | 2880 |
| atagccctgc cggggaccga tgctgaaaag cggcttgccg ccttgtggtg cgagatcctt | 2940 |
| ggtctggagc agatcggcat tcacgacagt ttcttcgtgc tgggtggtga ctcgctggct | 3000 |
| gccgctggaa tgatttccgc cgttcgcagc cgattgaagg gcgaaattcc cctcggtgcc | 3060 |
| gtgttcgaaa caccaaccat tgccgccttg gccgtgcatc tggatgaggc aagctcgggt | 3120 |
| tcaccactga ttgaaccggt tctggccatc cgcgccaagg gcgagcgccc gccgctgttc | 3180 |
| tgcatccatc cggtgctggg cttgggctgg agcttcttct cgctcgcaca acatttgagc | 3240 |

```
gaggatgtcc cggtttacgc cctgcaatcg gacgggttgc atgacctcgc cgccctgccg    3300
cgctctatcg aggatatggc tgcgctctat gtgcagcgga ttcgcaagat ccagccgcag    3360
gggccatatc atctgctggg ctggtcattg ggcgggctga ttgcccatga aatgacccgg    3420
caattgcagg cagaaggcca ggctatcgcg ttcctgggca tgatggacag ctaccatttc    3480
aaacctgctg cccaattgca ggacgatgcg acgctggcgc gggccgccct cggtttcctc    3540
ggctttgatg aaaaggcagc gggcgacaag ccatcgctgg ccgagcttgg cgatttcgtg    3600
ctgaaaatgt tcgatacgga caaccatgtc ctgctggaac aggttcacca gttcgatccc    3660
gagttcgtcg agcgcgccaa ggcaaccatc cttcacaatc tggagattgc ccagcgcttt    3720
acaccgggca agatcgatgc cgatgtgcat ttcttccgcg ccgaaccaag tgcgggcagc    3780
gatgcgctga acaccatcct caactacgat gcggaaacct ggttgccgca tgtggagggc    3840
agggtttacc tgcgcgacat gacctgcaac caccacgaca tgctgaatat cgaaccggca    3900
tcccatatca gcgccgtcgt tcaagcagag ttgctgcgtg aattcctggt cctgcgtcgg    3960
ccccagactg aggtcaagat tgagcgtgtg tcgcggtttg cctaa                   4005
```

<210> SEQ ID NO 12
<211> LENGTH: 1334
<212> TYPE: PRT
<213> ORGANISM: A. vitis strain F2/5
<220> FEATURE:
<221> NAME/KEY: MISC_FEATURE
<222> LOCATION: (1)..(1334)
<223> OTHER INFORMATION: avi3342

<400> SEQUENCE: 12

```
Met Ser Phe Val Gly Arg His Glu Gln Val Phe Pro Val Ser Leu Ala
1               5                   10                  15

Gln Ala Gly Leu Trp Val Lys Gln Lys Val Ala Pro Ala Asp Leu Ser
            20                  25                  30

Phe Val Leu Ala Glu Ser Ile Glu Ile His Gly Pro Val His Pro Gly
        35                  40                  45

Leu Phe Cys Gln Ala Leu Arg Arg Leu Ser Asp Asp Val Ala Val Thr
    50                  55                  60

Arg Ser Arg Ile Lys Glu Ile Glu Gly Gln Pro His Gln Val Val Met
65                  70                  75                  80

Ala Ala Tyr Cys Gly Val Phe Asp Val Ile Asp Phe Ser Gly Ala Asp
                85                  90                  95

Asn Pro Gly Ala Ser Ala Met Asp Trp Met Arg Lys Gln Met Ser Lys
            100                 105                 110

Pro Leu Asp Leu Ala Asn Asp Asn Leu Trp Gly Ser Ser Leu Leu Lys
        115                 120                 125

Leu Gly Ala Thr Glu Trp Val Trp Tyr His Trp Ala His His Ile Ile
    130                 135                 140

Met Asp Gly Phe Ser Gly Gly Leu Leu Ala Arg Arg Leu Ala Asp Ile
145                 150                 155                 160

Tyr Ser Ala Leu Ala Gln Gly Asn Gln Pro Glu Pro Tyr Asp Cys Gly
                165                 170                 175

Ser Pro Gln Glu Leu Leu Glu Leu Glu Arg Thr Tyr Arg Asp Ser Val
            180                 185                 190

His Phe Gln Arg Asp Lys Ala Tyr Trp Ser Glu Gln Met Lys Gly Leu
        195                 200                 205

Pro Glu Pro Val Thr Leu Met Lys Lys Lys Gly Glu Pro Ser Gly Gly
    210                 215                 220
```

```
Leu Leu Arg His Thr Thr Val Ile Asp Arg Gln Thr Val Lys Ala Leu
225                 230                 235                 240

Ala Glu Ile Ser Arg Gly Phe Gly Ala Ser Val Pro Gln Ala Leu Ile
            245                 250                 255

Ala Leu Val Ala Ala Tyr Tyr Ala Lys Ala Thr Asp Cys Glu Glu Leu
                260                 265                 270

Thr Met Val Thr Met Val Thr Ala Arg Ile Ser Gln Thr Met Arg Arg
            275                 280                 285

Ile Pro Gly Met Thr Ala Asn Ala Val Pro Leu Arg Phe Ser Ile Thr
            290                 295                 300

Pro Asp Leu Ser Trp Arg Glu Leu Thr Gly Val Ser Gln Gln Met
305                 310                 315                 320

Ser Arg Ala Leu Arg Tyr Gln Arg Tyr Arg Tyr Glu Asp Ile Arg Arg
                325                 330                 335

Asp Leu Gly Met Val Arg Gln Asp Ala Gln Ile Ala Trp Leu Gly Val
                340                 345                 350

Asn Ile Glu Pro Phe Asp Tyr Asp Leu Arg Phe Asp Gly Gln Pro Thr
            355                 360                 365

Thr Val His Asn Leu Ser Asn Gly Thr Met Thr Asp Phe Thr Ile Phe
370                 375                 380

Ala Tyr Asp Arg Gly Asp Asn Gly Asp Leu Arg Ile Asp Phe Asp Ala
385                 390                 395                 400

Asn Pro Ala Leu Tyr Thr Leu Glu Glu Leu Ala Asp His Glu Ala Arg
                405                 410                 415

Phe Thr Arg Met Leu Arg Glu Ile Leu Ala Thr Pro Glu Gln Pro Leu
                420                 425                 430

Arg Asp Phe Ser Leu Leu Ser Lys Trp Glu Arg Gln Glu Ile Leu Thr
                435                 440                 445

Asp Trp Asn Asp Thr Ser His Lys Leu Pro Asp Gln Thr Trp Pro Glu
450                 455                 460

Leu Phe Arg Ala Gln Ala Arg Thr Pro Asp Ala Val Ala Leu Ser
465                 470                 475                 480

Phe Gly Gly Arg Gln Met Thr Tyr Gly Glu Leu Asp Ala Ala Ser Asp
                485                 490                 495

His Leu Ala Gly Tyr Leu Met Glu Lys Gly Ala Val Pro Gly Ser Leu
                500                 505                 510

Val Ala Val Ala Val Pro Arg Ser Glu Asn Met Val Val Ala Leu Leu
                515                 520                 525

Ala Val Leu Lys Ser Gly Ala Ala Tyr Leu Pro Leu Asp Pro Ala Asp
                530                 535                 540

Pro Ala Ser Arg Val Ala Met Ile Leu Glu Asp Ala Gln Pro Ala Cys
545                 550                 555                 560

Val Ile Thr Thr Glu Glu Val Ala Gly Asn Leu Pro Asp Ala Thr Asp
                565                 570                 575

Asn Leu Ile Phe Leu Asp Lys Pro Leu Glu Arg Gln Gly Arg Asp Leu
                580                 585                 590

Pro Lys Gly Pro Ser Leu Ser Asp Thr Ala Tyr Ile Ile Phe Thr Ser
            595                 600                 605

Gly Ser Thr Gly Arg Pro Lys Gly Val Glu Ile Pro His Arg Gly Leu
            610                 615                 620

Met Asn Phe Leu Leu Ser Met Gln Asp Leu Leu Lys Leu Asp Ser Glu
625                 630                 635                 640
```

```
Asp Arg Leu Leu Ala Val Thr Thr Ile Ser Phe Asp Ile Ala Ala Leu
            645                 650                 655

Glu Leu Tyr Leu Pro Leu Leu Ala Gly Ala Arg Thr Val Ile Ala Leu
            660                 665                 670

Arg Ser Glu Val Arg Asp Pro Ala Val Leu His Gly Leu Ile Arg Ser
        675                 680                 685

Ala Gly Ile Thr Ile Met Gln Ala Thr Pro Ser Leu Trp Arg Ala Leu
    690                 695                 700

Leu Ala Asp His His Glu Gly Leu Thr Gly Leu Arg Ser Leu Val Gly
705                 710                 715                 720

Gly Glu Ala Leu Pro Ala Asp Leu Ala His Lys Met Ala Arg Leu Gly
                725                 730                 735

His Pro Val Leu Asn Val Tyr Gly Pro Thr Glu Thr Thr Ile Trp Ser
            740                 745                 750

Thr Asn Met Pro Leu Leu Gly Ser Asp Leu Asp Ser Ala Pro Ile Gly
        755                 760                 765

Arg Pro Ile Trp Asn Thr Arg Val Tyr Val Leu Asp Arg His Cys Gln
    770                 775                 780

Pro Val Pro Pro Gly Phe Ile Gly Glu Leu Tyr Ile Gly Gly Ala Gly
785                 790                 795                 800

Val Ala Lys Gly Tyr Leu Asn Arg Pro Asp Leu Thr Ala Glu Lys Phe
                805                 810                 815

Met Ala Asp Pro Phe Ala Gly Glu Gly Glu Arg Ile Tyr Arg Thr Gly
            820                 825                 830

Asp Leu Val Arg Trp Arg Arg Asp Gly Val Leu Asp Tyr Leu Gly Arg
        835                 840                 845

Asn Asp His Gln Ile Lys Ile Arg Gly Phe Arg Val Glu Pro Gly Glu
    850                 855                 860

Ile Glu Ala Ala Leu Ser Ala Leu Pro Gln Val Arg Glu Ala Val Val
865                 870                 875                 880

Ile Leu Arg Asp Asp Pro Gly Arg Glu Lys Arg Leu Val Ala Tyr Val
                885                 890                 895

Val Pro Arg Glu Gly Ala Val Gly Glu Gly Ala Ser Leu Asp Ala Ala
            900                 905                 910

Asp Leu Ser Glu Arg Leu Gly Lys Val Leu Pro Val His Met Ile Pro
        915                 920                 925

Ala Ala Tyr Val Val Leu Asp Ala Ile Pro Leu Asn Ser Asn Gly Lys
    930                 935                 940

Thr Asp Arg His Ala Leu Pro Val Pro Gln Trp Thr Val Thr Glu Gly
945                 950                 955                 960

Ile Ala Leu Pro Gly Thr Asp Ala Glu Lys Arg Leu Ala Ala Leu Trp
                965                 970                 975

Cys Glu Ile Leu Gly Leu Glu Gln Ile Gly Ile His Asp Ser Phe Phe
            980                 985                 990

Val Leu Gly Gly Asp Ser Leu Ala  Ala Gly Met Ile  Ser Ala Val
            995                 1000                 1005

Arg Ser  Arg Leu Lys Gly Glu  Ile Pro Leu Gly Ala  Val Phe Glu
        1010                 1015                 1020

Thr Pro  Thr Ile Ala Ala Leu  Ala Val His Leu Asp  Glu Ala Ser
        1025                 1030                 1035

Ser Gly  Ser Pro Leu Ile Glu  Pro Val Leu Ala Ile  Arg Ala Lys
        1040                 1045                 1050

Gly Glu  Arg Pro Pro Leu Phe  Cys Ile His Pro Val  Leu Gly Leu
```

Gly Trp Ser Phe Phe Ser Leu Ala Gln His Leu Ser Glu Asp Val
    1070            1075                1080

Pro Val Tyr Ala Leu Gln Ser Asp Gly Leu His Asp Leu Ala Ala
    1085            1090                1095

Leu Pro Arg Ser Ile Glu Asp Met Ala Ala Leu Tyr Val Gln Arg
    1100            1105                1110

Ile Arg Lys Ile Gln Pro Gln Gly Pro Tyr His Leu Leu Gly Trp
    1115            1120                1125

Ser Leu Gly Gly Leu Ile Ala His Glu Met Thr Arg Gln Leu Gln
    1130            1135                1140

Ala Glu Gly Gln Ala Ile Ala Phe Leu Gly Met Met Asp Ser Tyr
    1145            1150                1155

His Phe Lys Pro Ala Ala Gln Leu Gln Asp Asp Ala Thr Leu Ala
    1160            1165                1170

Arg Ala Ala Leu Gly Phe Leu Gly Phe Asp Glu Lys Ala Ala Gly
    1175            1180                1185

Asp Lys Pro Ser Leu Ala Glu Leu Gly Asp Phe Val Leu Lys Met
    1190            1195                1200

Phe Asp Thr Asp Asn His Val Leu Leu Glu Gln Val His Gln Phe
    1205            1210                1215

Asp Pro Glu Phe Val Glu Arg Ala Lys Ala Thr Ile Leu His Asn
    1220            1225                1230

Leu Glu Ile Ala Gln Arg Phe Thr Pro Gly Lys Ile Asp Ala Asp
    1235            1240                1245

Val His Phe Phe Arg Ala Glu Pro Ser Ala Gly Ser Asp Ala Leu
    1250            1255                1260

Asn Thr Ile Leu Asn Tyr Asp Ala Glu Thr Trp Leu Pro His Val
    1265            1270                1275

Glu Gly Arg Val Tyr Leu Arg Asp Met Thr Cys Asn His His Asp
    1280            1285                1290

Met Leu Asn Ile Glu Pro Ala Ser His Ile Ser Ala Val Val Gln
    1295            1300                1305

Ala Glu Leu Leu Arg Glu Phe Leu Val Leu Arg Arg Pro Gln Thr
    1310            1315                1320

Glu Val Lys Ile Glu Arg Val Ser Arg Phe Ala
    1325            1330

<210> SEQ ID NO 13
<211> LENGTH: 7524
<212> TYPE: DNA
<213> ORGANISM: A. vitis strain F2/5
<220> FEATURE:
<221> NAME/KEY: misc_feature
<222> LOCATION: (1)..(7524)
<223> OTHER INFORMATION: avi4330

<400> SEQUENCE: 13
ttgtttgatc ttttgcgtgc cggcgcatgc actgtctcga ccttgcccgg ggatcgttgg      60
gatattgcgc gctactggca tcccgaaatc ggcacgcctg caaatatta caccttcgct     120 gccggtgtga tggatggaat ctatcagttc gatcccgccc tgttcggcat gtcacggcgt     180
gaagccgcct ttatggaccc gcagcagcgc atcctgctgg agttgacctg gcgggcgctg     240
gaagatgcca atatccccgc caatagtctg tccggccaga atgtcgcggt ctatgtcggt     300
gcctccagtt tcgaccatgc caatctggcg gcggaagatc cggctggtcc cggtccgcat     360

```
ttcatgaccg gcaatacgct atcggtggtc tccaaccgta tctctcatgt cttcggcctg      420
aatggtccga gcatgacggt cgatacggcc tgctcgtcct cgctggtcgc actcgatcac      480
gcggtgcgcg cgattgcgtc tggcgaggtt gacaccgcca ttgttgccgg tgtcaacgtt      540
ctggtccatc cgctgccttt cgttggcttt gcgcaggcgc gcatgctgtc gatcgacggt      600
ttgtgcaagg cctatgccaa tgacggtatc gggtatgttc gggccgaagg cggtgccgtg      660
ctggtgctgc gatctagcga taaggcccgg cgcgaaggcg accgcagcca cgcgactatt      720
gttgccagcg gcaccaatgc agccgggcgc accaacggta tttcgctgcc gtcgcgcgag      780
gcgcaggccg ttctgttgcg cgccgtctat gacgacaatg gtctcgaccc ggatcggctg      840
gcctttatcg aaggccatgg caccggcacc aaggtcggcg atcccgccga agtctggtcg      900
cttggcacgg tcatcggcca gcgtcgcaag gaacctgtgt ggatcggctc gatcaaaacc      960
aatatcggtc ataccgaacc cgcatccggc ctgcttggcg tgatgaaggc gatgatggct     1020 tgcagcacg acctgcttcc ggcctcgctg catttcaatg agccgaatga cacgattgat      1080
ttcgatggcc tgaatgtccg ggttgcctcg caggccgttg cactggcacg cgatggtgcg     1140
ccgcgccttg ccggaatcaa ctcctttggc tttggcggcg ccaatgcaca tgtggtgatt     1200
gccgatccgc agagacctga tttggtgcct ggtttggcgc aagacgcggc taatccagcc     1260
ggtgccggtc gcttgttcat ggccagcgcc cactctcagg aaagcctgaa agcgttgctg     1320
gacagttacg acaaggcctt tgcggccgct ggaagcgatg gtgatctgga agacctgatc     1380
tcggcggccg cctccaaccg tgcgccgctc cggcaccgtt tcgttgccag tggcagcgcg     1440
gatgccatcg tcaaggcagt gcaggaacgg cttgccacag cgaagaccgg cggcgaaacc     1500
ggcgaagcct tgtcgcgcaa cggcaagctc gccttcgtgt tttctggcaa tggcgcccaa     1560
tgggcgggca tgggtcttga tgcctaccgg gcaaacgccc gcttccgcga gagctatgag     1620
cggatcgcca cgctctttac ggcgcattcg gaccttgacc tcgttgccgg cttgaccgat     1680
ccggatctgg aagcccgatt gaaagatacc aggcttgccc agcctatgct gtttgccatc     1740
caggcctcgc tgtcggatgc gctgcaactt gccggtctgg tgccggatgc tgtttacggt     1800
cattcggtcg gtgaagtggc tgccgcctat gtatcgggtg cgctgtcgct gaaggatgcc     1860
gtctgtgtca tcgccaaacg gtcgcagcat caggcggtgt tggccggtga aggcacgatg     1920
gcggccctga gcttggcgga ggccgatgcg cgcgccatgc tggccgagct ggctttgat     1980 gacctgacga ttgccgcgat caatgcgccc aattcggtga ccgtgtctgg tcgtgaagac     2040
gcgatccggg cgctgaggga acatgcccgc aagcagcggg tgccagccca ggtgctggac     2100
attgactatc ccttccatca tccgctgatc gataaggcga aggctgcctt ttccgccgat     2160
ccgccgctga ttacccgcg ccagaccacc cttccattca tctccaccggt gacgggtgag     2220 caactggagg gcaccgcact gacttcggat tactggtgga agaatgtccg ccagccggtg     2280
cagttccaag gggcgacgga agcggccatc gcgcttggtt gcaccgtgtt cgttgaaatt     2340
tctccgcgtg cgatccttgg cggctatgtg tcggaaacgg cgcagcatgt gtcttcgacg     2400
gttgccgtca gtgccagcct tagccgtgag gctccggatg agacggtcga tccggtggcg     2460 cgggcttttgg cgcgtgctgt cgccagcggc gccaaggtgg atgaggccaa ggtcttcggt     2520
ccgcgccgcg ccgatatcgt cctgccgggc gtgcctttcg agcgggccga tctgcgaccg     2580
gagccgacca gtgaccgcgt cgatctctat ggccggttcg gccagacggc ctatcggttg     2640
agcggctggc gggtcgattt gaatggcggg cattggaaaa accatctcga cgcgcacctg     2700
```

```
tttccggatc tggccgaaca tgtggtcgat ggccgggcca ttttgccggg cagcggtttt    2760
gtggaaattg ccatttcggc ggcgcaggcg catttcggct ccgaccagct tgagatcagc    2820
aatgtcgaga tcatgcgacc gctggaattg agcgacagcc ggatcgtcga actttccacg    2880
ctgatttccg ccgcgaccgg cgatcttcag atccgctcgc gcgagcggct gagcgatgac    2940
gactggacgg tgaatgcggt tgcccgggtt cgcaagctca cggcctccga actggacgat    3000
gccgtggatt tcgacctgtc cagcccgaca tcagagctgg ataaatctgc cgcctatcgg    3060
acggcgcgca atttcggcct ggattatggg ccgcgcttcc aattgctgga aaaggcgatc    3120
tgccatggcg agcggcttgt cgaagtgttc ctgaagccgg cagccgcgcc gggtcacccg    3180
ttgctgcgct ataatctcaa cccgatgtcg gttgatgcga tgttccacgg gttggtggcg    3240
ctgtttggcc gcttcagcgg cgagcagggt ggtgcgcctt atattcccgt gcgtttcgga    3300
cgtgtccgca catgggttct cggtagcccg gtccatcggg cggtgatcga gatcgaacgg    3360
atcagcgaca gctcgatcaa ggccaatttt catctctatg gtgagacggg cgagcggatc    3420
gccagcttga gcgatagccg gttccgacgc acctatctga agcagcacaa gacgctcgat    3480
ggacttgcct atcattatga aaccatcgcg ctaccctgg tgaaagatca gggtgcggcc    3540
ctggttgcac cgttgggtga tgttttcgca tgtcaggaac gtgagctgga caatgccacg    3600
gtgctgatcc aggcctgcgt gctcagcgcc ttctatgcgc tggccgagtg ccttgccggt    3660
caagatcggc gcgtgtcgct ggtcgatctg ccgggcgatg tgcggttgcg gcggttcctg    3720
accaatgccc tgcacagtct gaccgatagc ggctttgccc agtatgcgga tggcagctgg    3780
acgcttgaag atggcagcga tcttccgccc gcttccgagc tgatccggga actctatcgg    3840
gatttcccgg aacgcaccgt tgaactggtg atgatcaatg acgtgctgac agccgttaat    3900
gcagcgctca atcagcctgc aggtgttgtg gacgagggtt tggattggga cggggtgatc    3960
agcgaagcga cgctggacca tttcgccgtt cattccacgc tcgccaccga gagtcatagg    4020
gtgttgttga aggctgtgat cgactgtctc tcgaccttgg atgccgatgc gccgccgctg    4080
gtggtcgagc ttggcgccag ctcgcttcac cttagccgca agctcgccga tctggttcgt    4140
gcggctggcg gcaatctggt gatttacgag cctgaggcag gcctgcgccg caatctggag    4200
ctgtctttcg aggctgatcc gcgcgtcact gtcgtggacg caaagggatt ggaccagctt    4260
tcgcttttga aagcgccggt cgatctaatt gccagcgccc atgccgatct ttgccgcttg    4320
ctggatggtg aaatgctggc acggctcagc catggcgcct tggcctcggc ccgtcgcctt    4380
gtcgccgtgc aaccagcgcc cggcctattg catgatttcg ccttcggtct gctggatggt    4440
tggttcgaca ggacggtttc ggaggaattt ccgctcggcc gatttggcgg tagcgaagac    4500
tggatgaaat ccctgcaaca ggccggtttt cggcgcgccc atgccggca attgcaggtg    4560 gatggcggta gccttatcgt ggcggaagcc cagggtcggg ctgacgtggc cgagccatat    4620
gatgcgacgc gtcaggacgg tgggtcggtg atgaggttg tggccagcgg gccagtgatc    4680
atcgttcatg aaaaaactgc ggatcttgcc cggctttcgg cggcagcaag agcgcttggt    4740
ggttcccagg tgtctttgct gtgcctgtca ggcagctttg aaacggaccg gtcgatgctg    4800
gccgatgcac tgggcaaggc tggaccagcc gtgggcggaa tggtctggct gatgccggat    4860
accgatgcgg ctgcggatgg atcgctgctg ttgcaggaca gggtcggcgc tcttagcgcg    4920
ctggccatgg cgtttggcga tgttgcggca tcaacgtctg atgctgcgag gacgcttccg    4980
gtcactctgg ttctgcccgg cggtgcgccc gtcaccggct ttaccggcaa ggacttgacc    5040
cgctccagtc atgcgggggcc tgtcaatgca ggtctctggg cctttgcccg cgtattgcgc    5100
```

```
aatgagttcg acctgttcga catgcaggtc gtcgataccg gaccctccag caatacgctg    5160
gaaatcatgc tggactgggg catgcgcctg ctggccgcca agggcgacaa ccgcgaatgg    5220
ctggtggagc cggaaaccgg gcggatggcc gagattcgtg ccgtgcctgg tccggccccg    5280
ctgacggcgc agcgtaccgt tgcttttgag gcagcggtca ttcgccagca ggtgccgtcg    5340
caggtcgcca gcatccgctg ggaaagctgc ccggtcccag tcatcggtcc aaccgaagtg    5400
ctggtgaaga ccgcagcgac aggcttgaat ttccgcgacg tgatgtgggc catgggcctg    5460
ctgccggaag aagcgcttga ggacggcttt gccggggcct ccatcggcat ggaatttgcc    5520
ggtgaagtgt cgctgttggc ggcaaggtg agcgatcttg ccctcgggga caaggtgatg    5580
gcaatcgccg ctgcggcttt cggcacccat gtcaaggttg agcgggctgg ggtggcgaag    5640
ctgccggatg gcgtggaccc ggtatcggcg gcgaccattc cggtggtctt cctgaccgcc    5700
tattatgcca tccatgagct tgggcgggta cgtccgggcg aaaccatcct tattcacggt    5760
gccgctggcg gcgtcgggct tgcggctttg caggtcgccc ggcatttcgg cgccaagatc    5820
attgccacgg caggcaccgt cgaaaagcgg cgcttcctgg aaacgctggg ggcggaccat    5880
gtgttcgata gccgctcgct cggttttgtc ggcgatgtgc ttgacgtgac cggcggcgaa    5940
ggtgtcgatc tggtgttgaa ctcgctgttt ggcgaggcga tggaaaaatc cctgtcgctg    6000
gttaagccgt cgggcgtttc ccttgagctt ggcaagcgcg attattacgc cgacagcaag    6060
atcggcctgc ggccattccg gcgcaatgtc agttatttcg gcattgatgc cgaccaattg    6120
ctggtcctgc atcccgatct gtcgcgccgt atgctggccg aaatcggtgg cttgttcgag    6180
cagggcgtgt tcacgccatt gccgttccgc gccttcgaac acgatgagat tggtgatgcc    6240
ttccgcctga tgcagaatgc cggccatatc ggcaagatcg ttgtcctgcc gccggttgcg    6300
ggccgtgacc gcgtcgcggt aaagtctgcg cgccggatgg tggtcgatgc ggatggtatg    6360
catctggttg tcggcggtat cggcggtttc ggccttgccg cagccgattg gctggtagag    6420
cagggcgctc gccatatcgc cttatcgacg cggcgcgggc tggttgatgc ggagacgcag    6480
accgtggttg accgctgggc caagcagggc gtgacggcct atattcgcgg ctgcgacgtg    6540
accagtgaag cggccttgtc ggcgcttttg acggagcttc gcgccattgc gccgttgaag    6600
accgttatcc atgcggcaat ggtgctggac gatgccttca tctccaattt gacgcgggcg    6660
cgaaaccagc cggtgatcga cgtcaaggcc aagggtgctg tacttcttga ccggttgacc    6720
cggcaggacg ggatcgacaa tttcattctg ttttcgtcga tcaccaccta tgtcggcaat    6780
cccggtcagg gcaattatgt cgctgccaac ggcttcctgg aaggcttggc gcgggcgcgt    6840
cgcgccgatg gtctggctgg tcttgccatc ggcttcgggg caatcggcga tgcgggttat    6900
ctggcccgta atgcgcaggt taatgaacgg cttggacgcc ggatcggcaa gacggcgctg    6960
gatgcccgcg atgcgctttc ggcggtcggg cgctatattg ctgccgatac cggctctgtc    7020
gatgcagctg tggtgatgat ttccgaattc gactgggctg ctgcacattc gctttccgtg    7080
gtcaacgaac cgctgttttc gttgatcatg cgccgcagca accagcatgc cggtggcagt    7140
gagggtggcg agatcgatct ggtggcgctg attgatggca aggcgccggc tgcggcgcag    7200
gacgtgctgt ttacggtgct tgccggtgaa attgccgata cgctgcgggt gcccaaggaa    7260
agcatcgggc tgaacagcgt gctgaaggac atcgggctgg acagtttgat ggctgtcgaa    7320
ctggggatga atttcgagca gaataccggc tttgacattc ccctcagcag ccttgccgac    7380
aacgccactg tcggagacct gacgcgacgc ctctatgaaa aagtcagcct gcgcggacgg    7440
```

```
acaggcgaca aggatgaagc gctacctgag gacagcaaga tcatggacga tctgcatcgt    7500
cgccacagcg ggcaggacca gtaa                                           7524
```

<210> SEQ ID NO 14
<211> LENGTH: 2507
<212> TYPE: PRT
<213> ORGANISM: A. vitis strain F2/5
<220> FEATURE:
<221> NAME/KEY: MISC_FEATURE
<222> LOCATION: (1)..(2187)
<223> OTHER INFORMATION: avi4330

<400> SEQUENCE: 14

```
Met Phe Asp Leu Leu Arg Ala Gly Ala Cys Thr Val Ser Thr Leu Pro
1               5                   10                  15

Gly Asp Arg Trp Asp Ile Ala Arg Tyr Trp His Pro Glu Ile Gly Thr
            20                  25                  30

Pro Gly Lys Tyr Tyr Thr Phe Ala Ala Gly Val Met Asp Gly Ile Tyr
        35                  40                  45

Gln Phe Asp Pro Ala Leu Phe Gly Met Ser Arg Arg Glu Ala Ala Phe
    50                  55                  60

Met Asp Pro Gln Gln Arg Ile Leu Leu Glu Leu Thr Trp Arg Ala Leu
65                  70                  75                  80

Glu Asp Ala Asn Ile Pro Ala Asn Ser Leu Ser Gly Gln Asn Val Ala
                85                  90                  95

Val Tyr Val Gly Ala Ser Ser Phe Asp His Ala Asn Leu Ala Ala Glu
            100                 105                 110

Asp Pro Ala Gly Pro Gly Pro His Phe Met Thr Gly Asn Thr Leu Ser
        115                 120                 125

Val Val Ser Asn Arg Ile Ser His Val Phe Gly Leu Asn Gly Pro Ser
    130                 135                 140

Met Thr Val Asp Thr Ala Cys Ser Ser Ser Leu Val Ala Leu Asp His
145                 150                 155                 160

Ala Val Arg Ala Ile Ala Ser Gly Glu Val Asp Thr Ala Ile Val Ala
                165                 170                 175

Gly Val Asn Val Leu Val His Pro Leu Pro Phe Val Gly Phe Ala Gln
            180                 185                 190

Ala Arg Met Leu Ser Ile Asp Gly Leu Cys Lys Ala Tyr Ala Asn Asp
        195                 200                 205

Gly Ile Gly Tyr Val Arg Ala Glu Gly Gly Ala Val Leu Val Leu Arg
    210                 215                 220

Ser Ser Asp Lys Ala Arg Arg Glu Gly Asp Arg Ser His Ala Thr Ile
225                 230                 235                 240

Val Ala Ser Gly Thr Asn Ala Ala Gly Arg Thr Asn Gly Ile Ser Leu
                245                 250                 255

Pro Ser Arg Glu Ala Gln Ala Val Leu Leu Arg Ala Val Tyr Asp Asp
            260                 265                 270

Asn Gly Leu Asp Pro Asp Arg Leu Ala Phe Ile Glu Gly His Gly Thr
        275                 280                 285

Gly Thr Lys Val Gly Asp Pro Ala Glu Val Trp Ser Leu Gly Thr Val
    290                 295                 300

Ile Gly Gln Arg Arg Lys Glu Pro Val Trp Ile Gly Ser Ile Lys Thr
305                 310                 315                 320

Asn Ile Gly His Thr Glu Pro Ala Ser Gly Leu Leu Gly Val Met Lys
                325                 330                 335
```

```
Ala Met Met Ala Leu Gln His Asp Leu Leu Pro Ala Ser Leu His Phe
            340                 345                 350

Asn Glu Pro Asn Asp Thr Ile Asp Phe Asp Gly Leu Asn Val Arg Val
            355                 360                 365

Ala Ser Gln Ala Val Ala Leu Ala Arg Asp Gly Ala Pro Arg Leu Ala
            370                 375                 380

Gly Ile Asn Ser Phe Gly Phe Gly Gly Ala Asn Ala His Val Val Ile
385                 390                 395                 400

Ala Asp Pro Gln Arg Pro Asp Leu Val Pro Gly Leu Ala Gln Asp Ala
                405                 410                 415

Ala Asn Pro Ala Gly Ala Gly Arg Leu Phe Met Ala Ser Ala His Ser
            420                 425                 430

Gln Glu Ser Leu Lys Ala Leu Leu Asp Ser Tyr Asp Lys Ala Phe Ala
            435                 440                 445

Ala Ala Gly Ser Asp Gly Asp Leu Glu Asp Leu Ile Ser Ala Ala Ala
            450                 455                 460

Ser Asn Arg Ala Pro Leu Arg His Arg Phe Val Ala Ser Gly Ser Ala
465                 470                 475                 480

Asp Ala Ile Val Lys Ala Val Gln Glu Arg Leu Ala Thr Ala Lys Thr
                485                 490                 495

Gly Gly Glu Thr Gly Glu Ala Leu Ser Arg Asn Gly Lys Leu Ala Phe
            500                 505                 510

Val Phe Ser Gly Asn Gly Ala Gln Trp Ala Gly Met Gly Leu Asp Ala
            515                 520                 525

Tyr Arg Ala Asn Ala Arg Phe Arg Glu Ser Tyr Glu Arg Ile Ala Thr
            530                 535                 540

Leu Phe Thr Ala His Ser Asp Leu Asp Leu Val Ala Ala Leu Thr Asp
545                 550                 555                 560

Pro Asp Leu Glu Ala Arg Leu Lys Asp Thr Arg Leu Ala Gln Pro Met
                565                 570                 575

Leu Phe Ala Ile Gln Ala Ser Leu Ser Asp Ala Leu Gln Leu Ala Gly
            580                 585                 590

Leu Val Pro Asp Ala Val Tyr Gly His Ser Val Gly Glu Val Ala Ala
            595                 600                 605

Ala Tyr Val Ser Gly Ala Leu Ser Leu Lys Asp Ala Val Cys Val Ile
            610                 615                 620

Ala Lys Arg Ser Gln His Gln Ala Val Leu Ala Gly Glu Gly Thr Met
625                 630                 635                 640

Ala Ala Leu Lys Leu Gly Glu Ala Asp Ala Arg Ala Met Leu Ala Glu
                645                 650                 655

Leu Gly Phe Asp Asp Leu Thr Ile Ala Ala Ile Asn Ala Pro Asn Ser
            660                 665                 670

Val Thr Val Ser Gly Arg Glu Asp Ala Ile Arg Ala Leu Arg Glu His
            675                 680                 685

Ala Arg Lys Gln Arg Val Pro Ala Gln Val Leu Asp Ile Asp Tyr Pro
            690                 695                 700

Phe His His Pro Leu Ile Asp Lys Ala Lys Ala Ala Phe Ser Ala Asp
705                 710                 715                 720

Pro Pro Leu Ile Thr Pro Arg Gln Thr Thr Leu Pro Phe Ile Ser Thr
                725                 730                 735

Val Thr Gly Glu Gln Leu Glu Gly Thr Ala Leu Thr Ser Asp Tyr Trp
            740                 745                 750

Trp Lys Asn Val Arg Gln Pro Val Gln Phe Gln Gly Ala Thr Glu Ala
```

```
                755                 760                 765
Ala Ile Ala Leu Gly Cys Thr Val Phe Val Glu Ile Ser Pro Arg Ala
        770                 775                 780

Ile Leu Gly Gly Tyr Val Ser Glu Thr Ala Gln His Val Ser Ser Thr
785                 790                 795                 800

Val Ala Val Ser Ala Ser Leu Ser Arg Glu Ala Pro Asp Glu Thr Val
                805                 810                 815

Asp Pro Val Ala Arg Ala Leu Ala Arg Ala Val Ala Ser Gly Ala Lys
        820                 825                 830

Val Asp Glu Ala Lys Val Phe Gly Pro Arg Ala Asp Ile Val Leu
                835                 840                 845

Pro Gly Val Pro Phe Glu Arg Ala Asp Leu Arg Pro Glu Pro Thr Ser
        850                 855                 860

Asp Arg Val Asp Leu Tyr Gly Arg Phe Gly Gln Thr Ala Tyr Arg Leu
865                 870                 875                 880

Ser Gly Trp Arg Val Asp Leu Asn Gly Gly His Trp Lys Asn His Leu
                885                 890                 895

Asp Ala His Leu Phe Pro Asp Leu Ala Glu His Val Val Asp Gly Arg
        900                 905                 910

Ala Ile Leu Pro Gly Ser Gly Phe Val Glu Ile Ala Ile Ser Ala Ala
                915                 920                 925

Gln Ala His Phe Gly Ser Asp Gln Leu Glu Ile Ser Asn Val Glu Ile
        930                 935                 940

Met Arg Pro Leu Glu Leu Ser Asp Ser Arg Ile Val Glu Leu Ser Thr
945                 950                 955                 960

Leu Ile Ser Ala Ala Thr Gly Asp Leu Gln Ile Arg Ser Arg Glu Arg
                965                 970                 975

Leu Ser Asp Asp Asp Trp Thr Val Asn Ala Val Ala Arg Val Arg Lys
        980                 985                 990

Leu Thr Ala Ser Glu Leu Asp Asp  Ala Val Asp Phe Asp  Leu Ser Ser
                995                1000                1005

Pro Thr  Ser Glu Leu Asp Lys  Ser Ala Ala Tyr Arg  Thr Ala Arg
        1010                1015                1020

Asn Phe  Gly Leu Asp Tyr Gly  Pro Arg Phe Gln Leu  Leu Glu Lys
        1025                1030                1035

Ala Ile  Cys His Gly Glu Arg  Leu Val Glu Val Phe  Leu Lys Pro
        1040                1045                1050

Ala Ala  Ala Pro Gly His Pro  Leu Leu Arg Tyr Asn  Leu Asn Pro
        1055                1060                1065

Met Ser  Val Asp Ala Met Phe  His Gly Leu Val Ala  Leu Phe Gly
        1070                1075                1080

Arg Phe  Ser Gly Glu Gln Gly  Gly Ala Pro Tyr Ile  Pro Val Arg
        1085                1090                1095

Phe Gly  Arg Val Arg Thr Trp  Val Leu Gly Ser Pro  Val His Arg
        1100                1105                1110

Ala Val  Ile Glu Ile Glu Arg  Ile Ser Asp Ser Ser  Ile Lys Ala
        1115                1120                1125

Asn Phe  His Leu Tyr Gly Glu  Thr Gly Glu Arg Ile  Ala Ser Leu
        1130                1135                1140

Ser Asp  Ser Arg Phe Arg Arg  Thr Tyr Leu Lys Gln  His Lys Thr
        1145                1150                1155

Leu Asp  Gly Leu Ala Tyr His  Tyr Glu Thr Ile Ala  Leu Pro Leu
        1160                1165                1170
```

-continued

```
Val Lys Asp Gln Gly Ala Ala Leu Val Ala Pro Leu Gly Asp Val
175                 1180                1185

Phe Ala Cys Gln Glu Arg Glu Leu Asp Asn Ala Thr Val Leu Ile
    1190                1195                1200

Gln Ala Cys Val Leu Ser Ala Phe Tyr Ala Leu Ala Glu Cys Leu
    1205                1210                1215

Ala Gly Gln Asp Arg Arg Val Ser Leu Val Asp Leu Pro Gly Asp
    1220                1225                1230

Val Arg Leu Arg Arg Phe Leu Thr Asn Ala Leu His Ser Leu Thr
    1235                1240                1245

Asp Ser Gly Phe Ala Gln Tyr Ala Asp Gly Ser Trp Thr Leu Glu
    1250                1255                1260

Asp Gly Ser Asp Leu Pro Pro Ala Phe Glu Leu Ile Arg Glu Leu
    1265                1270                1275

Tyr Arg Asp Phe Pro Glu Arg Thr Val Glu Leu Val Met Ile Asn
    1280                1285                1290

Asp Val Leu Thr Ala Val Asn Ala Ala Leu Asn Gln Pro Ala Gly
    1295                1300                1305

Val Val Asp Glu Gly Leu Asp Trp Asp Gly Val Ile Ser Glu Ala
    1310                1315                1320

Thr Leu Asp His Phe Ala Val His Ser Thr Leu Ala Thr Glu Ser
    1325                1330                1335

His Arg Val Leu Leu Lys Ala Val Ile Asp Cys Leu Ser Thr Leu
    1340                1345                1350

Asp Ala Asp Ala Pro Pro Leu Val Val Glu Leu Gly Ala Ser Ser
    1355                1360                1365

Leu His Leu Ser Arg Lys Leu Ala Asp Leu Val Arg Ala Ala Gly
    1370                1375                1380

Gly Asn Leu Val Ile Tyr Glu Pro Glu Ala Gly Leu Arg Arg Asn
    1385                1390                1395

Leu Glu Leu Ser Phe Glu Ala Asp Pro Arg Val Thr Val Val Asp
    1400                1405                1410

Ala Lys Gly Leu Asp Gln Leu Ser Leu Leu Lys Ala Pro Val Asp
    1415                1420                1425

Leu Ile Ala Ser Ala His Ala Asp Leu Cys Arg Leu Leu Asp Gly
    1430                1435                1440

Glu Met Leu Ala Arg Leu Ser His Gly Ala Leu Ala Ser Ala Arg
    1445                1450                1455

Arg Leu Val Ala Val Gln Pro Ala Pro Gly Leu Leu His Asp Phe
    1460                1465                1470

Ala Phe Gly Leu Leu Asp Gly Trp Phe Asp Arg Thr Val Ser Glu
    1475                1480                1485

Glu Phe Pro Leu Gly Arg Phe Gly Gly Ser Glu Asp Trp Met Lys
    1490                1495                1500

Ser Leu Gln Gln Ala Gly Phe Ala Ala Ala His Ala Arg Gln Leu
    1505                1510                1515

Gln Val Asp Gly Gly Ser Leu Ile Val Ala Glu Ala Gln Gly Arg
    1520                1525                1530

Ala Asp Val Ala Glu Pro Tyr Asp Ala Thr Arg Gln Asp Gly Gly
    1535                1540                1545

Ser Val Asp Glu Val Val Ala Ser Gly Pro Val Ile Ile Val His
    1550                1555                1560
```

```
Glu Lys Thr Ala Asp Leu Ala Arg Leu Ser Ala Ala Ala Arg Ala
    1565                1570                1575

Leu Gly Gly Ser Gln Val Ser Leu Leu Cys Leu Ser Gly Ser Phe
    1580                1585                1590

Glu Thr Asp Arg Ser Met Leu Ala Asp Ala Leu Gly Lys Ala Gly
    1595                1600                1605

Pro Ala Val Gly Gly Met Val Trp Leu Met Pro Asp Thr Asp Ala
    1610                1615                1620

Ala Ala Asp Gly Ser Leu Leu Leu Gln Asp Arg Val Gly Ala Leu
    1625                1630                1635

Ser Ala Leu Ala Met Ala Phe Gly Asp Val Ala Ala Ser Thr Ser
    1640                1645                1650

Asp Ala Ala Arg Thr Leu Pro Val Thr Leu Val Leu Pro Gly Gly
    1655                1660                1665

Ala Pro Val Thr Gly Phe Thr Gly Lys Asp Leu Thr Arg Ser Ser
    1670                1675                1680

His Ala Gly Pro Val Asn Ala Gly Leu Trp Ala Phe Ala Arg Val
    1685                1690                1695

Leu Arg Asn Glu Phe Asp Leu Phe Asp Met Gln Val Val Asp Thr
    1700                1705                1710

Gly Pro Ser Ser Asn Thr Leu Glu Ile Met Leu Asp Trp Gly Met
    1715                1720                1725

Arg Leu Leu Ala Ala Lys Gly Asp Asn Arg Glu Trp Leu Val Glu
    1730                1735                1740

Pro Glu Thr Gly Arg Met Ala Glu Ile Arg Ala Val Pro Gly Pro
    1745                1750                1755

Ala Pro Leu Thr Ala Gln Arg Thr Val Ala Phe Glu Ala Ala Val
    1760                1765                1770

Ile Arg Gln Gln Val Pro Ser Gln Val Ala Ser Ile Arg Trp Glu
    1775                1780                1785

Ser Cys Pro Val Pro Val Ile Gly Pro Thr Glu Val Leu Val Lys
    1790                1795                1800

Thr Ala Ala Thr Gly Leu Asn Phe Arg Asp Val Met Trp Ala Met
    1805                1810                1815

Gly Leu Leu Pro Glu Glu Ala Leu Glu Asp Gly Phe Ala Gly Ala
    1820                1825                1830

Ser Ile Gly Met Glu Phe Ala Gly Glu Val Val Ala Val Gly Gly
    1835                1840                1845

Lys Val Ser Asp Leu Ala Leu Gly Asp Lys Val Met Ala Ile Ala
    1850                1855                1860

Ala Ala Ala Phe Gly Thr His Val Lys Val Glu Arg Ala Gly Val
    1865                1870                1875

Ala Lys Leu Pro Asp Gly Val Asp Pro Val Ser Ala Ala Thr Ile
    1880                1885                1890

Pro Val Val Phe Leu Thr Ala Tyr Tyr Ala Ile His Glu Leu Gly
    1895                1900                1905

Arg Val Arg Pro Gly Glu Thr Ile Leu Ile His Gly Ala Ala Gly
    1910                1915                1920

Gly Val Gly Leu Ala Ala Leu Gln Val Ala Arg His Phe Gly Ala
    1925                1930                1935

Lys Ile Ile Ala Thr Ala Gly Thr Val Glu Lys Arg Arg Phe Leu
    1940                1945                1950

Glu Thr Leu Gly Ala Asp His Val Phe Asp Ser Arg Ser Leu Gly
```

-continued

```
             1955                1960                1965
Phe Val Gly Asp Val Leu Asp Val Thr Gly Gly Glu Gly Val Asp
             1970                1975                1980
Leu Val Leu Asn Ser Leu Phe Gly Glu Ala Met Glu Lys Ser Leu
             1985                1990                1995
Ser Leu Val Lys Pro Phe Gly Arg Phe Leu Glu Leu Gly Lys Arg
             2000                2005                2010
Asp Tyr Tyr Ala Asp Ser Lys Ile Gly Leu Arg Pro Phe Arg Arg
             2015                2020                2025
Asn Val Ser Tyr Phe Gly Ile Asp Ala Asp Gln Leu Leu Val Leu
             2030                2035                2040
His Pro Asp Leu Ser Arg Arg Met Leu Ala Glu Ile Gly Gly Leu
             2045                2050                2055
Phe Glu Gln Gly Val Phe Thr Pro Leu Pro Phe Arg Ala Phe Glu
             2060                2065                2070
His Asp Glu Ile Gly Asp Ala Phe Arg Leu Met Gln Asn Ala Gly
             2075                2080                2085
His Ile Gly Lys Ile Val Val Leu Pro Pro Val Ala Gly Arg Asp
             2090                2095                2100
Arg Val Ala Val Lys Ser Ala Arg Arg Met Val Val Asp Ala Asp
             2105                2110                2115
Gly Met His Leu Val Val Gly Gly Ile Gly Gly Phe Gly Leu Ala
             2120                2125                2130
Ala Ala Asp Trp Leu Val Glu Gln Gly Ala Arg His Ile Ala Leu
             2135                2140                2145
Ser Thr Arg Arg Gly Leu Val Asp Ala Glu Thr Gln Thr Val Val
             2150                2155                2160
Asp Arg Trp Ala Lys Gln Gly Val Thr Ala Tyr Ile Arg Gly Cys
             2165                2170                2175
Asp Val Thr Ser Glu Ala Ala Leu Ser Ala Leu Leu Thr Glu Leu
             2180                2185                2190
Arg Ala Ile Ala Pro Leu Lys Thr Val Ile His Ala Ala Met Val
             2195                2200                2205
Leu Asp Asp Ala Phe Ile Ser Asn Leu Thr Arg Ala Arg Asn Gln
             2210                2215                2220
Pro Val Ile Asp Val Lys Ala Lys Gly Ala Val Leu Leu Asp Arg
             2225                2230                2235
Leu Thr Arg Gln Asp Gly Ile Asp Asn Phe Ile Leu Phe Ser Ser
             2240                2245                2250
Ile Thr Thr Tyr Val Gly Asn Pro Gly Gln Gly Asn Tyr Val Ala
             2255                2260                2265
Ala Asn Gly Phe Leu Glu Gly Leu Ala Arg Ala Arg Arg Ala Asp
             2270                2275                2280
Gly Leu Ala Gly Leu Ala Ile Gly Phe Gly Ala Ile Gly Asp Ala
             2285                2290                2295
Gly Tyr Leu Ala Arg Asn Ala Gln Val Asn Glu Arg Leu Gly Arg
             2300                2305                2310
Arg Ile Gly Lys Thr Ala Leu Asp Ala Arg Asp Ala Leu Ser Ala
             2315                2320                2325
Val Gly Arg Tyr Ile Ala Ala Asp Thr Gly Ser Val Asp Ala Ala
             2330                2335                2340
Val Val Met Ile Ser Glu Phe Asp Trp Ala Ala Ala His Ser Leu
             2345                2350                2355
```

| | | | | | | | | | | |
|---|---|---|---|---|---|---|---|---|---|---|
|Ser|Val|Val|Asn|Glu|Pro|Leu|Phe|Ser|Leu|Ile|Met|Arg|Arg|Ser|
| |2360| | | |2365| | | |2370| | | | | |

Ser Val Val Asn Glu Pro Leu Phe Ser Leu Ile Met Arg Arg Ser
    2360                2365                2370

Asn Gln His Ala Gly Gly Ser Glu Gly Gly Glu Ile Asp Leu Val
    2375                2380                2385

Ala Leu Ile Asp Gly Lys Ala Pro Ala Ala Gln Asp Val Leu
    2390                2395                2400

Phe Thr Val Leu Ala Gly Glu Ile Ala Asp Thr Leu Arg Val Pro
    2405                2410                2415

Lys Glu Ser Ile Gly Leu Asn Ser Val Leu Lys Asp Ile Gly Leu
    2420                2425                2430

Asp Ser Leu Met Ala Val Glu Leu Gly Met Asn Phe Glu Gln Asn
    2435                2440                2445

Thr Gly Phe Asp Ile Pro Leu Ser Ser Leu Ala Asp Asn Ala Thr
    2450                2455                2460

Val Gly Asp Leu Thr Arg Arg Leu Tyr Glu Lys Val Ser Leu Arg
    2465                2470                2475

Gly Arg Thr Gly Asp Lys Asp Glu Ala Leu Pro Glu Asp Ser Lys
    2480                2485                2490

Ile Met Asp Asp Leu His Arg Arg His Ser Gly Gln Asp Gln
    2495                2500                2505

<210> SEQ ID NO 15
<211> LENGTH: 11899
<212> TYPE: DNA
<213> ORGANISM: Avs locus

<400> SEQUENCE: 15

```
gtcgccatga cccagcgata aatcgtggaa tggtcaaccg cgacgcccct ttcagccatc        60
atctgttcaa gatcgcggta gctcacccca tagcggcaat accagcgaac tgcccacaag       120
atcacctcgc cctgaaaatg acgccacttg aaatcgctca tcaaaagtct cgctgaaaac       180
tatctccctt atttccagca caaacggaat ctttgcgaca gagccgtatt tccggccttt       240
gatggttacc accatctcat cgaggtgcca tttatcggca aagccgccct ttgagcgccg       300
gcgaagcaac gcagcaaact cggagccaaa tttggcggcc cattccgata ctgtctggaa       360
cgaaacgtca ataccgcgtt cggccagcaa atcctcgaca tgccgcaggc tcaatggaaa       420
ccggaagtac agccaaaccg cgtgagcgat aatctcggct ggaaagcggt gacgtttgta       480
acgataggag gcgaaggtag acgaagaaat gttcatgccc actgctctat cgtacaaaac       540
ttaaggcgaa actgccgctc agggcgcaag gcttatacta tagcctgact tgtattcgat       600
tggcagaaaa aggcgatgat attccctgaa tgtctcgtct ggatcgagat cggcgaacaa       660
atccggatga agccattttg cgatttgttg tatggcgatg aattcataag ggctattgta       720
gaactgatgc catatgccat ggaaactgcg ttttttgacc gctttggtgc aatataggc        780
atttcttgtc gtgaaccatt ccagttttcg ttcggcttcc tgtctgttgg cacccggccc       840
caggggtatc cagtgtccac ccggaacata agcttcccaa ttggcgctcg tgaccacaac       900
ctgatccggg tcggcagcaa tcacctgttc cgggttcaat tgtccgaagg ttccgggaag       960
aaaatcaccg ccgatattgt gcccgccggc gattcgaca tagcgaccaa aattctcatt      1020
gccaaaggtg aggcagcaat catccgcata accgccaatc cgctcgacaa agacattcgg      1080
tcgtgcgggc ttttttgtt caatcacatc cgtcacttgc acaatgcct ttttcctgaa       1140
ggcaataatt tcctcggcgc gcttttcacg tccatgatc tcgcccaaaa ggcggattgt       1200
```

```
tggttcggta ttgtgaaggg gttgatgccg gaaatcgata taaagaaccg gtattcccag    1260
tgatgccagc ttttcgatat attcggactc tttgctggca cgctgggttt cgagattcaa    1320
aagcacaaca tcaggctttt gaacaatggc agactcaaga tcaatcagac ctgcttcctt    1380
gccgccaaag gttggcagtt gggccagttt cggaaacttc gcgacatatt gggcataggt    1440
tgcggggtcg gcttcaatga ggtcattttt ccatcctgcc agaaacgcca gaggattctc    1500
ggactccaat gacgcgacaa gatagagctg ccgcccttcg cccaacaaca tgcgatggac    1560
aggaacaggc aatgacacct gccgaccagc aatgtctgtc acggtgatgc gatgcggcgt    1620
tgttgctgca ttggatgttt gagccgctgg ctcctgtgcc acagcagatg gcatctgcgc    1680
gacaagacac gacagcagag ccgcaaagag agtggtggct ggttttatca ccgttttatc    1740
ctatgcggtt gggtaagggg ccgcttttga gcaagagcga caggccgata aaaatgaca    1800 ggatgtaaca cgccgatacc agggaaaatg cggtatcagc accccaaagc tgcatggacc    1860
caacaccggc tgctataccc agaatggaag cgatttgctg ccagctttgc gcacggccca    1920
aaatttcacc ttgccgattg aaggctgtgg actgggaaag acgcgaggta agaaccggtg    1980
tcgtaccacc aagcagaatg ccccagacaa agtataatcc tgcaaaaacg gaacgagggg    2040
ttgtgtagcc cgctatcaaa gcgatgcttg cgcaggccag agcgatcgcg gtgtttgccg    2100
ccaacacaaa gccaaggctg cgcattttga acagacgcgc ccagaggggg cgccaatca    2160 caaaaccaaa cgccatgagc ccgtagctga ggccaataat ccagtggttg gctccgaaag    2220
cttgggtcat gtagagcgaa acggcacttt gcagcaccat tcggctggcc aacaatacgc    2280 aaaatcaaaac cagcaaccccg acgactggtg cagaactttc tggatggccc ggggtgagcg    2340
cgcttgaagc ggagcgcggt gcattctgtc tgatgggcgg gatgggcaat gttgcccagg    2400
caacaagggc acatagacca catacggccc cggccgtgat attaacggcc gcgaatggca    2460
ttgcatccag aatgagacca cccgcaaatg cgccgcccag cgaaccgaca ttggtcgcca    2520
cctgcaacca ggcgaacaga ctggcgcgat cacgcccgct attgacctgc acggcatagg    2580
cttgcgcggg cgcaatatag ccggcgaaag ccccctgtaa gaaccgcaga acaggatga    2640 cccagacatc ttgggcaagc gcaatcagaa gctgggtgat cgccaacccc gccaaggccc    2700
gaaccatcat caagcgattg ccatagcggt caccccatacg ccccccagaat gcgctggtga    2760 gggaaatgcc aagcatgggg caaatataaa ccccgatact tgccaatccg aacgccgtat    2820
ccgacgggct gagtaccctg atctgcagcg gccagaaagg accgctcatt tccatggctc    2880
ccatggaaat gaactggagc gcaaacagca gcagaaacac aggcgtgctt gccctgagca    2940
tggcaaaagc gttcagcatt cacggccaac cagaggattg ggcagctcat gctccacccg    3000
atagtcgcta tatcgctgga gatgcatggt gagaaccgac cgggtgggcc atttttttc    3060 aagcagggca tctcgttctt cttgccagaa cgtgtccgaa gacacacgag gccgcaatgt    3120
ttcaaacgcc tcttgcgtta cctctttgat cactgtccag agcctatcat tgccgatact    3180
atagtgctgg gtcaggcaca gagcaatttc atgcagatgg catataaagc aggcgtcgat    3240
caaaaacgag cgaaccagcc caatgtcatc gtcaaaggtg gtgggcaaaa tcccagcacg    3300
ctgaaagggt ttgaggtgat agccacgctg tttgagcaga ggcgcaaagc tgcggccatc    3360
accaaaatcc cgaatgatca gcttttccgc agaaccggaa ggatcaaaca cgatggtggt    3420
gttttgctga tgggcctcaa aagcgatgcc ataaagaaga tacatcgcca acgcaggccg    3480
aaccaccacc tcaacatacc ggcggaaaaa gccgacaacg cttgcctgtt cctcattgcc    3540
gtaacgggca atcagctcgc agatcaatgg tcgtccatcc ttgggacttg cacttagaag    3600
```

```
tgcggcgacc gtcaccgcat agcgtccatc ctcgcgcttt aaaggctggg cgttgcgata   3660
gaccaccgac aaaaatcgcc cgcgatgctc atcgccggta tcgggatcgt gcagaatggc   3720
tcccaattct tcggtgaaga tttccaattg tgcggccatg tccggttcat tggccagaat   3780
atcggtgatc aacgtggaaa gccgaggccc catgtgaatg gatttggcct gcaagctgcg   3840
ctgctcgctg gtgagccaga tggcaaccgg caacttgatg aaagggcgca acgtttcatc   3900
gtccggtaac atggtccgaa atgacatgga tggcgaggtg tcaatgtctg gcccgtccaa   3960
cagcaagatg ccagaggcga tttcctgtcc aaattcgcgg cggacaaaat gctcgaggtg   4020
ccatccgtgg atgggcaaag gaatccagtc ttgcgctgat ttgccctgtg cgctcagatg   4080
gtctttccac gcggcaaaca attcgggaaa ctgggcagaa accagtcat tgtaatcagt    4140 cacatgtggc atttttttcca cataggccca accccgacgc aaggccgcaa tccgaccgg   4200 caccttggcc ccgaattcag gcgaaagggc aacaacctct tcgggctgca aactcggttt   4260
tgccttccat gtcggataaa acggatgacc ttcgagcgca ccccactggt caatcagcat   4320
tgccgccaga tgtgcaggca atgaccgta gagatagccc agaaaatcca ccgcaccgga    4380
ttgtttgatc ttctcattca ggctcgcagc ccagacctgc cggtgtcggc gggccagcat   4440
atcattgttg atgctgtcgg cgatatcgcg catcaaaacc tcaagcccat caggggccgg   4500
agagatggac aacgaagcga acacttcccg cagcaaagca tcgggatggt caatcccggc   4560
atggccgccg tcggcgtcga gaatttcaat ctcgccacgg ttttgcaagg tgccagcggg   4620
tgccgcatgc aaatgtttaa aatgcagcac acggcgcgtg ttccacagcg caaccaggc    4680 ttgatgcttg tcacgcgacc agagcaacgc ttcaggagcc agaagacgtt ctgcaaacag   4740
gcagcgaaca aggcgactga ttgcattggc aacggcaaaa tcccgcaacg gctggtcatc   4800
ggtctgcgca tggatgtcaa acaaaggcga aagcaaatgg gtcatcaggc agcctccagc   4860
caatcatcag gaaccgggct taatccatcc ggcaaagcac catgatagtg gcgcgcccac   4920
gtgtaggttt tcgagatggt tggaatcggt accgccagcc gctctgcgat cttgaccagc   4980
aatgcctgcc cgcatgcaac atcctcatga aaggcacggc tttgcagatc gatcaaccag   5040
ccttgaccat gatgattggg gatcagcggc aattgaattc ccgcataggc gctgtttgtt   5100
ctgagcaggg aatacatcgt ttgactatcg gcaatctgat cgccataggc ttcaatcagt   5160
tcctgccgca aggtttgac ggagctgaga tcaagaccgg ttcgggtcgc aatcgcctga    5220
catatggcct gatttttcggc atcgaacatt tcgagcaagc gcgcgccttc ctcagggcaa   5280
tcactccacc agcacagcgg ctcggagaac ggtttacgct cccagggagc gcccggcccc   5340
agcaggccgt agagcaccgc tggatgcatc agcgcattgc cgggtgtcag ggtgatttcc   5400
agatagtcct gcaaaagggt tacaggcgca ttgtaaagtg cggtcagcat tgtttgcaga   5460
gccttggcac tttgggcgga ttcccgccga tgaaggccag caaacaaatg ggctttagcg   5520
ccgcccatgc gaacgctctg tccggcaaca aggtcgtagg cgatatgcgg cacatccttc   5580
aaaccccaga tgaccacatt atcccttgcg cctaagtgat cggcagccag ccagtcaaaa   5640
ccgcaaaagc ccggaatagc acccacgaaa acctgcttgg tgctggagat actgcctgcg   5700
atccgctgca aaacagcgga tctggcatgg gctggctggg taatgacaat cagatcagcg   5760
ttcccaaccg ctttatcggg gttgttgcca acgtaatcag gacgcccgga catacccccga  5820 ccatccggca aaaagcctg ccatggagca ggatttccag cccaattggc ggcaagagtg    5880
tcattctccg tcaaaacgga gagatggacc tgcggatttt gcttaaaaag cacggcattc   5940
```

```
aaatgcccgg tgcggcctgc gccgcaaatg gcgaccctca tgccgcacct gccaagccat    6000
tgaaccaacc atccaattga gctgcgattg ccggattgag aagcccgcgc ttttccatcc    6060
actcatcgtc aaacacggat gccaggtatt tttcaccccc atctgcgacg gctgtaacaa    6120
ttgtgccgct caatttaccg gatgcgatga attcgagagc tttgtaaatt gtaccccgg     6180 ttgatccacc aacgagaata cctttgcgtc gggcaatata gcgtgccgtt tcaaatgctt    6240
gcgtatcggt gacctgaaca ccttcatcaa tgcagctata atccagaacc ttgccgactt    6300
catcgcctgc gggcgtacct gtgccagatt ggtaatagga atgccccggc ttaccaaaaa    6360
caatggaacc agcaggctca accgcaattg tcttgatggc gggattgagg cgcttgaggc    6420
gctgggatat gcccgtcatc gacccacccg tacccacgca accaacaaag gcatccaatc    6480
catcaggcag ttgtgccatc aactcatcca caaatccggc atagccgtca ggattggcgg    6540
gattgtcgga ctggttcatg aacagtgcac caggcagttg cgcgccgagc tgggcggcca    6600
gtctctgcct ttcaacgacg gccacttcat cttcgcgata gtcgccttca acatagcgaa    6660
tttcggcacc caaggcccgc atcatccgga ttttatccgg cgcggcgtga tgatccacga    6720
ccgcgataaa gcgaagacca aactccagcg ccgcaagagc cagacctgtg cccgtgttgc    6780
ctgatgagga ttcaacgatc gtgccgccac gcggcaggcg cccatccgcc aaggccgcaa    6840
ccaccatgct gcgcgccatg cggtctttca ttgagccgcc aggattgttc ttctccattt    6900
tgagcaaaag ttttgcattg cttgttgcca gatcaagcgc gatcagggg gtctggccaa     6960 tcaattgcgt gacggttgta tagagcatag tacctcctca caggtatccg gaataagttc    7020
ggacagtcca tctgcggtcc tcctgacaca taagcggatt ggcatggggt ggcggtgaaa    7080
ctggttttcc atcagatcca tctgatagcc gccggtattg acatagatga gcaaatcacc    7140
agcttgcggg gtaatcggaa agtcgagcca gcggttggag acaatatctt catcaaggca    7200
gctatgtccg gcaagatagg gcgcacagg agtggtgcgt gcagcttccg gcccgtgcgg     7260
caccacaatg ggatcgatca gaaattctga tgcgaaccat gtttcgcatg cactgaagct    7320
gctgccctcc acaaaaattg ctgctgactg cgcacccagt gccttcactc tcgtcactct    7380
gaaagccgtg attgcagtct gatccgcaag ggcccgcccc ggctccatcc ccagcgtaag    7440
attttcctga cggaaatatg ttgcgacatc gcgcccgtcc tgcattttgg attgcaacag    7500
gtgagttaac cactccgttg cgcaaacagg tcctccatag ggataaaaag actgtggcag    7560
atggttggtg cgataatcct gcgccgtttg cgcctccaga aaggcggcgt aggtcgggtg    7620
atcgacatat tgcaccggca acccaccacc aatatcgatc atgcggggag aaagccccat    7680
gccgcgcgct ttggcaatga gatccgctgc ttcattcaat gcttcgatgc gcgccttaac    7740
gctataacca ctcaagtgga aatggattcc atcaaatcgt agggctgggg tgcctgccaa    7800
acgatgcagg cacgaaacaa cgtcttgagc atccatgccg aagcggcttt gcccttgatt    7860
ttggggcctt aatctcaaaa gcacgggctg agggtcaccg cgcgcttggca attccttcaa    7920 aatatcatcg aattcctcaa cggaatcgat ggaaatcagg ccttgcagg ccatcaacgc     7980 tctatgaaat gtcgatgttt tggcaggacc ggtcgcaaca atatcggcac cctttgcacc    8040
caatgccaag gcatcctgca actcgtacag gctggagaca tcaacgcctc cttcagcctg    8100
aagggcagct cccataagat tcacagactt gttgaccttc acaccataat aaattctgca    8160
tggaacttga ctgccgctca atatggcctg caaagccaga agattatcgg ccagcagatc    8220
aggccagatc aaatggagcg gcgagccaaa tctgttgaat ccttcccgca actgttcatg    8280
cttgttttca ataaaatctg cgacctcgtc atgaatcagg ggcgtcagag tgtgagattg    8340
```

```
cttggagcca agtctcatga cagcaccgcc ctgccgcctt gcatcgccga atccatggta   8400
gccacaattc cggctaatac cgcgagcggt acatcacata cagggtaatc atccgcgaag   8460
acgtgacgtg tcgttttgat cggaaatttt ttgccggacc gcgccatggc aaaaatatcg   8520
tctggtgtaa tgcattcctc aggccgccaa ctcgtgacag acacacgctc ataatccagg   8580
aggacaacag gaatgacagc gagattgagc tgccttgcga cctcaagccg gtgatgccca   8640
tccatcacca gaaactgagt gcgctcgacc gcaatagggc gtgtccagat ctgctgacgt   8700
aaaatggttt ggcgcaaatt ctcaacaacg ctttgatcga cttcttcagt gtcgacaagt   8760
tttttgggag aggcaaaatg atatggcata aaatacagcc cttcggtgaa aatcgctatt   8820
tccgaaaata tgactacata aatcatgttt aacatgtagc gtttatttcc agatgtcaat   8880
ttacaatcct aaaaaaatat ccagtataaa cagatggata aaagatatct ggctatttca   8940
ttcgcgatga aaataaaatc ttgactctta atgtcatgtt caatacccag ctgcttgggc   9000
gtgtatttta aagagcatag ttcacggcaa ccttgccggt tctgctgagg gggatgctga   9060
catgatgggt ttgaaaagtg gcgttgccat gggtgcaatt ctggctgctc tcggcactgt   9120
tgcgcaggca gaagaggaca cggttctcaa gccaattgtt gttgagggac aatcctcatc   9180
gcccaacgca accataggca aacagagcga accttatgca gggggcatgg tcaccggtag   9240
cgctcgattg ggcagtctgg gcaaccgcag tttcatggat atgccttca gcaccagcgg   9300 atatactgca aaagtcatag aggataaggg agcatcaacg gttggtgatg tgatggagag   9360
cgatgcatcg gtgcgcaata cgcatccgtc tggcggcatt gtcgactctt tctatatccg   9420
tggctttccc atcggtgacg gcaattttgg tgaaattgcg tttgatggca tgttcggcgt   9480
cgcaccaaac tatcgcgttt ttaccgatta tgcggaatcc gtagaagtcc tgaaagggcc   9540
aacctccttc ctctatggca tttctcccaa tggtggtgtg ggcggaacca tcaatattgt   9600
tccaaagcgt gctctggata cggacctgac ccgtgtcacc accagctatg aatcggatct   9660
tcaggttgga acgcatgtgg atatcagccg ccgctatggc agtgaacggc aatttggcgt   9720
ccggctgaat ggcagcgttc aaggtggtga tggcactatc gacgatcttt ctcgttttgc   9780
ctatgtcggt gcggttgcgc tggactacga aggagaaaat ctgcgcgcaa cgctcgatgt   9840
catcaatcaa tatgaacatt atgacgcgcc acagcgtcca ttctatccca cagccggcat   9900
taaactgccg agtgcaccgg acaatcgtct gaatgtgcag gagtcctggg aatggtcagc   9960
aacccgggag ttttcaacac tggggcgcgt tgaatatgac ctcagcgatg acgtgaccgt  10020
gtttggtgcc gtcggtggtg ggaagtcaaa cgtcgagcgt ctgtttggca cgcccacaat  10080
cacggactct gccggcaatg tcagcatcgt accgcagcat tatattttg atgtgcagag  10140 acgaaccgca gaaatcggca ctcgcggaca gttcgacacc ggcatcatcg agcactccgt  10200
gacattgcag gccaattata tgctgcaatg gctgtcgcga ggctccaatt ccggtacggc  10260
ccaaaccacc aatctgtata tccggttga tcgtgaggag caatttgttg ccaagccgtc  10320
cagcgtaccg aaagtaacgg aaagcgaatt ctacggtgtg gctttatccg atacaatgtc  10380
catatgggat gagcgggcgc aattgatggt tggcgggcgc tttcaacaca tcgattccga  10440
aaactacagc tcgacaactg gcgctgtaac atcctcttcc gacgcgagcg caataacacc  10500
catggttggt gtcgtggtta agccgtggga aaatgtatcg ctatatgcaa actatgcgga  10560
agggttgagc atcggggaaa cggctccgac aaacgccgta aacgcaggcg aaaccctcag  10620
cccctataaa tccaagcaat atgaagtggg aaccaagata gacaccggtc cggtgacgct  10680
```

```
caccgccagt cttttccaga tcgaaaagcc gtttggtgtt ttggagacgc gtggcagcga    10740
tctggttttc gaacgcggtg gcgaacagcg taaccgggt cttgaactt cagcgttcgg      10800 cgagttgacc gacaccgtga gactgcttgg cggcgttacg ttcatgcggg gcgagttgac    10860
gaaaaccaac aatgcctcga cgcaaggcaa tgaccccatt ggcgtgccaa aagtcctcgt    10920
aaacctcggt gcagaatggg acaccccatt cctgagcggc ttcaccctga cgggcaacgt    10980
catccacacc ggcaaacaat atgccgatac agccaatatc caaaaactac cggcatggac    11040
acgtcttgat ctcggcgcgc gctacaagac aacgatcaag gagcgacccg ttaccttccg    11100
tgccgaagtc gaaaacgtct tcaacaagaa ttactggtca ggtgtcgcaa gctttggcac    11160
tgtgacacaa ggggccccgt tgaccgttaa aatatcgatg acaaccgatt tttaagtctc    11220
gttaaccact gatgtatcgt ttgcgagtca gcgccttcg aagaggcgtt gtcttcgtct     11280
atggggcttg actgtcgatt ccacttgggg ccggcactgt aaacttaccg ccttgaacgc    11340
aacatctggg cgtgaggaat tagttcatgc ggcgtgaagg cgcgcgattt ggtgccatgc    11400
ttgcatggca gctgttcgca gttcgcgatg gtggacggat ggaatatcgt ggcggggaat    11460
gtgaaaaagg ttggtgatcg ggtcatggat ggaaacgaaa cgctgaagat gtcgtgttga    11520
cttgaagcgc ttcatgatcc tctcccgtcg tcggacgggc tgatgagagt tttccgaccg    11580
atttttcaat cctttgtgag aacgatgctc aatgccgggc atgacctccc gctttgctgc    11640
accataggat cgtagtttgt cggtaatcat cacacgcagc gcacggcctt gggctttcag    11700
gagcttgcgc atcaaacgtt ttgccgcctt ggtattgctg cggttttgca ccagcacatc    11760
gagaacaaag ccatcctgat caacggcgcg ccaaagccag tgtttccttc caccgatggt    11820
gatgacaacc tcatcgagat gccatttgtc cccgagcctg ccggtagatc gcttgcggat    11880
atcgttggca aaatgtcta                                                 11899
```

<210> SEQ ID NO 16
<211> LENGTH: 471
<212> TYPE: DNA
<213> ORGANISM: A. vitis strain F2/5
<220> FEATURE:
<221> NAME/KEY: gene
<222> LOCATION: (1)..(471)
<223> OTHER INFORMATION: P1388

<400> SEQUENCE: 16

```
ttgtacgata gagcagtggg catgaacatt tcttcgtcta ccttcgcctc ctatcgttac     60
aaacgtcacc gctttccagc cgagattatc gctcacgcgg tttggctgta cttccggttt   120
ccattgagcc tgcggcatgt cgaggatttg ctggccgaac gcggtattga cgtttcgttc    180
cagacagtat cggaatgggc cgccaaattt ggctccgagt ttgctgcgtt gcttcgccgg    240
cgctcaaagg gcggctttgc cgataaatgg cacctcgatg agatggtggt aaccatcaaa    300
ggccggaaat acggctctgt cgcaaagatt ccgtttgtgc tggaaataag ggagatagtt    360
ttcagcgaga cttttgatga gcgatttcaa gtggcgtcat tttcagggcg aggtgatctt    420
gtgggcagtt cgctggtatt gccgctatgg ggtgagctac cgcgatcttg a             471
```

<210> SEQ ID NO 17
<211> LENGTH: 156
<212> TYPE: PRT
<213> ORGANISM: A. vitis strain F2/5

<400> SEQUENCE: 17

Met Tyr Asp Arg Ala Val Gly Met Asn Ile Ser Ser Ser Thr Phe Ala

```
1               5                    10                   15
Ser Tyr Arg Tyr Lys Arg His Arg Phe Pro Ala Glu Ile Ile Ala His
                20                  25                  30
Ala Val Trp Leu Tyr Phe Arg Phe Pro Leu Ser Leu Arg His Val Glu
            35                  40                  45
Asp Leu Leu Ala Glu Arg Gly Ile Asp Val Ser Phe Gln Thr Val Ser
        50                  55                  60
Glu Trp Ala Ala Lys Phe Gly Ser Glu Phe Ala Ala Leu Leu Arg Arg
65                  70                  75                  80
Arg Ser Lys Gly Gly Phe Ala Asp Lys Trp His Leu Asp Glu Met Val
                85                  90                  95
Val Thr Ile Lys Gly Arg Lys Tyr Gly Ser Val Ala Lys Ile Pro Phe
                100                 105                 110
Val Leu Glu Ile Arg Glu Ile Val Phe Ser Glu Thr Phe Asp Glu Arg
            115                 120                 125
Phe Gln Val Ala Ser Phe Ser Gly Arg Gly Asp Leu Val Gly Ser Ser
        130                 135                 140
Leu Val Leu Pro Leu Trp Gly Glu Leu Pro Arg Ser
145                 150                 155
```

<210> SEQ ID NO 18
<211> LENGTH: 1173
<212> TYPE: DNA
<213> ORGANISM: A. vitis strain F2/5
<220> FEATURE:
<221> NAME/KEY: gene
<222> LOCATION: (1)..(1173)
<223> OTHER INFORMATION: P1389

<400> SEQUENCE: 18

| | | | |
|---|---|---|---|
| gtgataaaac cagccaccac tctctttgcg gctctgctgt cgtgtcttgt cgcgcagatg | 60 |
| ccatctgctg tggcacagga gccagcggct caaacatcca atgcagcaac aacgccgcat | 120 |
| cgcatcaccg tgacagacat tgctggtcgg caggtgtcat tgcctgttcc tgtccatcgc | 180 |
| atgttgttgg gcgaagggcg gcagctctat cttgtcgcgt cattggagtc cgagaatcct | 240 |
| ctggcgtttc tggcaggatg gaaaaatgac ctcattgaag ccgaccccgc aacctatgcc | 300 |
| caatatgtcg cgaagtttcc gaaactgggc caactgccaa cctttggcgg caaggaagca | 360 |
| ggtctgattg atcttgagtc tgccattgtt caaaagcctg atgttgtgct tttgaatctc | 420 |
| gaaacccagc gtgccagcaa agagtccgaa tatatcgaaa agctggcatc actgggaata | 480 |
| ccggttcttt atatcgattt ccggcatcaa ccccttcaca ataccgaacc aacaatccgc | 540 |
| cttttgggcg agatcatggg acgtgaaaag cgcgccgagg aaattattgc cttcaggaaa | 600 |
| aaggcattgt cgcaagtgac ggatgtgatt gaacaaaaaa agcccgcacg accgaatgtc | 660 |
| tttgtcgagc ggattggcgg ttatgcggat gattgctgcc tcacctttgg caatgagaat | 720 |
| tttggtcgct atgtcgaaat cgccggcggg cacaatatcg gcgttgattt cttcccggga | 780 |
| accttcggac aattgaaccc ggaacaggtg attgctgccg acccggatca ggttgtggtc | 840 |
| acgagcgcca attgggaagc ttatgttccg ggtggacact ggatacccct ggggccgggt | 900 |
| gccaacagac aggaagccga acgaaaactg gaatggttca cgacaagaaa tgcctatatt | 960 |
| ggcaccaaag cggtcaaaaa ccgcagtttc catggcatat ggcatcagtt ctacaatagc | 1020 |
| ccttatgaat tcatcgccat acaacaaatc gcaaaatggc ttcatccgga tttgttcgcc | 1080 |
| gatctcgatc cagacgagac attcagggaa tatcatcgcc ttttctgcc aatcgaatac | 1140 | aagtcaggct atagtataag ccttgcgccc tga    1173

<210> SEQ ID NO 19
<211> LENGTH: 390
<212> TYPE: PRT
<213> ORGANISM: A. vitis strain F2/5

<400> SEQUENCE: 19

Met Ile Lys Pro Ala Thr Thr Leu Phe Ala Ala Leu Leu Ser Cys Leu
1               5                   10                  15

Val Ala Gln Met Pro Ser Ala Val Ala Gln Glu Pro Ala Ala Gln Thr
            20                  25                  30

Ser Asn Ala Ala Thr Thr Pro His Arg Ile Thr Val Thr Asp Ile Ala
        35                  40                  45

Gly Arg Gln Val Ser Leu Pro Val Pro Val His Arg Met Leu Leu Gly
    50                  55                  60

Glu Gly Arg Gln Leu Tyr Leu Val Ala Ser Leu Glu Ser Glu Asn Pro
65                  70                  75                  80

Leu Ala Phe Leu Ala Gly Trp Lys Asn Asp Leu Ile Glu Ala Asp Pro
                85                  90                  95

Ala Thr Tyr Ala Gln Tyr Val Ala Lys Phe Pro Lys Leu Ala Gln Leu
            100                 105                 110

Pro Thr Phe Gly Gly Lys Glu Ala Gly Leu Ile Asp Leu Glu Ser Ala
        115                 120                 125

Ile Val Gln Lys Pro Asp Val Val Leu Leu Asn Leu Glu Thr Gln Arg
    130                 135                 140

Ala Ser Lys Glu Ser Glu Tyr Ile Glu Lys Leu Ala Ser Leu Gly Ile
145                 150                 155                 160

Pro Val Leu Tyr Ile Asp Phe Arg His Gln Pro Leu His Asn Thr Glu
                165                 170                 175

Pro Thr Ile Arg Leu Leu Gly Glu Ile Met Gly Arg Glu Lys Arg Ala
            180                 185                 190

Glu Glu Ile Ile Ala Phe Arg Lys Lys Ala Leu Ser Gln Val Thr Asp
        195                 200                 205

Val Ile Glu Gln Lys Lys Pro Ala Arg Pro Asn Val Phe Val Glu Arg
    210                 215                 220

Ile Gly Gly Tyr Ala Asp Asp Cys Cys Leu Thr Phe Gly Asn Glu Asn
225                 230                 235                 240

Phe Gly Arg Tyr Val Glu Ile Ala Gly His Asn Ile Gly Gly Asp
                245                 250                 255

Phe Leu Pro Gly Thr Phe Gly Gln Leu Asn Pro Glu Gln Val Ile Ala
            260                 265                 270

Ala Asp Pro Asp Gln Val Val Val Thr Ser Ala Asn Trp Glu Ala Tyr
        275                 280                 285

Val Pro Gly Gly His Trp Ile Pro Leu Gly Pro Gly Ala Asn Arg Gln
    290                 295                 300

Glu Ala Glu Arg Lys Leu Glu Trp Phe Thr Thr Arg Asn Ala Tyr Ile
305                 310                 315                 320

Gly Thr Lys Ala Val Lys Asn Arg Ser Phe His Gly Ile Trp His Gln
                325                 330                 335

Phe Tyr Asn Ser Pro Tyr Glu Phe Ile Ala Ile Gln Gln Ile Ala Lys
            340                 345                 350

Trp Leu His Pro Asp Leu Phe Ala Asp Leu Asp Pro Asp Glu Thr Phe
        355                 360                 365

Arg Glu Tyr His Arg Leu Phe Leu Pro Ile Glu Tyr Lys Ser Gly Tyr
    370                 375                 380

Ser Ile Ser Leu Ala Pro
385                 390

<210> SEQ ID NO 20
<211> LENGTH: 1206
<212> TYPE: DNA
<213> ORGANISM: A. vitis strain F2/5
<220> FEATURE:
<221> NAME/KEY: gene
<222> LOCATION: (1)..(1206)
<223> OTHER INFORMATION: P1390

<400> SEQUENCE: 20

| | | | | | |
|---|---|---|---|---|---|
| atgctcaggg | caagcacgcc | tgtgtttctg | ctgctgtttg | cgctccagtt | catttccatg | 60 |
| ggagccatgg | aaatgagcgg | tcctttctgg | ccgctgcaga | tcagggtact | cagcccgtcg | 120 |
| gatacggcgt | tcggattggc | aagtatcggg | gtttatattt | gccccatgct | tggcatttcc | 180 |
| ctcaccagcg | cattctgggg | gcgtatgggt | gaccgctatg | caatcgctt | gatgatggtt | 240 |
| cgggccttgg | cggggttggc | gatcacccag | cttctgattg | cgcttgccca | agatgtctgg | 300 |
| gtcatcctgt | ttctgcggtt | cttacagggg | gctttcgccg | gctatattgc | gcccgcgcaa | 360 |
| gcctatgccg | tgcaggtcaa | tagcgggcgt | gatcgcgcca | gtctgttcgc | tggttgcag | 420 |
| gtggcgacca | atgtcggttc | gctgggcggc | gcatttgcgg | gtggtctcat | tctggatgca | 480 |
| atgccattcg | cggccgttaa | tatcacggcc | ggggccgtat | gtggtctatg | tgcccttgtt | 540 |
| gcctgggcaa | cattgcccat | cccgcccatc | agacagaatg | caccgcgctc | cgcttcaagc | 600 |
| gcgctcaccc | cgggccatcc | agaaagttct | gcaccagtcg | tcgggttgct | ggttttgatt | 660 |
| tgcgtattgt | tggccagccg | aatggtgctg | caagtgccgt | tttcgctcta | catgacccaa | 720 |
| gctttcggag | ccaaccactg | gattattggc | ctcagctacg | ggctcatggc | gtttggtttt | 780 |
| gtgattggcg | cccccctctg | ggcgcgtctg | ttcaaaatgc | gcagccttgg | ctttgtgttg | 840 |
| gcggcaaaca | ccgcgatcgc | tctggcctgc | gcaagcatcg | ctttgatagc | gggctacaca | 900 |
| accctcgttc | ccgttttgc | aggattatac | tttgtctggg | gcattctgct | tggtggtacg | 960 |
| acaccggttc | ttacctcgcg | tctttcccag | tccacagcct | tcaatcggca | aggtgaaatt | 1020 |
| ttgggccgtg | cgcaaagctg | gcagcaaatc | gcttccattc | tgggtatagc | agccggtgtt | 1080 |
| gggtccatgc | agctttgggg | tgctgatacc | gcattttccc | tggtatcggc | gtgttacatc | 1140 |
| ctgtcatttt | ttatcggcct | gtcgctcttg | ctcaaaagcg | gccccttacc | caaccgcata | 1200 |
| ggataa | | | | | | 1206 |

<210> SEQ ID NO 21
<211> LENGTH: 401
<212> TYPE: PRT
<213> ORGANISM: A. vitis strain F2/5

<400> SEQUENCE: 21

Met Leu Arg Ala Ser Thr Pro Val Phe Leu Leu Phe Ala Leu Gln
1               5                   10                  15

Phe Ile Ser Met Gly Ala Met Glu Met Ser Gly Pro Phe Trp Pro Leu
            20                  25                  30

Gln Ile Arg Val Leu Ser Pro Ser Asp Thr Ala Phe Gly Leu Ala Ser
        35                  40                  45

Ile Gly Val Tyr Ile Cys Pro Met Leu Gly Ile Ser Leu Thr Ser Ala
    50                  55                  60

Phe Trp Gly Arg Met Gly Asp Arg Tyr Gly Asn Arg Leu Met Met Val
65                  70                  75                  80

Arg Ala Leu Ala Gly Leu Ala Ile Thr Gln Leu Leu Ile Ala Leu Ala
            85                  90                  95

Gln Asp Val Trp Val Ile Leu Phe Leu Arg Phe Leu Gln Gly Ala Phe
        100                 105                 110

Ala Gly Tyr Ile Ala Pro Ala Gln Ala Tyr Ala Val Gln Val Asn Ser
    115                 120                 125

Gly Arg Asp Arg Ala Ser Leu Phe Ala Trp Leu Gln Val Ala Thr Asn
130                 135                 140

Val Gly Ser Leu Gly Ala Phe Ala Gly Leu Ile Leu Asp Ala
145                 150                 155                 160

Met Pro Phe Ala Ala Val Asn Ile Thr Ala Gly Ala Val Cys Gly Leu
                165                 170                 175

Cys Ala Leu Val Ala Trp Ala Thr Leu Pro Ile Pro Pro Ile Arg Gln
            180                 185                 190

Asn Ala Pro Arg Ser Ala Ser Ser Ala Leu Thr Pro Gly His Pro Glu
        195                 200                 205

Ser Ser Ala Pro Val Val Gly Leu Leu Val Leu Ile Cys Val Leu Leu
    210                 215                 220

Ala Ser Arg Met Val Leu Gln Val Pro Phe Ser Leu Tyr Met Thr Gln
225                 230                 235                 240

Ala Phe Gly Ala Asn His Trp Ile Ile Gly Leu Ser Tyr Gly Leu Met
                245                 250                 255

Ala Phe Gly Phe Val Ile Gly Ala Pro Leu Trp Ala Arg Leu Phe Lys
            260                 265                 270

Met Arg Ser Leu Gly Phe Val Leu Ala Ala Asn Thr Ala Ile Ala Leu
        275                 280                 285

Ala Cys Ala Ser Ile Ala Leu Ile Ala Gly Tyr Thr Thr Leu Val Pro
    290                 295                 300

Val Phe Ala Gly Leu Tyr Phe Val Trp Gly Ile Leu Leu Gly Gly Thr
305                 310                 315                 320

Thr Pro Val Leu Thr Ser Arg Leu Ser Gln Ser Thr Ala Phe Asn Arg
                325                 330                 335

Gln Gly Glu Ile Leu Gly Arg Ala Gln Ser Trp Gln Ile Ala Ser
            340                 345                 350

Ile Leu Gly Ile Ala Ala Gly Val Gly Ser Met Gln Leu Trp Gly Ala
        355                 360                 365

Asp Thr Ala Phe Ser Leu Val Ser Ala Cys Tyr Ile Leu Ser Phe Phe
    370                 375                 380

Ile Gly Leu Ser Leu Leu Leu Lys Ser Gly Pro Leu Pro Asn Arg Ile
385                 390                 395                 400

Gly

<210> SEQ ID NO 22
<211> LENGTH: 1893
<212> TYPE: DNA
<213> ORGANISM: A. vitis strain F2/5
<220> FEATURE:
<221> NAME/KEY: gene
<222> LOCATION: (1)..(1893)
<223> OTHER INFORMATION: P1391

<400> SEQUENCE: 22
atgacccatt tgctttcgcc tttgtttgac atccatgcgc agaccgatga ccagccgttg     60

-continued

```
cgggattttg ccgttgccaa tgcaatcagt cgccttgttc gctgcctgtt tgcagaacgt      120
cttctggctc ctgaagcgtt gctctggtcg cgtgacaagc atcaagcctg gttgccgctg      180
tggaacacgc gccgtgtgct gcatttttaaa catttgcatg cggcacccgc tggcaccttg     240
caaaaccgtg gcgagattga aattctcgac gccgacggcg ccatgcccg gattgaccat       300 cccgatgctt tgctgcggga agtgttcgct tcgttgtcca tctctccggc ccctgatggg      360
cttgaggttt tgatgcgcga tatcgccgac agcatcaaca atgatatgct ggcccgccga      420
caccggcagg tctgggctgc gagcctgaat gagaagatca acaatccgg tgcggtggat       480 tttctgggct atctctacgg tcatttgcct gcacatctgg cggcaatgct gattgaccag      540
tggggtgcgc tcgaaggtca tccgttttat ccgacatgga aggcaaaacc gagtttgcag      600
cccgaagagg ttgttgccct ttcgcctgaa ttcggggcca aggtgccggt ccggattgcg      660
gccttgcgtc ggggttgggc ctatgtggaa aaaatgccac atgtgactga ttacaatgac      720
tggttttctg cccagtttcc cgaattgttt gccgcgtgga agaccatct gagcgcacag       780 ggcaaatcag cgcaagactg gattcctttg cccatccacg gatggcacct cgagcatttt     840
gtccgccgcg aatttggaca ggaaatcgcc tctggcatct tgctgttgga cgggccagac      900
attgacacct cgccatccat gtcatttcgg accatgttac cggacgatga aacgttgcgc     960
cctttcatca gttgccggt tgccatctgg ctcaccagcg agcagcgcag cttgcaggcc      1020
aaatccattc acatggggcc tcggctttcc acgttgatca ccgatattct ggccaatgaa     1080
ccggacatgg ccgcacaatt ggaaatcttc accgaagaat tgggagccat tctgcacgat     1140
cccgataccg gcgatgagca tcgcgggcga ttttttgtcgg tggtctatcg caacgcccag     1200
cctttaaagc gcgaggatgg acgctatgcg gtgacggtcg ccgcacttct aagtgcaagt     1260
cccaaggatg gacgaccatt gatctgcgag ctgattgccc gttacggcaa tgaggaacag     1320
gcaagcgttg tcggcttttt ccgccggtat gttgaggtgg tggttcggcc tgcgttggcg     1380
atgtatcttc tttatggcat cgcttttgag gcccatcagc aaaacaccac catcgtgttt     1440
gatccttccg gttctgcgga aaagctgatc attcgggatt ttggtgatgg ccgcagcttt     1500
gcgcctctgc tcaaacagcg tggctatcac ctcaaaccct tcagcgtgc tgggattttg     1560 ccaccacct tgacgatga cattgggctg gttcgctcgt ttttgatcga cgcctgcttt     1620
atatgccatc tgcatgaaat tgctctgtgc ctgacccagc actatagtat cggcaatgat     1680
aggctctgga cagtgatcaa agaggtaacg caagaggcgt tgaaacatt gcggcctcgt     1740 gtgtcttcga cacgttctg gcaagaagaa cgagatgccc tgcttgaaaa aaatggcccc     1800
acccggtcgg ttctcaccat gcatctccag cgatatagcg actatcgggt ggagcatgag     1860
ctgcccaatc ctctggttgg ccgtgaatgc tga                                   1893
```

<210> SEQ ID NO 23
<211> LENGTH: 630
<212> TYPE: PRT
<213> ORGANISM: A. vitis strain F2/5

<400> SEQUENCE: 23

```
Met Thr His Leu Leu Ser Pro Leu Phe Asp Ile His Ala Gln Thr Asp
1               5                   10                  15

Asp Gln Pro Leu Arg Asp Phe Ala Val Ala Asn Ala Ile Ser Arg Leu
            20                  25                  30

Val Arg Cys Leu Phe Ala Glu Arg Leu Leu Ala Pro Glu Ala Leu Leu
        35                  40                  45
```

Trp Ser Arg Asp Lys His Gln Ala Trp Leu Pro Leu Trp Asn Thr Arg
 50                  55                  60

Arg Val Leu His Phe Lys His Leu His Ala Ala Pro Ala Gly Thr Leu
 65                  70                  75                  80

Gln Asn Arg Gly Glu Ile Glu Ile Leu Asp Ala Asp Gly Gly His Ala
                 85                  90                  95

Arg Ile Asp His Pro Asp Ala Leu Leu Arg Glu Val Phe Ala Ser Leu
             100                 105                 110

Ser Ile Ser Pro Ala Pro Asp Gly Leu Glu Val Leu Met Arg Asp Ile
         115                 120                 125

Ala Asp Ser Ile Asn Asn Asp Met Leu Ala Arg Arg His Arg Gln Val
 130                 135                 140

Trp Ala Ala Ser Leu Asn Glu Lys Ile Lys Gln Ser Gly Ala Val Asp
145                 150                 155                 160

Phe Leu Gly Tyr Leu Tyr Gly His Leu Pro Ala His Leu Ala Ala Met
                 165                 170                 175

Leu Ile Asp Gln Trp Gly Ala Leu Glu Gly His Pro Phe Tyr Pro Thr
             180                 185                 190

Trp Lys Ala Lys Pro Ser Leu Gln Pro Glu Glu Val Val Ala Leu Ser
         195                 200                 205

Pro Glu Phe Gly Ala Lys Val Pro Val Arg Ile Ala Ala Leu Arg Arg
 210                 215                 220

Gly Trp Ala Tyr Val Glu Lys Met Pro His Val Thr Asp Tyr Asn Asp
225                 230                 235                 240

Trp Phe Ser Ala Gln Phe Pro Glu Leu Phe Ala Ala Trp Lys Asp His
                 245                 250                 255

Leu Ser Ala Gln Gly Lys Ser Ala Gln Asp Trp Ile Pro Leu Pro Ile
             260                 265                 270

His Gly Trp His Leu Glu His Phe Val Arg Arg Glu Phe Gly Gln Glu
         275                 280                 285

Ile Ala Ser Gly Ile Leu Leu Leu Asp Gly Pro Asp Ile Asp Thr Ser
 290                 295                 300

Pro Ser Met Ser Phe Arg Thr Met Leu Pro Asp Asp Glu Thr Leu Arg
305                 310                 315                 320

Pro Phe Ile Lys Leu Pro Val Ala Ile Trp Leu Thr Ser Glu Gln Arg
                 325                 330                 335

Ser Leu Gln Ala Lys Ser Ile His Met Gly Pro Arg Leu Ser Thr Leu
             340                 345                 350

Ile Thr Asp Ile Leu Ala Asn Glu Pro Asp Met Ala Ala Gln Leu Glu
         355                 360                 365

Ile Phe Thr Glu Glu Leu Gly Ala Ile Leu His Asp Pro Asp Thr Gly
 370                 375                 380

Asp Glu His Arg Gly Arg Phe Leu Ser Val Val Tyr Arg Asn Ala Gln
385                 390                 395                 400

Pro Leu Lys Arg Glu Asp Gly Arg Tyr Ala Val Thr Val Ala Ala Leu
                 405                 410                 415

Leu Ser Ala Ser Pro Lys Asp Gly Arg Pro Leu Ile Cys Glu Leu Ile
             420                 425                 430

Ala Arg Tyr Gly Asn Glu Glu Gln Ala Ser Val Val Gly Phe Phe Arg
         435                 440                 445

Arg Tyr Val Glu Val Val Val Arg Pro Ala Leu Ala Met Tyr Leu Leu
 450                 455                 460

```
Tyr Gly Ile Ala Phe Glu Ala His Gln Gln Asn Thr Thr Ile Val Phe
465                 470                 475                 480

Asp Pro Ser Gly Ser Ala Glu Lys Leu Ile Ile Arg Asp Phe Gly Asp
                485                 490                 495

Gly Arg Ser Phe Ala Pro Leu Leu Lys Gln Arg Gly Tyr His Leu Lys
            500                 505                 510

Pro Phe Gln Arg Ala Gly Ile Leu Pro Thr Thr Phe Asp Asp Asp Ile
        515                 520                 525

Gly Leu Val Arg Ser Phe Leu Ile Asp Ala Cys Phe Ile Cys His Leu
    530                 535                 540

His Glu Ile Ala Leu Cys Leu Thr Gln His Tyr Ser Ile Gly Asn Asp
545                 550                 555                 560

Arg Leu Trp Thr Val Ile Lys Glu Val Thr Gln Glu Ala Phe Glu Thr
                565                 570                 575

Leu Arg Pro Arg Val Ser Ser Asp Thr Phe Trp Gln Glu Arg Asp
            580                 585                 590

Ala Leu Leu Glu Lys Lys Trp Pro Thr Arg Ser Val Leu Thr Met His
        595                 600                 605

Leu Gln Arg Tyr Ser Asp Tyr Arg Val Glu His Glu Leu Pro Asn Pro
    610                 615                 620

Leu Val Gly Arg Glu Cys
625                 630

<210> SEQ ID NO 24
<211> LENGTH: 1137
<212> TYPE: DNA
<213> ORGANISM: A. vitis strain F2/5
<220> FEATURE:
<221> NAME/KEY: gene
<222> LOCATION: (1)..(1137)
<223> OTHER INFORMATION: P1392

<400> SEQUENCE: 24
atgagggtcg ccatttgcgg cgcaggccgc accgggcatt tgaatgccgt gcttttttaag      60 caaaatccgc aggtccatct ctccgttttg acggagaatg acactcttgc cgccaattgg     120
gctggaaatc ctgctccatg gcaggctttt ttgccggatg tcagggtat gtccgggcgt      180 cctgattacg ttggcaacaa ccccgataaa gcggttggga acgctgatct gattgtcatt     240
acccagccag cccatgccag atccgctgtt ttgcagcgga tcgcaggcag tatctccagc     300
accaagcagg ttttcgtggg tgctattccg ggcttttgcg gttttgactg gctggctgcc     360
gatcacttag gcgcaaggga taatgtggtc atctggggtt tgaaggatgt gccgcatatc     420
gcctacgacc ttgttgccgg acagagcgtt cgcatgggcg gcgctaaagc ccatttgttt     480
gctggccttc atcggcggga atccgcccaa agtgccaagg ctctgcaaac aatgctgacc     540
gcactttaca atgcgcctgt aacccttttg caggactatc tggaaatcac cctgacaccc     600
ggcaatgcgc tgatgcatcc agcggtgctc tacggcctgc tggggccggg cgctccctgg     660
gagcgtaaac cgttctccga gccgctgtgc tggtggagtg attgccctga ggaaggcgcg     720
cgcttgctcg aaatgttcga tgccgaaaat caggccatat gtcaggcgat tgcgaccccga     780 accggtcttg atctcagctc cgtcaaacct ttgcggcagg aactgattga agcctatggc     840
gatcagattg ccgatagtca aacgatgtat tccctgctca gaacaaacag cgcctatgcg     900
ggaattcaat tgccgctgat ccccaatcat catggtcaag ctggttgat cgatctgcaa     960 agccgtgcct tcatgagga tgttgcatgc gggcaggcat tgctggtcaa gatcgcagag    1020
```

```
cggctggcgg taccgattcc aaccatctcg aaaacctaca cgtgggcgcg ccactatcat    1080
ggtgctttgc cggatggatt aagcccggtt cctgatgatt ggctggaggc tgcctga      1137
```

<210> SEQ ID NO 25
<211> LENGTH: 378
<212> TYPE: PRT
<213> ORGANISM: A. vitis strain F2/5

<400> SEQUENCE: 25

```
Met Arg Val Ala Ile Cys Gly Ala Gly Arg Thr Gly His Leu Asn Ala
1               5                   10                  15

Val Leu Phe Lys Gln Asn Pro Gln Val His Leu Ser Val Leu Thr Glu
            20                  25                  30

Asn Asp Thr Leu Ala Ala Asn Trp Ala Gly Asn Pro Ala Pro Trp Gln
        35                  40                  45

Ala Phe Leu Pro Asp Gly Gln Gly Met Ser Gly Arg Pro Asp Tyr Val
    50                  55                  60

Gly Asn Asn Pro Asp Lys Ala Val Gly Asn Ala Asp Leu Ile Val Ile
65                  70                  75                  80

Thr Gln Pro Ala His Ala Arg Ser Ala Val Leu Gln Arg Ile Ala Gly
                85                  90                  95

Ser Ile Ser Ser Thr Lys Gln Val Phe Val Gly Ala Ile Pro Gly Phe
            100                 105                 110

Cys Gly Phe Asp Trp Leu Ala Ala Asp His Leu Gly Ala Arg Asp Asn
        115                 120                 125

Val Val Ile Trp Gly Leu Lys Asp Val Pro His Ile Ala Tyr Asp Leu
130                 135                 140

Val Ala Gly Gln Ser Val Arg Met Gly Gly Ala Lys Ala His Leu Phe
145                 150                 155                 160

Ala Gly Leu His Arg Arg Glu Ser Ala Gln Ser Ala Lys Ala Leu Gln
                165                 170                 175

Thr Met Leu Thr Ala Leu Tyr Asn Ala Pro Val Thr Leu Leu Gln Asp
            180                 185                 190

Tyr Leu Glu Ile Thr Leu Thr Pro Gly Asn Ala Leu Met His Pro Ala
        195                 200                 205

Val Leu Tyr Gly Leu Leu Gly Pro Gly Ala Pro Trp Glu Arg Lys Pro
    210                 215                 220

Phe Ser Glu Pro Leu Cys Trp Trp Ser Asp Cys Pro Glu Glu Gly Ala
225                 230                 235                 240

Arg Leu Leu Glu Met Phe Asp Ala Glu Asn Gln Ala Ile Cys Gln Ala
                245                 250                 255

Ile Ala Thr Arg Thr Gly Leu Asp Leu Ser Ser Val Lys Pro Leu Arg
            260                 265                 270

Gln Glu Leu Ile Glu Ala Tyr Gly Asp Gln Ile Ala Asp Ser Gln Thr
        275                 280                 285

Met Tyr Ser Leu Leu Arg Thr Asn Ser Ala Tyr Ala Gly Ile Gln Leu
    290                 295                 300

Pro Leu Ile Pro Asn His His Gly Gln Gly Trp Leu Ile Asp Leu Gln
305                 310                 315                 320

Ser Arg Ala Phe His Glu Asp Val Ala Cys Gly Gln Ala Leu Leu Val
                325                 330                 335

Lys Ile Ala Glu Arg Leu Ala Val Pro Ile Pro Thr Ile Ser Lys Thr
            340                 345                 350

Tyr Thr Trp Ala Arg His Tyr His Gly Ala Leu Pro Asp Gly Leu Ser
```

Pro Val Pro Asp Asp Trp Leu Glu Ala Ala
370                 375

<210> SEQ ID NO 26
<211> LENGTH: 1011
<212> TYPE: DNA
<213> ORGANISM: A. vitis strain F2/5
<220> FEATURE:
<221> NAME/KEY: gene
<222> LOCATION: (1)..(1011)
<223> OTHER INFORMATION: P1393

<400> SEQUENCE: 26

```
atgctctata caaccgtcac gcaattgatt ggccagaccc cctgatcgc gcttgatctg    60
gcaacaagca atgcaaaact tttgctcaaa atggagaaga acaatcctgg cggctcaatg   120
aaagaccgca tggcgcgcag catggtggtt gcggccttgg cggatgggcg cctgccgcgt   180
ggcggcacga tcgttgaatc ctcatcaggc aacacgggca caggtctggc tcttgcggcg   240
ctggagtttg gtcttcgctt tatcgcggtc gtggatcatc acgccgcgcc ggataaaatc   300
cggatgatgc gggccttggg tgccgaaatt cgctatgttg aaggcgacta tcgcgaagat   360
gaagtggccg tcgttgaaag gcagagactg gccgcccagc tcggcgcgca actgcctggt   420
gcactgttca tgaaccagtc cgacaatccc gccaatcctg acggctatgc cggatttgtg   480
gatgagttga tggcacaact gcctgatgga ttggatgcct tgttggttg cgtgggtacg   540
ggtgggtcga tgacgggcat atcccagcgc ctcaagcgcc tcaatcccgc catcaagaca   600
attgcggttg agcctgctgg ttccattgtt tttggtaagc cggggcattc ctattaccaa   660
tctggcacag gtacgcccgc aggcgatgaa gtcggcaagg ttctggatta tagctgcatt   720
gatgaaggtg ttcaggtcac cgatacgcaa gcatttgaaa cggcacgcta tattgcccga   780
cgcaaaggta ttctcgttgg tggatcaacc ggggtacaa tttacaaagc tctcgaattc   840
atcgcatccg gtaaattgag cggcacaatt gttacagccg tcgcagatgg gggtgaaaaa   900
tacctggcat ccgtgtttga cgatgagtgg atgaaaagc gcgggcttct caatccggca   960
atcgcagctc aattggatgg ttggttcaat ggcttggcag gtgcggcatg a            1011
```

<210> SEQ ID NO 27
<211> LENGTH: 336
<212> TYPE: PRT
<213> ORGANISM: A. vitis strain F2/5

<400> SEQUENCE: 27

Met Leu Tyr Thr Thr Val Thr Gln Leu Ile Gly Gln Thr Pro Leu Ile
1               5                   10                  15

Ala Leu Asp Leu Ala Thr Ser Asn Ala Lys Leu Leu Leu Lys Met Glu
            20                  25                  30

Lys Asn Asn Pro Gly Gly Ser Met Lys Asp Arg Met Ala Arg Ser Met
        35                  40                  45

Val Val Ala Ala Leu Ala Asp Gly Arg Leu Pro Arg Gly Gly Thr Ile
    50                  55                  60

Val Glu Ser Ser Ser Gly Asn Thr Gly Thr Gly Leu Ala Leu Ala Ala
65                  70                  75                  80

Leu Glu Phe Gly Leu Arg Phe Ile Ala Val Val Asp His His Ala Ala
                85                  90                  95

Pro Asp Lys Ile Arg Met Met Arg Ala Leu Gly Ala Glu Ile Arg Tyr
            100                 105                 110

```
Val Glu Gly Asp Tyr Arg Glu Asp Glu Val Ala Val Glu Arg Gln
        115                 120                 125

Arg Leu Ala Ala Gln Leu Gly Ala Gln Leu Pro Gly Ala Leu Phe Met
    130                 135                 140

Asn Gln Ser Asp Asn Pro Ala Asn Pro Asp Gly Tyr Ala Gly Phe Val
145                 150                 155                 160

Asp Glu Leu Met Ala Gln Leu Pro Asp Gly Leu Asp Ala Phe Val Gly
                165                 170                 175

Cys Val Gly Thr Gly Gly Ser Met Thr Gly Ile Ser Gln Arg Leu Lys
                180                 185                 190

Arg Leu Asn Pro Ala Ile Lys Thr Ile Ala Val Glu Pro Ala Gly Ser
                195                 200                 205

Ile Val Phe Gly Lys Pro Gly His Ser Tyr Tyr Gln Ser Gly Thr Gly
            210                 215                 220

Thr Pro Ala Gly Asp Glu Val Gly Lys Val Leu Asp Tyr Ser Cys Ile
225                 230                 235                 240

Asp Glu Gly Val Gln Val Thr Asp Thr Gln Ala Phe Glu Thr Ala Arg
                245                 250                 255

Tyr Ile Ala Arg Arg Lys Gly Ile Leu Val Gly Gly Ser Thr Gly Gly
            260                 265                 270

Thr Ile Tyr Lys Ala Leu Glu Phe Ile Ala Ser Gly Lys Leu Ser Gly
        275                 280                 285

Thr Ile Val Thr Ala Val Ala Asp Gly Gly Glu Lys Tyr Leu Ala Ser
    290                 295                 300

Val Phe Asp Asp Glu Trp Met Glu Lys Arg Gly Leu Leu Asn Pro Ala
305                 310                 315                 320

Ile Ala Ala Gln Leu Asp Gly Trp Phe Asn Gly Leu Ala Gly Ala Ala
                325                 330                 335
```

<210> SEQ ID NO 28
<211> LENGTH: 1398
<212> TYPE: DNA
<213> ORGANISM: A. vitis strain F2/5
<220> FEATURE:
<221> NAME/KEY: gene
<222> LOCATION: (1)..(1398)
<223> OTHER INFORMATION: P1394

<400> SEQUENCE: 28

```
atgagacttg gctccaagca atctcacact ctgacgcccc tgattcatga cgaggtcgca    60
gattttattg aaaacaagca tgaacagttg cgggaaggat tcaacagatt tggctcgccg   120
ctccatttga tctggcctga tctgctggcc gataatcttc tggctttgca ggccatattg   180
agcggcagtc aagttccatg cagaatttat tatggtgtga aggtcaacaa gtctgtgaat   240
cttatgggag ctgcccttca ggctgaagga ggcgttgatg tctccagcct gtacgagttg   300
caggatgcct ggcattgggt gcaaagggt gccgatattg ttgcgaccgg tcctgccaaa   360
acatcgacat tcatagagc gttgatggcc tgcaaggccc tgatttccat cgattccgtt   420
gaggaattcg atgatatttt gaaggaattg ccaagcgccg gtgaccctca gcccgtgctt   480
ttgagattaa ggccccaaaa tcaagggcaa agccgcttcg gcatggatgc tcaagacgtt   540
gtttcgtgcc tgcatcgttt ggcaggcacc ccagccctac gatttgatgg aatccatttc   600
cacttgagtg gttatagcgt taaggcgcgc atcgaagcat tgaatgaagc agcggatctc   660
attgccaaag cgcgcggcat ggggcttcct ccccgcatga tcgatattgg tggtgggttg   720
```

```
ccggtgcaat atgtcgatca cccgacctac gccgcctttc tggaggcgca aacggcgcag    780
gattatcgca ccaaccatct gccacagtct ttttatccct atggaggacc tgtttgcgca    840
acggagtggt taactcacct gttgcaatcc aaaatgcagg acgggcgcga tgtcgcaaca    900
tatttccgtc aggaaaatct tacgctgggg atggagccgg ggcgggccct tgcggatcag    960
actgcaatca cggctttcag agtgacgaga gtgaaggcac tgggtgcgca gtcagcagca   1020
atttttgtgg agggcagcag cttcagtgca tgcgaaacat ggttcgcatc agaatttctg   1080
atcgatccca ttgtggtgcc gcacgggccg gaagctgcac gcaccactcc tgtgcgcgcc   1140
tatcttgccg acatagctg ccttgatgaa gatattgtct ccaaccgctg gctcgacttt   1200
ccgattaccc cgcaagctgg tgatttgctc atctatgtca ataccggcgg ctatcagatg   1260
gatctgatgg aaaaccagtt tcaccgccac cccatgccaa tccgcttatg tgtcaggagg   1320
accgcagatg gactgtccga acttattccg gataacctgtg aggaggtact atgctctata   1380
caaccgtcac gcaattga                                                 1398
```

<210> SEQ ID NO 29
<211> LENGTH: 465
<212> TYPE: PRT
<213> ORGANISM: A. vitis strain F2/5

<400> SEQUENCE: 29

Met Arg Leu Gly Ser Lys Gln Ser His Thr Leu Thr Pro Leu Ile His
1               5                   10                  15

Asp Glu Val Ala Asp Phe Ile Glu Asn Lys His Glu Gln Leu Arg Glu
            20                  25                  30

Gly Phe Asn Arg Phe Gly Ser Pro Leu His Leu Ile Trp Pro Asp Leu
        35                  40                  45

Leu Ala Asp Asn Leu Leu Ala Leu Gln Ala Ile Leu Ser Gly Ser Gln
    50                  55                  60

Val Pro Cys Arg Ile Tyr Tyr Gly Val Lys Val Asn Lys Ser Val Asn
65                  70                  75                  80

Leu Met Gly Ala Ala Leu Gln Ala Glu Gly Gly Val Asp Val Ser Ser
                85                  90                  95

Leu Tyr Glu Leu Gln Asp Ala Leu Ala Leu Gly Ala Lys Gly Ala Asp
            100                 105                 110

Ile Val Ala Thr Gly Pro Ala Lys Thr Ser Thr Phe His Arg Ala Leu
        115                 120                 125

Met Ala Cys Lys Ala Leu Ile Ser Ile Asp Ser Val Glu Glu Phe Asp
    130                 135                 140

Asp Ile Leu Lys Glu Leu Pro Ser Ala Gly Asp Pro Gln Pro Val Leu
145                 150                 155                 160

Leu Arg Leu Arg Pro Gln Asn Gln Gly Gln Ser Arg Phe Gly Met Asp
                165                 170                 175

Ala Gln Asp Val Val Ser Cys Leu His Arg Leu Ala Gly Thr Pro Ala
            180                 185                 190

Leu Arg Phe Asp Gly Ile His Phe His Leu Ser Gly Tyr Ser Val Lys
        195                 200                 205

Ala Arg Ile Glu Ala Leu Asn Glu Ala Ala Asp Leu Ile Ala Lys Ala
    210                 215                 220

Arg Gly Met Gly Leu Ser Pro Arg Met Ile Asp Ile Gly Gly Gly Leu
225                 230                 235                 240

Pro Val Gln Tyr Val Asp His Pro Thr Tyr Ala Ala Phe Leu Glu Ala
                245                 250                 255

Gln Thr Ala Gln Asp Tyr Arg Thr Asn His Leu Pro Gln Ser Phe Tyr
            260                 265                 270

Pro Tyr Gly Gly Pro Val Cys Ala Thr Glu Trp Leu Thr His Leu Leu
        275                 280                 285

Gln Ser Lys Met Gln Asp Gly Arg Asp Val Ala Thr Tyr Phe Arg Gln
    290                 295                 300

Glu Asn Leu Thr Leu Gly Met Glu Pro Gly Arg Ala Leu Ala Asp Gln
305                 310                 315                 320

Thr Ala Ile Thr Ala Phe Arg Val Thr Arg Val Lys Ala Leu Gly Ala
                325                 330                 335

Gln Ser Ala Ala Ile Phe Val Glu Gly Ser Ser Phe Ser Ala Cys Glu
            340                 345                 350

Thr Trp Phe Ala Ser Glu Phe Leu Ile Asp Pro Ile Val Val Pro His
        355                 360                 365

Gly Pro Glu Ala Ala Arg Thr Thr Pro Val Arg Ala Tyr Leu Ala Gly
    370                 375                 380

His Ser Cys Leu Asp Glu Asp Ile Val Ser Asn Arg Trp Leu Asp Phe
385                 390                 395                 400

Pro Ile Thr Pro Gln Ala Gly Asp Leu Leu Ile Tyr Val Asn Thr Gly
                405                 410                 415

Gly Tyr Gln Met Asp Leu Met Glu Asn Gln Phe His Arg His Pro Met
            420                 425                 430

Pro Ile Arg Leu Cys Val Arg Arg Thr Ala Asp Gly Leu Ser Glu Leu
        435                 440                 445

Ile Pro Asp Thr Cys Glu Glu Val Leu Cys Ser Ile Gln Pro Ser Arg
    450                 455                 460

Asn
465

<210> SEQ ID NO 30
<211> LENGTH: 501
<212> TYPE: DNA
<213> ORGANISM: A. vitis strain F2/5
<220> FEATURE:
<221> NAME/KEY: gene
<222> LOCATION: (1)..(501)
<223> OTHER INFORMATION: P1395

<400> SEQUENCE: 30
atgttaaaca tgatttatgt agtcatattt tcggaaatag cgattttcac cgaagggctg      60
tattttatgc catatcattt tgcctctccc aaaaaacttg tcgacactga agaagtcgat     120
caaagcgttg ttgagaattt gcgccaaacc attttacgtc agcagatctg gacacgccct     180
attgcggtcg agcgcactca gtttctggtg atggatgggc atcaccggct tgaggtcgca     240
aggcagctca atctcgctgt cattcctgtt gtcctcctgg attatgagcg tgtgtctgtc     300
acgagttggc ggcctgagga atgcattaca ccagacgata ttttgccat ggcgcggtcc     360 ggcaaaaaat ttccgatcaa aacgacacgt cacgtcttcg cggatgatta ccctgtatgt     420
gatgtaccgc tcgcggtatt agccggaatt gtggctacca tggattcggc gatgcaaggc     480
ggcagggcgg tgctgtcatg a                                              501

<210> SEQ ID NO 31
<211> LENGTH: 166
<212> TYPE: PRT
<213> ORGANISM: A. vitis strain F2/5

<400> SEQUENCE: 31

```
Met Leu Asn Met Ile Tyr Val Val Ile Phe Ser Glu Ile Ala Ile Phe
1               5                   10                  15

Thr Glu Gly Leu Tyr Phe Met Pro Tyr His Phe Ala Ser Pro Lys Lys
            20                  25                  30

Leu Val Asp Thr Glu Val Asp Gln Ser Val Val Glu Asn Leu Arg
        35                  40                  45

Gln Thr Ile Leu Arg Gln Ile Trp Thr Arg Pro Ile Ala Val Glu
    50                  55                  60

Arg Thr Gln Phe Leu Val Met Asp Gly His His Arg Leu Glu Val Ala
65                  70                  75                  80

Arg Gln Leu Asn Leu Ala Val Ile Pro Val Val Leu Leu Asp Tyr Glu
                85                  90                  95

Arg Val Ser Val Thr Ser Trp Arg Pro Glu Glu Cys Ile Thr Pro Asp
            100                 105                 110

Asp Ile Phe Ala Met Ala Arg Ser Gly Lys Lys Phe Pro Ile Lys Thr
        115                 120                 125

Thr Arg His Val Phe Ala Asp Asp Tyr Pro Val Cys Asp Val Pro Leu
    130                 135                 140

Ala Val Leu Ala Gly Ile Val Ala Thr Met Asp Ser Ala Met Gln Gly
145                 150                 155                 160

Gly Arg Ala Val Leu Ser
                165
```

<210> SEQ ID NO 32
<211> LENGTH: 2154
<212> TYPE: DNA
<213> ORGANISM: A. vitis strain F2/5
<220> FEATURE:
<221> NAME/KEY: gene
<222> LOCATION: (1)..(2154)
<223> OTHER INFORMATION: P1396

<400> SEQUENCE: 32

```
atgatgggtt tgaaaagtgg cgttgccatg ggtgcaattc tggctgctct cggcactgtt      60
gcgcaggcag aagaggacac ggttctcaag ccaattgttg ttgagggaca atcctcatcg     120
cccaacgcaa ccataggcaa acagagcgaa ccttatgcag ggggcatggt caccggtagc     180
gctcgattgg gcagtctggg caaccgcagt ttcatggata tgccttttcag caccagcgga    240
tatactgcaa aagtcataga ggataaggga gcatcaacgg ttggtgatgt gatggagagc     300
gatgcatcgg tgcgcaatac gcatccgtct ggcggcattg tcgactcttt ctatatccgt     360
ggctttccca tcggtgacgg caattttggt gaaattgcgt ttgatggcat gttcggcgtc     420
gcaccaaact atcgcgtttt taccgattat gcggaatccg tagaagtcct gaaagggcca     480
acctccttcc tctatggcat ttctcccaat ggtggtgtgg gcggaaccat caatattgtt     540
ccaaagcgtg ctctggatac ggacctgacc cgtgtcacca ccagctatga atcggatctt     600
caggttggaa cgcatgtgga tatcagccgc cgctatggca gtgaacggca atttggcgtc     660
cggctgaatg gcagcgttca aggtggtgat ggcactatcg acgatctttc tcgttttgcc     720
tatgtcggtg cggttgcgct ggactacgaa ggagaaaatc tgcgcgcaac gctcgatgtc     780
atcaatcaat atgaacatta tgacgcgcca cagcgtccat tctatcccac agccggcatt     840
aaactgccga gtgcaccgga caatcgtctg aatgtgcagg agtcctggga atggtcagca     900
acccgggagt tttcaacact ggggcgcgtt gaatatgacc tcagcgatga cgtgaccgtg     960
```

-continued

```
tttggtgccg tcggtggtgg gaagtcaaac gtcgagcgtc tgtttggcac gcccacaatc    1020
acggactctg ccggcaatgt cagcatcgta ccgcagcatt atattttga tgtgcagaga     1080
cgaaccgcag aaatcggcac tcgcggacag ttcgacaccg gcatcatcga gcactccgtg    1140
acattgcagg ccaattatat gctgcaatgg ctgtcgcgag gctccaattc cggtacggcc    1200
caaaccacca atctgtataa tccggttgat cgtgaggagc aatttgttgc caagccgtcc    1260
agcgtaccga agtaacgga aagcgaattc tacggtgtgg ctttatccga tacaatgtcc     1320
atatgggatg agcgggcgca attgatggtt ggcgggcgct ttcaacacat cgattccgaa    1380
aactacagct cgacaactgg cgctgtaaca tcctcttccg acgcgagcgc aataacaccc    1440
atggttggtg tcgtggttaa gccgtgggaa aatgtatcgc tatatgcaaa ctatgcggaa    1500
gggttgagca tcggggaaac ggctccgaca acgccgtaa acgcaggcga acccctcagc     1560
ccctataaat ccaagcaata tgaagtggga accaagatag acaccggtcc ggtgacgctc    1620
accgccagtc ttttccagat cgaaaagccg tttggtgttt tggagacgcg tggcagcgat    1680
ctggttttcg aacgcggtgg cgaacagcgt aaccggggtc ttgaactttc agcgttcggc    1740
gagttgaccg acaccgtgag actgcttggc ggcgttacgt tcatgcgggg cgagttgacg    1800
aaaaccaaca atgcctcgac gcaaggcaat gaccccattg gcgtgccaaa agtcctcgta    1860
aacctcggtg cagaatggga cacccattc ctgagcggct tcaccctgac gggcaacgtc     1920
atccacaccg gcaaacaata tgccgataca gccaatatcc aaaaactacc ggcatggaca    1980
cgtcttgatc tcggcgcgcg ctacaagaca cgatcaagg agcgacccgt taccttccgt     2040
gccgaagtcg aaaacgtctt caacaagaat tactggtcag tgtcgcaag ctttggcact     2100
gtgacacaag gggccccgtt gaccgttaaa atatcgatga caaccgattt ttaa          2154
```

<210> SEQ ID NO 33
<211> LENGTH: 716
<212> TYPE: PRT
<213> ORGANISM: A. vitis strain F2/5

<400> SEQUENCE: 33

```
Met Met Gly Leu Lys Ser Gly Val Ala Met Gly Ala Ile Leu Ala Ala
1               5                   10                  15

Leu Gly Thr Val Ala Gln Ala Glu Glu Asp Thr Val Leu Lys Pro Ile
            20                  25                  30

Val Val Glu Gly Gln Ser Ser Pro Asn Ala Thr Ile Gly Lys Gln
        35                  40                  45

Ser Glu Pro Tyr Ala Gly Gly Met Val Thr Gly Ser Ala Arg Leu Gly
    50                  55                  60

Ser Leu Gly Asn Arg Ser Phe Met Asp Met Pro Phe Ser Thr Ser Gly
65                  70                  75                  80

Tyr Thr Ala Lys Val Ile Glu Asp Lys Gly Ala Ser Thr Val Gly Asp
                85                  90                  95

Val Met Glu Ser Asp Ala Ser Val Arg Asn Thr His Pro Ser Gly Gly
            100                 105                 110

Ile Val Asp Ser Phe Tyr Ile Arg Gly Phe Pro Ile Gly Asp Gly Asn
        115                 120                 125

Phe Gly Glu Ile Ala Phe Asp Gly Met Phe Gly Val Ala Pro Asn Tyr
    130                 135                 140

Arg Val Phe Thr Asp Tyr Ala Glu Ser Val Glu Val Leu Lys Gly Pro
145                 150                 155                 160

Thr Ser Phe Leu Tyr Gly Ile Ser Pro Asn Gly Gly Val Gly Gly Thr
```

```
                165                 170                 175
Ile Asn Ile Val Pro Lys Arg Ala Leu Asp Thr Asp Leu Thr Arg Val
                180                 185                 190

Thr Thr Ser Tyr Glu Ser Asp Leu Gln Val Gly Thr His Val Asp Ile
                195                 200                 205

Ser Arg Arg Tyr Gly Ser Glu Arg Gln Phe Gly Val Arg Leu Asn Gly
    210                 215                 220

Ser Val Gln Gly Gly Asp Gly Thr Ile Asp Asp Leu Ser Arg Phe Ala
225                 230                 235                 240

Tyr Val Gly Ala Val Ala Leu Asp Tyr Glu Gly Glu Asn Leu Arg Ala
                245                 250                 255

Thr Leu Asp Val Ile Asn Gln Tyr Glu His Tyr Asp Ala Pro Gln Arg
                260                 265                 270

Pro Phe Tyr Pro Thr Ala Gly Ile Lys Leu Pro Ser Ala Pro Asp Asn
            275                 280                 285

Arg Leu Asn Val Gln Glu Ser Trp Glu Trp Ser Ala Thr Arg Glu Phe
            290                 295                 300

Ser Thr Leu Gly Arg Val Glu Tyr Asp Leu Ser Asp Asp Val Thr Val
305                 310                 315                 320

Phe Gly Ala Val Gly Gly Lys Ser Asn Val Glu Arg Leu Phe Gly
                325                 330                 335

Thr Pro Thr Ile Thr Asp Ser Ala Gly Asn Val Ser Ile Val Pro Gln
                340                 345                 350

His Tyr Ile Phe Asp Val Gln Arg Arg Thr Ala Glu Ile Gly Thr Arg
                355                 360                 365

Gly Gln Phe Asp Thr Gly Ile Ile Glu His Ser Val Thr Leu Gln Ala
            370                 375                 380

Asn Tyr Met Gln Trp Leu Ser Arg Gly Ser Asn Ser Gly Thr Ala Gln
385                 390                 395                 400

Thr Thr Asn Leu Tyr Asn Pro Val Asp Arg Glu Glu Gln Phe Val Ala
                405                 410                 415

Lys Pro Ser Ser Val Pro Lys Val Thr Glu Ser Glu Phe Tyr Gly Val
                420                 425                 430

Ala Leu Ser Asp Thr Met Ser Ile Trp Asp Glu Arg Ala Gln Leu Met
            435                 440                 445

Val Gly Gly Arg Phe Gln His Ile Asp Ser Glu Asn Tyr Ser Ser Thr
            450                 455                 460

Thr Gly Ala Val Thr Ser Ser Asp Ala Ser Ala Ile Thr Pro Met
465                 470                 475                 480

Val Gly Val Val Lys Pro Trp Glu Asn Val Ser Leu Tyr Ala Asn
                485                 490                 495

Tyr Ala Glu Gly Leu Ser Ile Gly Glu Thr Ala Pro Thr Asn Ala Val
            500                 505                 510

Asn Ala Gly Glu Thr Leu Ser Pro Tyr Lys Ser Lys Gln Tyr Glu Val
            515                 520                 525

Gly Thr Lys Ile Asp Thr Gly Pro Val Thr Leu Thr Ala Ser Leu Phe
            530                 535                 540

Gln Ile Glu Lys Pro Phe Gly Val Leu Glu Thr Arg Gly Ser Asp Leu
545                 550                 555                 560

Val Phe Glu Arg Gly Gly Glu Gln Arg Asn Arg Gly Leu Glu Leu Ser
                565                 570                 575

Ala Phe Gly Glu Leu Thr Asp Thr Val Arg Leu Leu Gly Gly Val Thr
            580                 585                 590
```

```
Phe Met Arg Gly Glu Leu Thr Lys Thr Asn Asn Ala Ser Thr Gln Gly
        595                 600                 605

Asn Asp Pro Ile Gly Val Pro Lys Val Leu Val Asn Leu Gly Ala Glu
    610                 615                 620

Trp Asp Thr Pro Phe Leu Ser Gly Phe Thr Leu Thr Gly Asn Val Ile
625                 630                 635                 640

His Thr Gly Lys Gln Tyr Ala Asp Thr Ala Asn Ile Gln Lys Leu Pro
                645                 650                 655

Ala Trp Thr Arg Leu Asp Leu Gly Ala Arg Tyr Lys Thr Thr Ile Lys
            660                 665                 670

Glu Arg Pro Val Thr Phe Arg Ala Glu Val Glu Asn Val Phe Asn Lys
        675                 680                 685

Asn Tyr Trp Ser Gly Val Ala Ser Phe Gly Thr Val Thr Gln Gly Ala
    690                 695                 700

Pro Leu Thr Val Lys Ile Ser Met Thr Thr Asp Phe
705                 710                 715
```

<210> SEQ ID NO 34
<211> LENGTH: 717
<212> TYPE: DNA
<213> ORGANISM: A. vitis strain F2/5
<220> FEATURE:
<221> NAME/KEY: gene
<222> LOCATION: (1)..(717)
<223> OTHER INFORMATION: P1397

<400> SEQUENCE: 34

```
atgaccagat ccagccgtga tccccttat cgtcgccacc gatttcccgc cgaggtgatt      60
gcccatgcag tttggctgta tttccggttt ccgcttagcc tgcggatggt cgaggatctg    120
ctggcagcgc gtggcatcat cgtctctcat caaagcgtgc ggctctgggc ggagaaattc    180
ggtagacatt ttgccaacga tatccgcaag cgatctaccg gcaggctcgg ggacaaatgg    240
catctcgatg aggttgtcat caccatcggt ggaaggaaac actggctttg gcgcgccgtt    300
gatcaggatg gctttgttct cgatgtgctg gtgcaaaacc gcagcaatac caaggcggca    360
aaacgtttga tgcgcaagct cctgaaagcc caaggccgtg cgctgcgtgt gatgattacc    420
gacaaactac gatcctatgg tgcagcaaag cgggaggtca tgcccggcat tgagcatcgt    480
tctcacaaag gattgaaaaa tcggtcggaa aactctcatc agcccgtccg acgacgggag    540
aggatcatga agcgcttcaa gtcaacacga catcttcagc gtttcgtttc catccatgac    600
ccgatcacca acctttttca cattccccgc cacgatattc catccgtcca ccatcgcgaa    660
ctgcgaacag ctgccatgca agcatggcac caaatcgcgc gccttcacgc cgcatga       717
```

<210> SEQ ID NO 35
<211> LENGTH: 238
<212> TYPE: PRT
<213> ORGANISM: A. vitis strain F2/5

<400> SEQUENCE: 35

```
Met Thr Arg Ser Ser Arg Asp Pro Leu Tyr Arg Arg His Arg Phe Pro
1               5                   10                  15

Ala Glu Val Ile Ala His Ala Val Trp Leu Tyr Phe Arg Phe Pro Leu
                20                  25                  30

Ser Leu Arg Met Val Glu Asp Leu Leu Ala Ala Arg Gly Ile Ile Val
            35                  40                  45

Ser His Gln Ser Val Arg Leu Trp Ala Glu Lys Phe Gly Arg His Phe
```

```
              50                  55                  60
Ala Asn Asp Ile Arg Lys Arg Ser Thr Gly Arg Leu Gly Asp Lys Trp
 65                  70                  75                  80

His Leu Asp Glu Val Val Ile Thr Ile Gly Gly Arg Lys His Trp Leu
                 85                  90                  95

Trp Arg Ala Val Asp Gln Asp Gly Phe Val Leu Asp Val Leu Val Gln
            100                 105                 110

Asn Arg Ser Asn Thr Lys Ala Ala Lys Arg Leu Met Arg Lys Leu Leu
        115                 120                 125

Lys Ala Gln Gly Arg Ala Leu Arg Val Met Ile Thr Asp Lys Leu Arg
    130                 135                 140

Ser Tyr Gly Ala Ala Lys Arg Glu Val Met Pro Gly Ile Glu His Arg
145                 150                 155                 160

Ser His Lys Gly Leu Lys Asn Arg Ser Glu Asn Ser His Gln Pro Val
                165                 170                 175

Arg Arg Arg Glu Arg Ile Met Lys Arg Phe Lys Ser Thr Arg His Leu
            180                 185                 190

Gln Arg Phe Val Ser Ile His Asp Pro Ile Thr Asn Leu Phe His Ile
        195                 200                 205

Pro Arg His Asp Ile Pro Ser Val His His Arg Glu Leu Arg Thr Ala
    210                 215                 220

Ala Met Gln Ala Trp His Gln Ile Ala Arg Leu His Ala Ala
225                 230                 235

<210> SEQ ID NO 36
<211> LENGTH: 3879
<212> TYPE: DNA
<213> ORGANISM: A. vitis strain F2/5
<220> FEATURE:
<221> NAME/KEY: misc_feature
<222> LOCATION: (1)..(3879)
<223> OTHER INFORMATION: avi5730

<400> SEQUENCE: 36
ttgtcgcagg cgggccatga agtggtctat gggcgtcagt ctatcggctt tcgcttcgcg    60
cctgtcgggg ttgatcgtgc acacgctgga attgagacgc tgatgcttcg tcatcccctg   120
ttaaatcgtc gctttgaagt gcgggcaggc gggatcgttt atcagttgct ggccaaaag   180 cccttgcctg ttgttgagcg tgagcttgca aaggatgggg agttggagac tgtattacgg   240
gaggtttcct ccacctattc cggtagggcg cttgatctgg aaaaggatgc cgccgcgcaa   300
tttacgctat ttacggtagg tgggcaggct attggcctat tgttgtcgtt gcatcctctg   360
attggtgacc ggacggccct cgaccggttg gccgtcgatt tccttgatgg gcttgatcga   420
caggctgatt tagggcgtga agaggcgggt ttgcttgatg cagcacattg gctggttcaa   480
ggcgccgcaa tgccgcagat agcagatgct gacgccgatt tctggtttaa ccgattggtg   540
gcacaggaga cggtggcgat gctgcccgcc caggctccag cggcaggtgt ggcaaattct   600
ggtccgcaaa catggcgcga gcaggtcatc gaggtcgtgt gctcggcctc gacatctgtg   660
gttgatgtga cgcaggacag tctggcggcg ctggccattg tgcttcgtcg ctatagcggt   720
tgtggtaccc agcggatcgg gctggtgacg cggcaggccg attgccccgt tgcgacccgc   780
accgaagatc tgttgctcgt caccagcgaa atcgacggtc gtttggctct tgacgcagcg   840
cgcgaacggc tgggcgaggg ggttgccacc gcgctgtccc accatttgcc gttcgaagcg   900
ctgacgaatg ccctggcgcg gcgcgacgat gggttcgagg cagccagcct ggttgcaacg   960
```

```
gtgctggatg tgcggcccgc cctccagctg gaggctcaag gtgtggccgg tcagccggtt      1020
gccgttctgg tagagccgcc tgcgcggcgc gatgcaggtc tggtggttac cgtttccggt      1080
ctggggtcgg agacattggc gatccggctg ggctatgacc agcagagcca tagtgatgca      1140
atgatcgacc ggttcgccca cgatctccgt ctggcgttcg aggctctgcg ggggcagccg      1200
gagcagctgg tcagagcgat tgctttcatg tcggttgaag agctggaccg gctgtcagcg      1260
ccctatcccg accagcctga gaccgatgat ggcacgccga tccatcaggt gatttcggcc      1320
caggcgcagc gaaggccaga cgctttcgcg gtggcgcagg gcgatacgtc aattacccat      1380
ggcgcgctgg aagccgccgc caaccggctc gcccatcggc tggtcgccat ggggatcggc      1440
ccggaagacc gagtcgccgt ggcgctgaac aaatccatcg acgcgattat cgccattctg      1500
gcggtgctga aggccggtgg cgcttttacg ccggtcgagc cggatcatcc agaagcccgc      1560
aaccgccata tcctgagcgc gccgggtctg acgctggtga tttcgcgggg gcgttatatc      1620
accgatctgc cgcgtgatat cggcacgccg atcctcaatc tcgacacgct cgatctatcc      1680
tcggaaagca ccgagccgcc ggtcatcgcc attgcgccag cccagcttgc ctatgtgatc      1740
tatacgtccg gctccaccgg tatccccaag ggggtggctg ttgagcatgg tccgctggcg      1800
catcattgca aggcgacgct acgcatctat gaaatggatg agacttcctg cgaatatccg      1860
gtcttgccct tcacctcgga tggtgggcat gaacgctgga tggtgccgct gatggcgggt      1920
ggcggtgtgg tgctgacggc ggataagctg gcgacgccgg aagatgcttt cgcgttgatg      1980
cgcaggcacg gcgtcaacaa tgccagcttg ccgaccagct atgtccgggg ccttgccgaa      2040 tatgcggcg aaaagggcgg gataccgcag ctgcggctct attccttcgg cggtgaagcg      2100
ctatcccagg cggtcttcga tctgctgacc gataatctca aggcgcagat gctgatcaac      2160
ggttatgggc aaccgaaac catcatgacg ccgatggtgt ggaaaatccc ggcgggaacc      2220
cggtttgagg gaacggttgc accgattggc cggggtgtag gcgaccgccg catctatgtg      2280
ctggacagcg atctggtgcc ggtgccggtc ggggtgatcg gcgagatcca tatcggcggc      2340
agcggtattg ctcgcggcta tctcggccag ccggagctga cggcggatcg tttcattgat      2400
gatccttttt ccgccaacgg tgggcggatg tacaagtccg gcgatctcgg ccgctggcgc      2460
gaagatggca ctgtagaatt tgccggccgg gtcgatcacc agatcaagtt gcgtggctat      2520
cgcatcgagc cgggcgaaat cgaggcggtg ctgcgggccg atccgaacgt gtcggaagcc      2580
gtggtgctgc tgcatcagga cagtggacgc agcgcgttga tcgcctatgt ggtggcgcgt      2640
gacgatgagg atgtcaacgt caacgatctt cgccgcgccg ccgtcaccgc cctgccggat      2700
tacatggtgc cgcagcatat catggtgctt gatgcgctgc cgatggggcc gaacagcaag      2760
cttgatcgaa gcgcgctgcc gctgcccaag ctgcaacgtg atatcgtccc ccccgccgac      2820
gacaaggaag ccgccattct ggaggtctgg aaacaggtcc ttgatatcgc agaactcagc      2880
gtcaccgaaa acttcttcga tgtcggcggc cagtcgctgg cggcggtgcg gatcgtctcg      2940
cggctgaaaa tgcagcaccc gaaatggccg ctgaccattg ccgatatgtt caactatccg      3000
accgtgcggg atctggcgct ggcgatggac gaaaaccggc aggaggacaa ggtcggggcg      3060
atctatctgc gccgcgacgg cgaccgtccg gtgctctatt gcttcccggg tcttctggtc      3120
agcacgcggg aatatatgcg gttggtggat tatctcgggc cgaaccagcc ggccacgggc      3180
ttcgtctgct attcgctgac cgaaacgcca gcgctcagca ccagggtcga ggatattacc      3240
gcccgctacg ccgaagcggt gcgcagccag gctaagggac ggccttgcgc cttttcttggg      3300 tggtcctggg gcgggcttct cgcctatgag gcagcgcagc agcttggcaa tgacgtcgat      3360
```

-continued

```
cttcggatga tcggcatggt cgatgtctgc gacatgggcg atgaatttgc cattggcgtc    3420
tggccgcatt tcgaacctgg cgtgcgcgaa cgaacccatg aggccgtgca gcgctggctg    3480
acagtcgcgc caatgcgcga ggcctggttg acgctaatgg cggcgatgga tgccgaggtt    3540
tacgagcaat tcctgcatca tatcgttaag cataacgtgc cgctgcctgt cgatgggccg    3600
gatatcggct cggaagagca tattttctgg gttctgctcg ataacgcgat gattttccgt    3660
aattatcagc tgaaaacctc cgcgttccgc atccatgcgt tttcggctga agattcggta    3720
acgcggggcc tcagtgtcat cgactggcgc cgctattctc ctaatgcgac ggcttgcgaa    3780
ttggtgaccg gcaccaacca tctgtcgatt atcggcaagt cccgtttcca tcagcgtttt    3840
gcccagcggc tcgatctagc catccaggac aagccctaa                           3879
```

<210> SEQ ID NO 37
<211> LENGTH: 1292
<212> TYPE: PRT
<213> ORGANISM: A. vitis strain F2/5
<220> FEATURE:
<221> NAME/KEY: MISC_FEATURE
<222> LOCATION: (1)..(1292)
<223> OTHER INFORMATION: avi5730

<400> SEQUENCE: 37

Met Ser Gln Ala Gly His Glu Val Val Tyr Gly Arg Gln Ser Ile Gly
1               5                   10                  15

Phe Arg Phe Ala Pro Val Gly Val Asp Arg Ala His Ala Gly Ile Glu
                20                  25                  30

Thr Leu Met Leu Arg His Pro Leu Leu Asn Arg Arg Phe Glu Val Arg
            35                  40                  45

Ala Gly Gly Ile Val Tyr Gln Leu Leu Gly Gln Lys Pro Leu Pro Val
        50                  55                  60

Val Glu Arg Glu Leu Ala Lys Asp Gly Glu Leu Glu Thr Val Leu Arg
65                  70                  75                  80

Glu Val Ser Ser Thr Tyr Ser Gly Arg Ala Leu Asp Leu Glu Lys Asp
                85                  90                  95

Ala Ala Ala Gln Phe Thr Leu Phe Thr Val Gly Gly Gln Ala Ile Gly
                100                 105                 110

Leu Leu Leu Ser Leu His Pro Leu Ile Gly Asp Arg Thr Ala Leu Asp
            115                 120                 125

Arg Leu Ala Val Asp Phe Leu Asp Gly Leu Arg Gln Ala Asp Leu
        130                 135                 140

Gly Arg Glu Glu Ala Gly Leu Leu Asp Ala Ala His Trp Leu Val Gln
145                 150                 155                 160

Gly Ala Ala Met Pro Gln Ile Ala Asp Ala Asp Phe Trp Phe
                165                 170                 175

Asn Arg Leu Val Ala Gln Glu Thr Val Ala Met Leu Pro Ala Gln Ala
                180                 185                 190

Pro Ala Ala Gly Val Ala Asn Ser Gly Pro Gln Thr Trp Arg Glu Gln
            195                 200                 205

Val Ile Glu Val Val Cys Ser Ala Ser Thr Ser Val Val Asp Val Thr
        210                 215                 220

Gln Asp Ser Leu Ala Ala Leu Ala Ile Val Leu Arg Arg Tyr Ser Gly
225                 230                 235                 240

Cys Gly Thr Gln Arg Ile Gly Leu Val Thr Arg Gln Ala Asp Cys Pro
                245                 250                 255

```
Val Ala Thr Arg Thr Glu Asp Leu Leu Leu Val Thr Ser Glu Ile Asp
                260                 265                 270

Gly Arg Leu Ala Leu Asp Ala Ala Arg Glu Arg Leu Gly Glu Gly Val
        275                 280                 285

Ala Thr Ala Leu Ser His His Leu Pro Phe Glu Ala Leu Thr Asn Ala
    290                 295                 300

Leu Ala Arg Arg Asp Asp Gly Phe Glu Ala Ala Ser Leu Val Ala Thr
305                 310                 315                 320

Val Leu Asp Val Arg Pro Ala Leu Gln Leu Glu Ala Gln Gly Val Ala
                325                 330                 335

Gly Gln Pro Val Ala Val Leu Val Glu Pro Pro Ala Arg Arg Asp Ala
            340                 345                 350

Gly Leu Val Val Thr Val Ser Gly Leu Gly Ser Glu Thr Leu Ala Ile
        355                 360                 365

Arg Leu Gly Tyr Asp Gln Gln Ser His Ser Asp Ala Met Ile Asp Arg
    370                 375                 380

Phe Ala His Asp Leu Arg Leu Ala Phe Glu Ala Leu Arg Gly Gln Pro
385                 390                 395                 400

Glu Gln Leu Val Arg Ala Ile Ala Phe Met Ser Val Glu Glu Leu Asp
                405                 410                 415

Arg Leu Ser Ala Pro Tyr Pro Asp Gln Pro Glu Thr Asp Asp Gly Thr
            420                 425                 430

Pro Ile His Gln Val Ile Ser Ala Gln Ala Gln Arg Arg Pro Asp Ala
        435                 440                 445

Phe Ala Val Ala Gln Gly Asp Thr Ser Ile Thr His Gly Ala Leu Glu
    450                 455                 460

Ala Ala Ala Asn Arg Leu Ala His Arg Leu Val Ala Met Gly Ile Gly
465                 470                 475                 480

Pro Glu Asp Arg Val Ala Val Ala Leu Asn Lys Ser Ile Asp Ala Ile
                485                 490                 495

Ile Ala Ile Leu Ala Val Leu Lys Ala Gly Gly Ala Phe Thr Pro Val
            500                 505                 510

Glu Pro Asp His Pro Glu Ala Arg Asn Arg His Ile Leu Ser Ala Pro
        515                 520                 525

Gly Leu Thr Leu Val Ile Ser Arg Gly Arg Tyr Ile Thr Asp Leu Pro
    530                 535                 540

Arg Asp Ile Gly Thr Pro Ile Leu Asn Leu Asp Thr Leu Asp Leu Ser
545                 550                 555                 560

Ser Glu Ser Thr Glu Pro Pro Val Ile Ala Ile Ala Pro Ala Gln Leu
                565                 570                 575

Ala Tyr Val Ile Tyr Thr Ser Gly Ser Thr Gly Ile Pro Lys Gly Val
            580                 585                 590

Ala Val Glu His Gly Pro Leu Ala His His Cys Lys Ala Thr Leu Arg
        595                 600                 605

Ile Tyr Glu Met Asp Glu Thr Ser Cys Glu Tyr Pro Val Leu Pro Phe
    610                 615                 620

Thr Ser Asp Gly Gly His Glu Arg Trp Met Val Pro Leu Met Ala Gly
625                 630                 635                 640

Gly Gly Val Val Leu Thr Ala Asp Lys Leu Ala Thr Pro Glu Asp Ala
                645                 650                 655

Phe Ala Leu Met Arg Arg His Gly Val Asn Asn Ala Ser Leu Pro Thr
            660                 665                 670

Ser Tyr Val Arg Gly Leu Ala Glu Tyr Ala Ala Glu Lys Gly Gly Ile
```

```
                675                 680                 685
Pro Gln Leu Arg Leu Tyr Ser Phe Gly Gly Glu Ala Leu Ser Gln Ala
    690                 695                 700
Val Phe Asp Leu Leu Thr Asp Asn Leu Lys Ala Gln Met Leu Ile Asn
705                 710                 715                 720
Gly Tyr Gly Pro Thr Glu Thr Ile Met Thr Pro Met Val Trp Lys Ile
                725                 730                 735
Pro Ala Gly Thr Arg Phe Glu Gly Thr Val Ala Pro Ile Gly Arg Gly
            740                 745                 750
Val Gly Asp Arg Arg Ile Tyr Val Leu Asp Ser Asp Leu Val Pro Val
            755                 760                 765
Pro Val Gly Val Ile Gly Glu Ile His Ile Gly Ser Gly Ile Ala
            770                 775                 780
Arg Gly Tyr Leu Gly Gln Pro Glu Leu Thr Ala Asp Arg Phe Ile Asp
785                 790                 795                 800
Asp Pro Phe Ser Ala Asn Gly Arg Met Tyr Lys Ser Gly Asp Leu
                805                 810                 815
Gly Arg Trp Arg Glu Asp Gly Thr Val Glu Phe Ala Gly Arg Val Asp
            820                 825                 830
His Gln Ile Lys Leu Arg Gly Tyr Arg Ile Glu Pro Gly Glu Ile Glu
            835                 840                 845
Ala Val Leu Arg Ala Asp Pro Asn Val Ser Glu Ala Val Val Leu Leu
            850                 855                 860
His Gln Asp Ser Gly Arg Ser Ala Leu Ile Ala Tyr Val Val Ala Arg
865                 870                 875                 880
Asp Asp Glu Asp Val Asn Val Asn Asp Leu Arg Arg Ala Ala Val Thr
                885                 890                 895
Ala Leu Pro Asp Tyr Met Val Pro Gln His Ile Met Val Leu Asp Ala
                900                 905                 910
Leu Pro Met Gly Pro Asn Ser Lys Leu Asp Arg Ser Ala Leu Pro Leu
            915                 920                 925
Pro Lys Leu Gln Arg Asp Ile Val Pro Ala Asp Asp Lys Glu Ala
930                 935                 940
Ala Ile Leu Glu Val Trp Lys Gln Val Leu Asp Ile Ala Glu Leu Ser
945                 950                 955                 960
Val Thr Glu Asn Phe Phe Asp Val Gly Gly Gln Ser Leu Ala Ala Val
                965                 970                 975
Arg Ile Val Ser Arg Leu Lys Met Gln His Pro Lys Trp Pro Leu Thr
            980                 985                 990
Ile Ala Asp Met Phe Asn Tyr Pro Thr Val Arg Asp Leu Ala Leu Ala
            995                 1000                1005
Met Asp Glu Asn Arg Gln Glu Asp Lys Val Gly Ala Ile Tyr Leu
    1010                1015                1020
Arg Arg Asp Gly Asp Arg Pro Val Leu Tyr Cys Phe Pro Gly Leu
    1025                1030                1035
Leu Val Ser Thr Arg Glu Tyr Met Arg Leu Val Asp Tyr Leu Gly
    1040                1045                1050
Pro Asn Gln Pro Ala Thr Gly Phe Val Cys Tyr Ser Leu Thr Glu
    1055                1060                1065
Thr Pro Ala Leu Ser Thr Arg Val Glu Asp Ile Thr Ala Arg Tyr
    1070                1075                1080
Ala Glu Ala Val Arg Ser Gln Ala Lys Gly Arg Pro Cys Ala Phe
    1085                1090                1095
```

-continued

```
Leu Gly  Trp Ser Trp Gly Gly  Leu Leu Ala Tyr Glu  Ala Ala Gln
    1100                 1105                 1110

Gln Leu  Gly Asn Asp Val Asp  Leu Arg Met Ile Gly  Met Val Asp
    1115                 1120                 1125

Val Cys  Asp Met Gly Asp Glu  Phe Ala Ile Gly Val  Trp Pro His
    1130                 1135                 1140

Phe Glu  Pro Gly Val Arg Glu  Arg Thr His Glu Ala  Val Gln Arg
    1145                 1150                 1155

Trp Leu  Thr Val Ala Pro Met  Arg Glu Ala Trp Leu  Thr Leu Met
    1160                 1165                 1170

Ala Ala  Met Asp Ala Glu Val  Tyr Glu Gln Phe Leu  His His Ile
    1175                 1180                 1185

Val Lys  His Asn Val Pro Leu  Pro Val Asp Gly Pro  Asp Ile Gly
    1190                 1195                 1200

Ser Glu  Glu His Ile Phe Trp  Val Leu Leu Asp Asn  Ala Met Ile
    1205                 1210                 1215

Phe Arg  Asn Tyr Gln Leu Lys  Thr Ser Ala Phe Arg  Ile His Ala
    1220                 1225                 1230

Phe Ser  Ala Glu Asp Ser Val  Thr Arg Gly Leu Ser  Val Ile Asp
    1235                 1240                 1245

Trp Arg  Arg Tyr Ser Pro Asn  Ala Thr Ala Cys Glu  Leu Val Thr
    1250                 1255                 1260

Gly Thr  Asn His Leu Ser Ile  Ile Gly Lys Ser Arg  Phe His Gln
    1265                 1270                 1275

Arg Phe  Ala Gln Arg Leu Asp  Leu Ala Ile Gln Asp  Lys Pro
    1280                 1285                 1290
```